US012678165B2

(12) United States Patent
Cropper et al.

(10) Patent No.: US 12,678,165 B2
(45) Date of Patent: Jul. 14, 2026

(54) CLOSURE LOCKOUT SYSTEMS FOR SURGICAL INSTRUMENTS

(71) Applicant: Cilag GmbH International, Zug (CH)

(72) Inventors: Michael S. Cropper, Edgewood, KY (US); Michael E. Setser, Burlington, KY (US); Barry T. Jamison, Fairfield, OH (US); Paul H Kistler, Brandon, FL (US); John R. Dugan, Lebanon, OH (US); Sudhir B. Patel, Zephyrhills, FL (US)

(73) Assignee: Cilag GmbH International, Zug (CH)

( * ) Notice: Subject to any disclaimer, the term of this patent is extended or adjusted under 35 U.S.C. 154(b) by 47 days.

(21) Appl. No.: 18/627,631

(22) Filed: Apr. 5, 2024

(65) Prior Publication Data

US 2024/0245403 A1    Jul. 25, 2024

Related U.S. Application Data

(63) Continuation of application No. 18/081,259, filed on Dec. 14, 2022, now Pat. No. 12,070,215, which is a
(Continued)

(51) Int. Cl.
A61B 17/10 (2006.01)
A61B 17/00 (2006.01)
(Continued)

(52) U.S. Cl.
CPC .......... A61B 17/105 (2013.01); A61B 17/068 (2013.01); A61B 17/07207 (2013.01);
(Continued)

(58) Field of Classification Search
CPC ................ A61B 17/105; A61B 17/068; A61B 17/07207; A61B 2090/035;
(Continued)

(56) References Cited

U.S. PATENT DOCUMENTS 5,397,046 A * 3/1995 Savage ............ A61B 17/07207
227/176.1
5,470,006 A 11/1995 Rodak
(Continued)

FOREIGN PATENT DOCUMENTS

CN      201949071 U    8/2011
EP       0621006 A1    10/1994
(Continued)

OTHER PUBLICATIONS

Australian Office Action dated Feb. 28, 2019, for Application No. 2015275140, 4 pages.
(Continued)

*Primary Examiner* — Dariush Seif
(74) *Attorney, Agent, or Firm* — FBT Gibbons LLP

(57) ABSTRACT

A surgical instrument is disclosed. The surgical instrument can include a first jaw, a second jaw, and a jaw closure lockout system. The first jaw can comprise a pivot pin slot and a slide pin slot. The second jaw can comprise an anvil and, in addition, a mounting portion comprising a pivot pin, which can be movably positioned in the pivot pin slot. A shiftable guide can be movably positioned in the first jaw and can comprise a body and a barrier wall. The body can comprise a slide pin movably positioned in the slide pin slot. The barrier wall can be aligned with a portion of the pivot pin slot when the slide pin is positioned within a range of positions in the slide pin slot, and the barrier wall can be offset from the pivot pin slot when the slide pin is positioned outside the range of positions.

20 Claims, 37 Drawing Sheets

Related U.S. Application Data continuation of application No. 16/936,506, filed on Jul. 23, 2020, now Pat. No. 11,547,410, which is a continuation of application No. 16/058,427, filed on Aug. 8, 2018, now Pat. No. 10,729,441, which is a continuation of application No. 14/304,077, filed on Jun. 13, 2014, now Pat. No. 10,045,781.

(51) Int. Cl.

| | |
|---|---|
| *A61B 17/068* | (2006.01) |
| *A61B 17/072* | (2006.01) |
| *A61B 17/29* | (2006.01) |
| *A61B 90/00* | (2016.01) |

(52) U.S. Cl.

CPC .............. *A61B 2017/00309* (2013.01); *A61B 2017/07214* (2013.01); *A61B 2017/07257* (2013.01); *A61B 2017/07271* (2013.01); *A61B 2017/2936* (2013.01); *A61B 2090/035* (2016.02)

(58) Field of Classification Search

CPC A61B 2017/00309; A61B 2017/07214; A61B 2017/07257; A61B 2017/07271; A61B 2017/2936

USPC ........................................... 227/175.1–182.1

See application file for complete search history.

(56) References Cited

U.S. PATENT DOCUMENTS

| | | | |
|---|---|---|---|
| 5,470,009 A | 11/1995 | Rodak | |
| 5,485,947 A * | 1/1996 | Olson .............. | A61B 17/07207 227/176.1 |
| 5,662,667 A * | 9/1997 | Knodel ............ | A61B 17/07207 606/151 |
| 5,715,988 A | 2/1998 | Palmer | |
| 5,878,938 A | 3/1999 | Bittner et al. | |
| 6,032,849 A * | 3/2000 | Mastri .............. | A61B 17/07207 227/176.1 |
| 6,109,500 A | 8/2000 | Alli et al. | |
| 6,250,532 B1 | 6/2001 | Green et al. | |
| 7,510,107 B2 * | 3/2009 | Timm .............. | A61B 17/07207 227/176.1 |
| 7,721,931 B2 | 5/2010 | Shelton, IV et al. | |
| 8,360,297 B2 * | 1/2013 | Shelton, IV ......... | A61B 17/068 227/181.1 |
| 8,439,246 B1 * | 5/2013 | Knodel ................. | A61B 90/92 227/176.1 |
| 9,078,653 B2 * | 7/2015 | Leimbach ............ | A61B 17/105 |
| 9,603,595 B2 * | 3/2017 | Shelton, IV ..... | A61B 17/07207 |
| 9,848,877 B2 * | 12/2017 | Shelton, IV ..... | A61B 17/07207 |
| 10,045,781 B2 | 8/2018 | Cropper et al. | |
| 10,729,441 B2 | 8/2020 | Cropper et al. | |
| 11,547,410 B2 | 1/2023 | Cropper et al. | |
| 12,070,215 B2 | 8/2024 | Cropper et al. | |
| 2002/0062136 A1 * | 5/2002 | Hillstead .......... | A61B 17/07207 606/205 |

| | | | |
|---|---|---|---|
| 2005/0023324 A1 * | 2/2005 | Doll ................. | A61B 17/07207 227/175.2 |
| 2005/0222616 A1 | 10/2005 | Rethy et al. | |
| 2007/0084896 A1 * | 4/2007 | Doll ................. | A61B 17/07207 227/19 |
| 2007/0175956 A1 | 8/2007 | Swayze et al. | |
| 2008/0169328 A1 * | 7/2008 | Shelton ................ | A61B 17/072 227/176.1 |
| 2008/0300579 A1 * | 12/2008 | Broehl ............. | A61B 17/07207 606/1 |
| 2010/0076474 A1 | 3/2010 | Yates et al. | |
| 2010/0301095 A1 | 12/2010 | Shelton, IV et al. | |
| 2011/0006103 A1 | 1/2011 | Laurent et al. | |
| 2011/0163147 A1 | 7/2011 | Laurent et al. | |
| 2012/0080493 A1 | 4/2012 | Shelton, IV et al. | |
| 2012/0138660 A1 * | 6/2012 | Shelton, IV .......... | A61B 34/71 227/176.1 |
| 2012/0181322 A1 * | 7/2012 | Whitman ............. | A61B 17/068 227/176.1 |
| 2012/0199632 A1 * | 8/2012 | Spivey ........... | A61B 17/320016 227/176.1 |
| 2012/0239009 A1 * | 9/2012 | Mollere ........... | A61B 17/07207 606/1 |
| 2012/0241499 A1 * | 9/2012 | Baxter, III ......... | A61B 17/0644 227/176.1 |
| 2013/0138102 A1 * | 5/2013 | Twomey ................ | A61B 17/29 606/45 |
| 2013/0248577 A1 * | 9/2013 | Leimbach ........ | A61B 17/07207 227/176.1 |
| 2015/0173755 A1 * | 6/2015 | Baxter, III ....... | A61B 17/07207 227/180.1 |
| 2015/0173756 A1 * | 6/2015 | Baxter, III ....... | A61B 17/07207 227/177.1 |
| 2015/0289874 A1 * | 10/2015 | Leimbach ............ | A61B 17/072 227/176.1 |
| 2015/0359536 A1 * | 12/2015 | Cropper ........... | A61B 17/07207 227/177.1 |
| 2019/0038287 A1 * | 2/2019 | Cropper ............... | A61B 17/105 |
| 2024/0245403 A1 * | 7/2024 | Cropper ........... | A61B 17/07207 |

FOREIGN PATENT DOCUMENTS

| | | |
|---|---|---|
| EP | 1782738 A2 | 5/2007 |
| JP | 2004-147702 A | 5/2004 |
| JP | 2014-505508 A | 3/2014 |
| RU | 61122 U1 | 2/2007 |

OTHER PUBLICATIONS

European Search Report and Written Opinion dated Aug. 3, 2015, for Application No. 15171897.0, 8 pages.

European Partial Search Report and Written Opinion dated Jun. 25, 2018, for Application No. 17202915.9, 9 pages.

International Search Report and Written Opinion dated Aug. 4, 2015, for International Application No. PCT/US2015/030935, 12 pages.

Japanese Office Action and Search Report dated Mar. 19, 2019, for Application No. 2016-572612, 23 pages.

Russian Office Action dated Dec. 12, 2018, for Application No. 2017100901/14, 8 pages.

\* cited by examiner

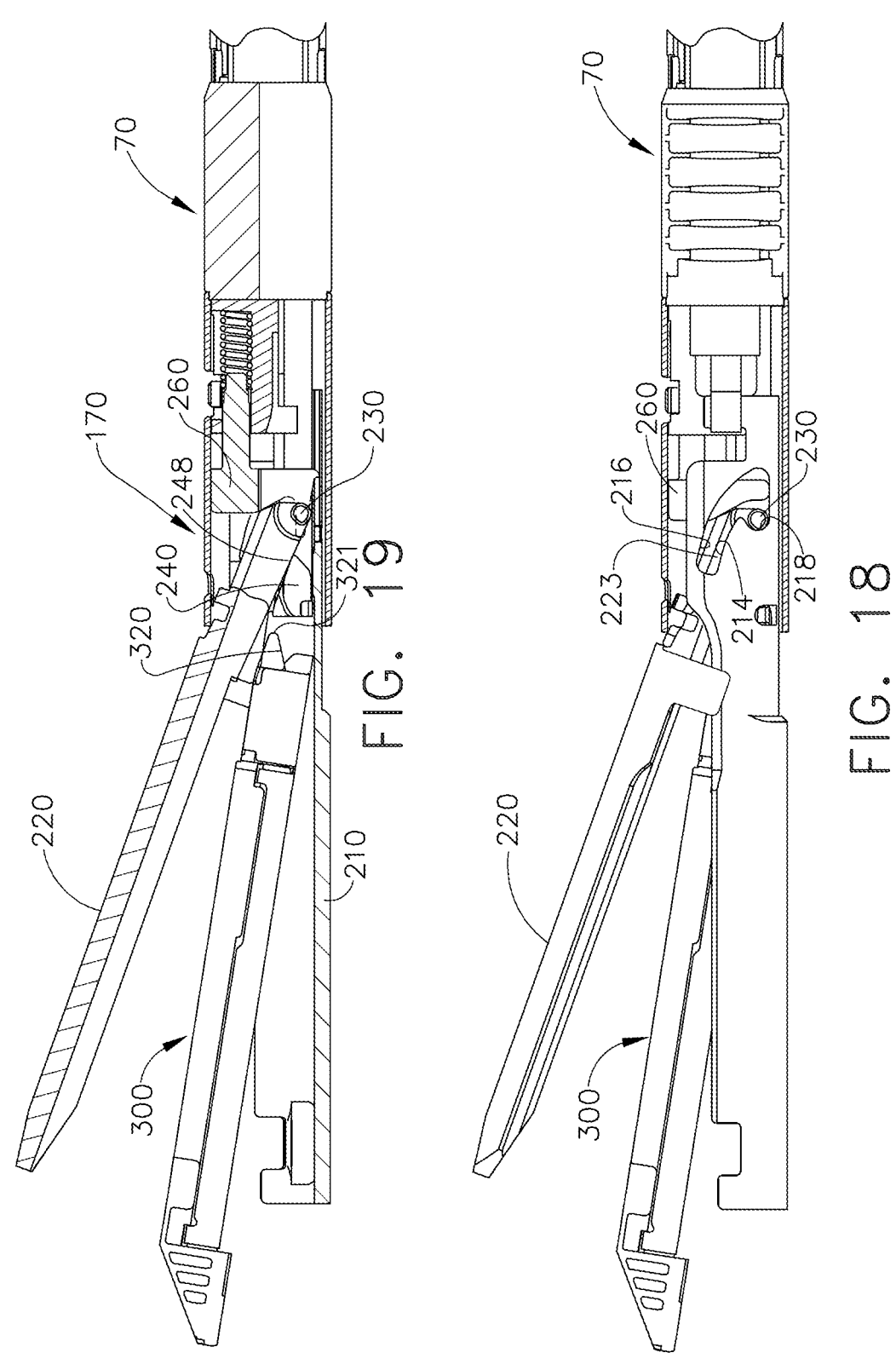

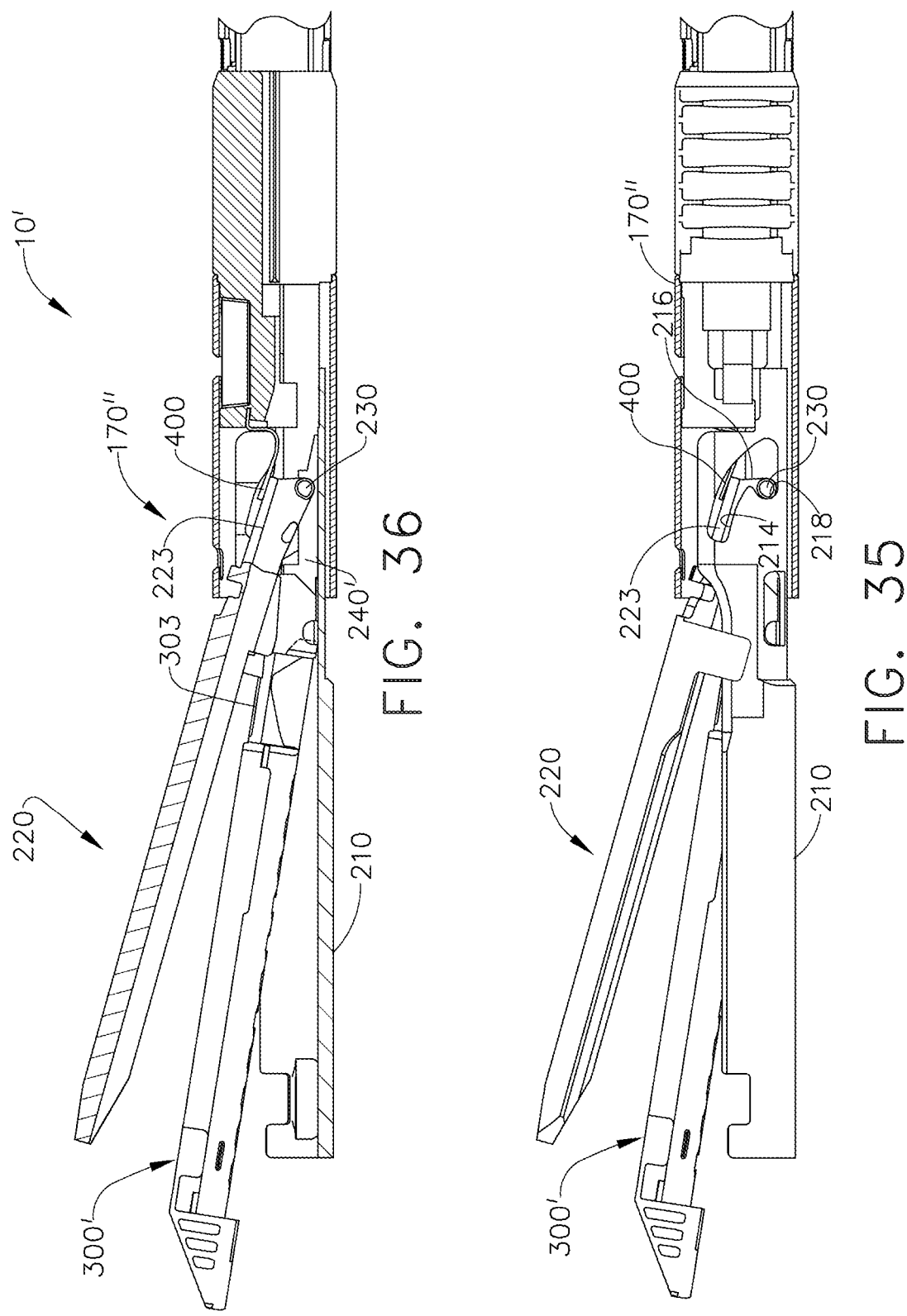

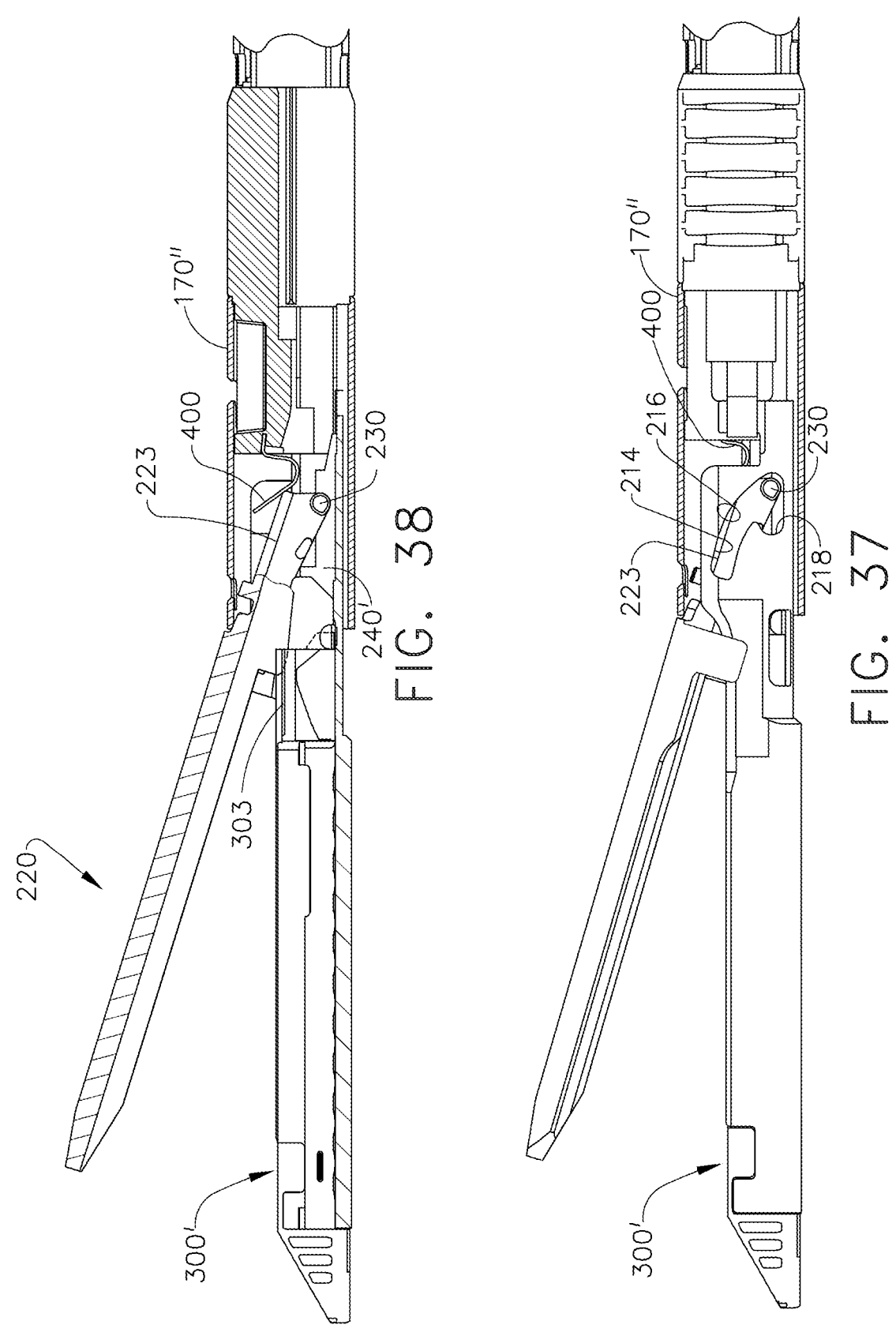

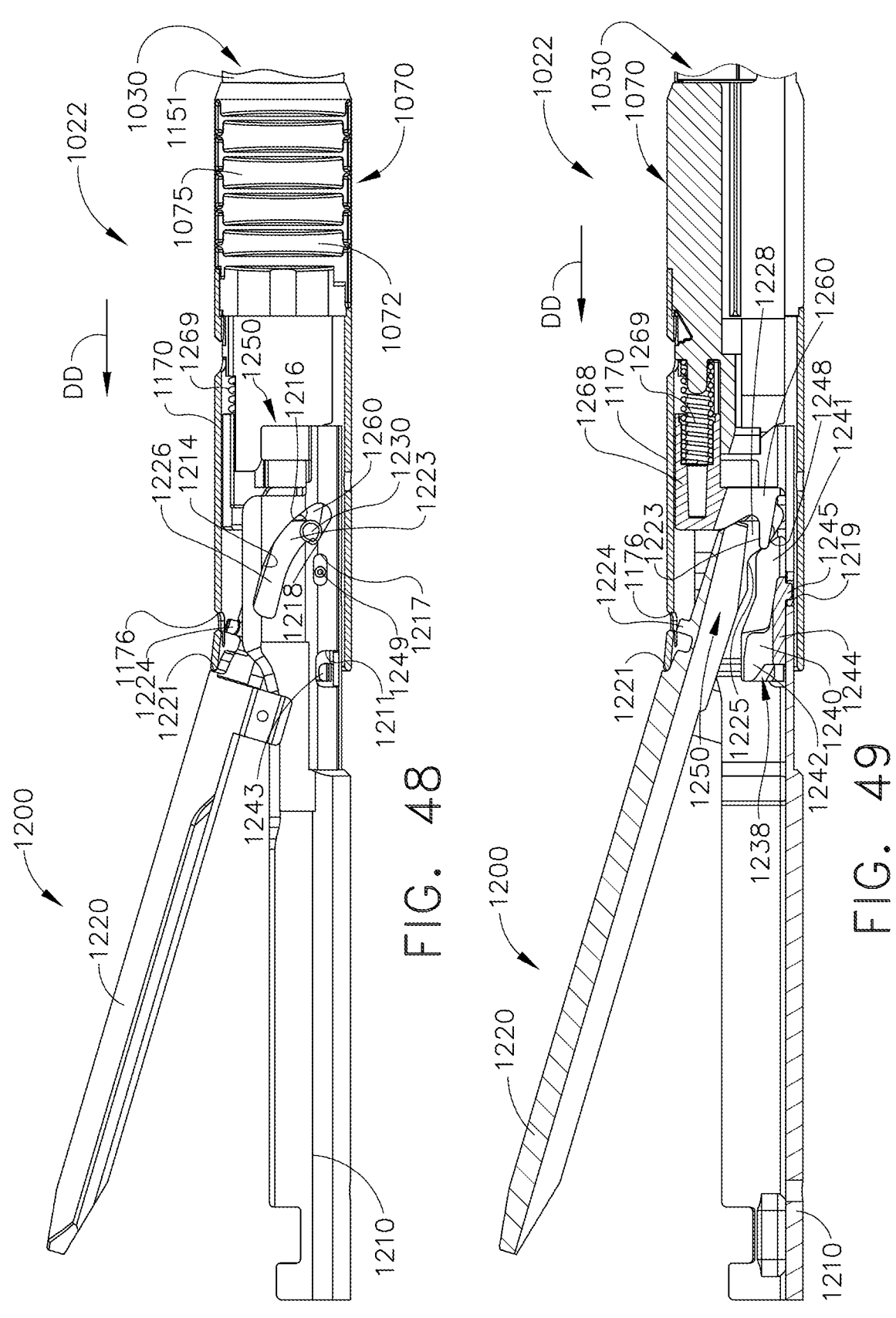

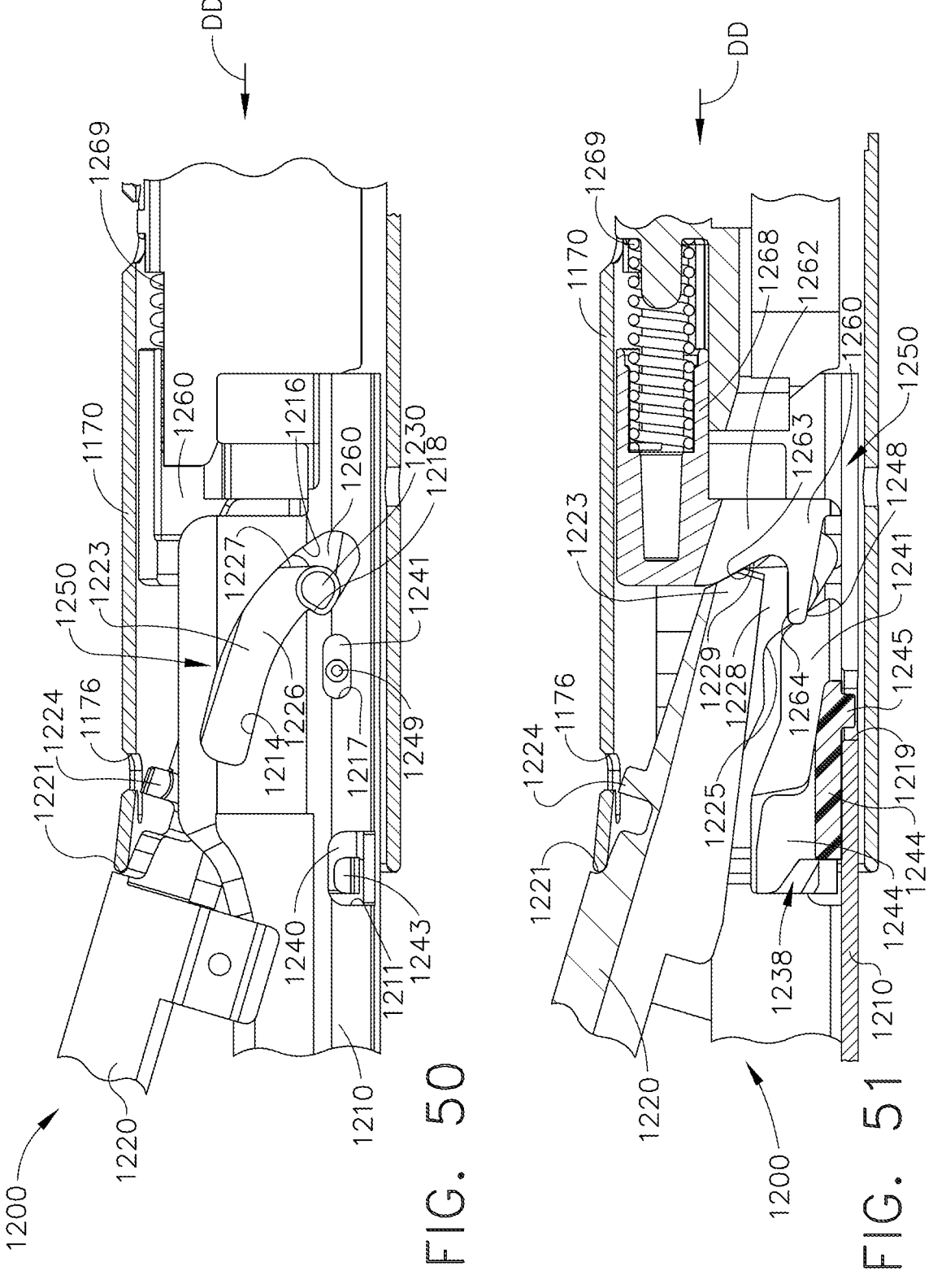

CLOSURE LOCKOUT SYSTEMS FOR SURGICAL INSTRUMENTS

CROSS-REFERENCE TO RELATED APPLICATIONS

This application is a continuation of U.S. patent application Ser. No. 18/081,259, entitled CLOSURE LOCKOUT SYSTEMS FOR SURGICAL INSTRUMENTS, filed Dec. 14, 2022, published as U.S. Pat. Pub. No. 2023/0190271 on Jun. 22, 2023, which is a continuation of U.S. patent application Ser. No. 16/936,506, entitled CLOSURE LOCKOUT SYSTEMS FOR SURGICAL INSTRU-MENTS, filed Jul. 23, 2020, issued as U.S. Pat. No. 11,547, 410 on Jan. 10, 2023, which is a continuation of U.S. patent application Ser. No. 16/058,427, entitled CLOSURE LOCKOUT SYSTEMS FOR SURGICAL INSTRU-MENTS, filed Aug. 8, 2018, issued as U.S. Pat. No. 10,729, 441 on Aug. 4, 2020, which is a continuation of U.S. patent application Ser. No. 14/304,077, entitled CLOSURE LOCKOUT SYSTEMS FOR SURGICAL INSTRU-MENTS, filed Jun. 13, 2014, issued as U.S. Pat. No. 10,045,781 on Aug. 14, 2018, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 18 is a side view of an end effector embodiment of FIGS. 16 and 17 with the anvil in the open position and wherein a surgical staple cartridge is being inserted into the elongate channel;

FIG. 19 is a cross-sectional view of the end effector of FIG. 18;

FIG. 35 is a side view of an end effector embodiment of FIGS. 33 and 34 with the anvil in the open position and wherein a surgical staple cartridge is being inserted into the elongate channel;

FIG. 36 is a cross-sectional view of the end effector of FIG. 35;

FIG. 37 is a side view of the end effector of FIGS. 33-36 with the staple cartridge embodiment seated within the elongate channel;

FIG. 38 is a cross-sectional view of the end effector of FIG. 37;

FIG. 48 is an elevation view of the end effector of FIG. 43 depicting the anvil in an open orientation, an anvil lockout system, and the staple cartridge removed from the elongate channel, wherein the closure tube of the end effector has been illustrated in cross-section to illustrate various other aspects of the end effector;

FIG. 49 is a cross-sectional elevation view of the end effector of FIG. 43 in the configuration illustrated in FIG. 48;

FIG. 50 is a detail view of the anvil lockout system as depicted in FIG. 48;

FIG. 51 is a detail view of the anvil lockout system as depicted in FIG. 49;

DETAILED DESCRIPTION

Figure 1:
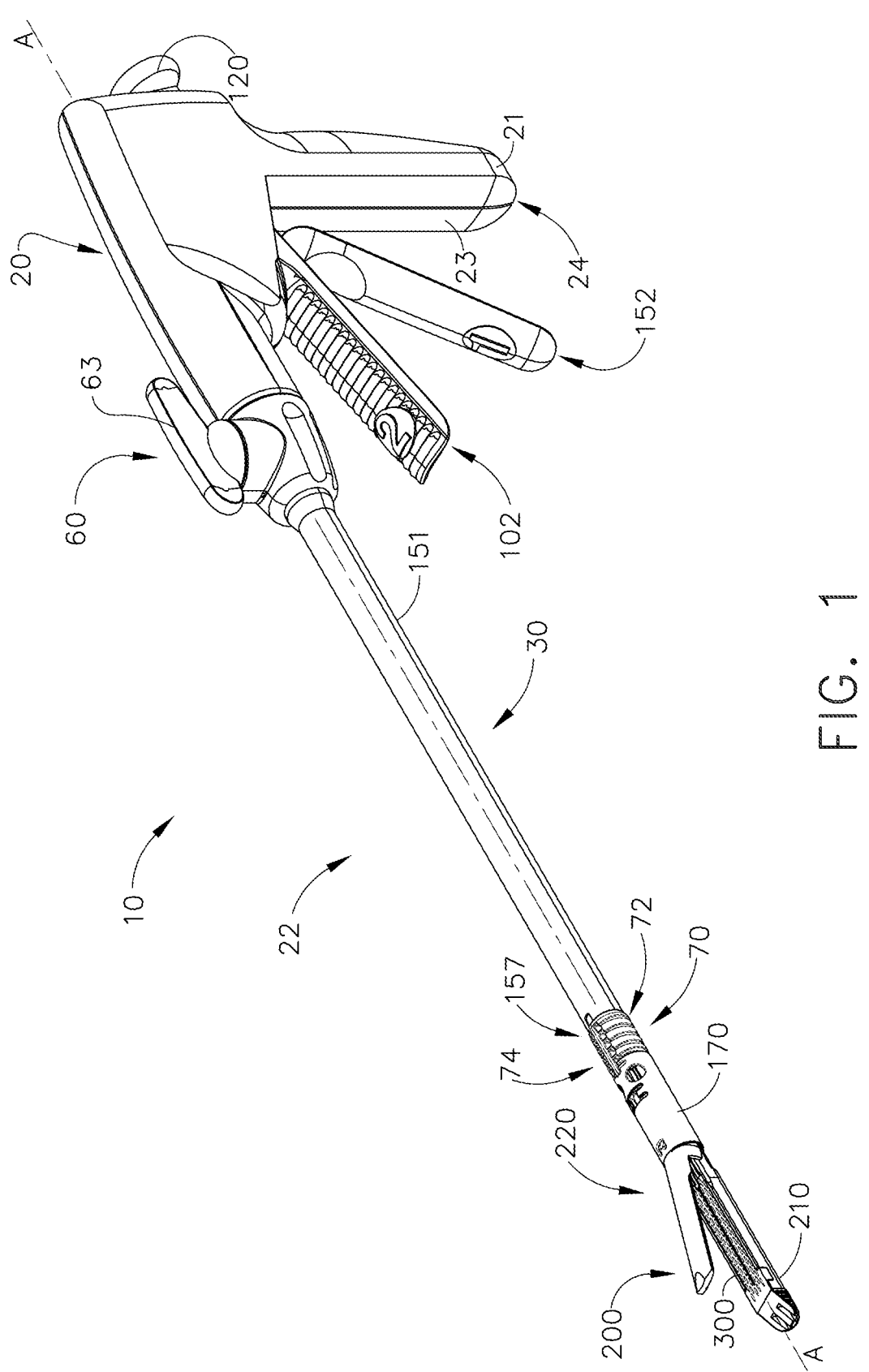
FIG. 1 is a perspective view of a surgical stapling instrument embodiment.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 2:
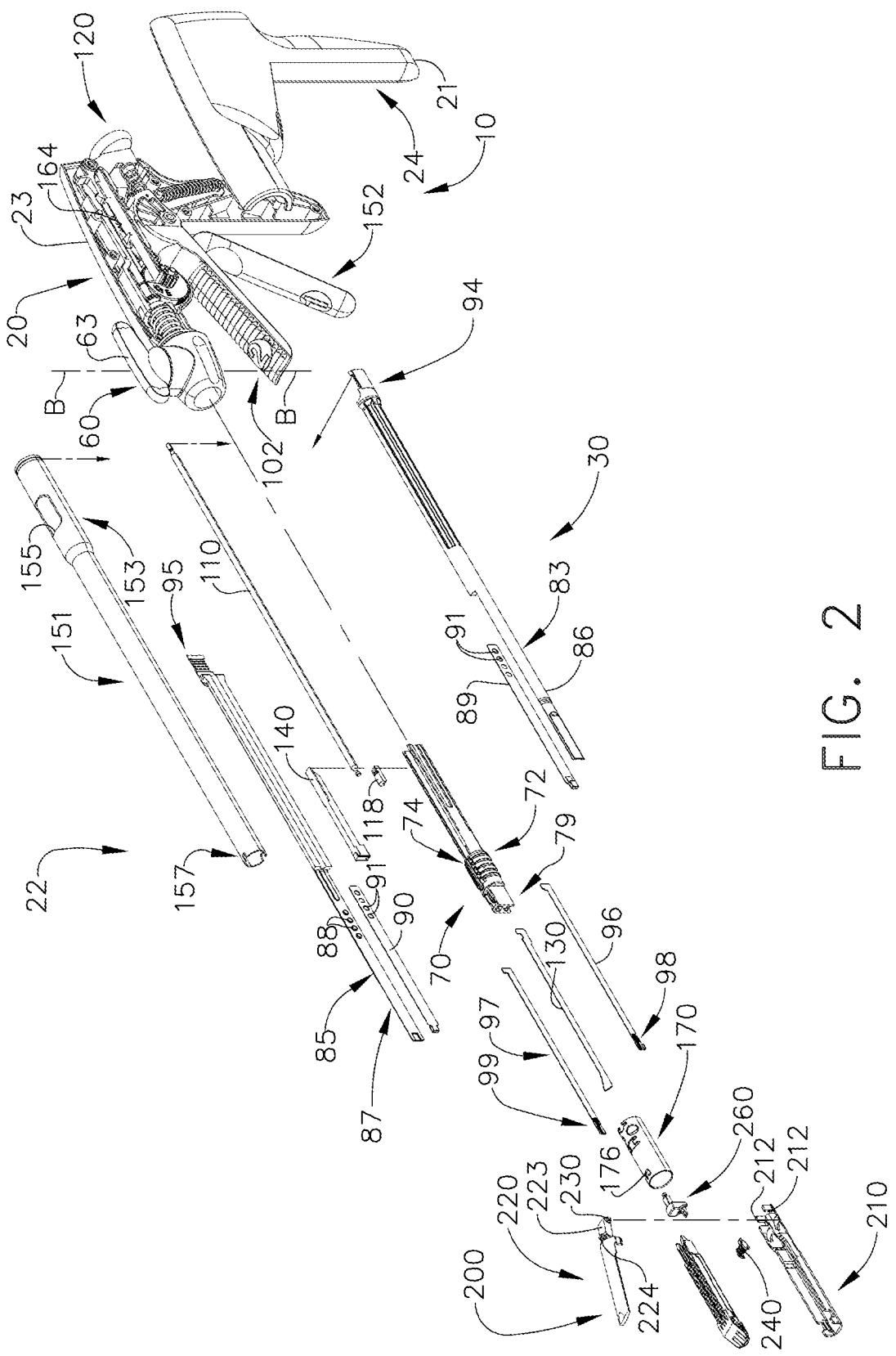
FIG. 2 is an exploded assembly view of the surgical stapling instrument of FIG. 1.

Turning to the Drawings wherein like numerals denote like components throughout the several views, FIGS. 1 and 2 depict a surgical stapling device 10 that is capable of practicing the unique benefits of various embodiments disclosed herein. An exemplary surgical device that has features with which embodiments of the present invention may be effectively employed is disclosed in U.S. Pat. No. 5,704,534, entitled ARTICULATION ASSEMBLY FOR SURGICAL INSTRUMENTS, which issued Jun. 6, 1998, the entire disclosure of which is herein incorporated by reference. Various other exemplary surgical stapling device embodiments are described in greater detail in the following U.S.

patents which are each herein incorporated by reference in their respective entireties: U.S. Pat. No. 6,964,363, entitled SURGICAL STAPLING INSTRUMENT HAVING ARTICULATION JOINT SUPPORT PLATES FOR SUPPORTING A FIRING BAR, which issued Nov. 15, 2005; U.S. Pat. No. 7,000,818, entitled SURGICAL STAPLING INSTRUMENT HAVING SEPARATE DISTINCT CLOSING AND FIRING MOTIONS, which issued Feb. 21, 2006; U.S. Pat. No. 7,044,352, entitled SURGICAL STAPLING INSTRUMENT HAVING A SINGLE LOCKOUT MECHANISM FOR PREVENTION OF FIRING, which issued May 16, 2006; U.S. Pat. No. 7,111,769, entitled SURGICAL INSTRUMENT INCORPORATING AN ARTICULATION MECHANISM HAVING ROTATION ABOUT THE LONGITUDINAL AXIS, which issued Sep. 26, 2006; and U.S. Pat. No. 7,143,923, entitled SURGICAL STAPLING INSTRUMENT HAVING A FIRING LOCKOUT FOR AN UNCLOSED ANVIL, which issued Dec. 5, 2006.

Referring again to FIGS. 1 and 2, the depicted surgical stapling device 10 includes a handle 20 that is operably connected to an implement portion 22, the latter further comprising an elongate shaft assembly 30 that is operably coupled to an end effector 200. The handle 20 includes a pistol grip 24 toward which a closure trigger 152 is pivotally drawn by the clinician to cause clamping, or closing, of an anvil 220 toward an elongate channel 210 of the end effector 200. A firing trigger 102 is farther outboard of the closure trigger 152 and is pivotally drawn by the clinician to cause the stapling and severing of clamped tissue in the end effector 200.

For example, closure trigger 152 is actuated first. Once the clinician is satisfied with the positioning of the end effector 200, the clinician may draw back the closure trigger 152 to its fully closed, locked position proximate to the pistol grip 24. Then, the firing trigger 102 is actuated. The firing trigger 102 springedly returns when the clinician removes pressure. A release button 120 when depressed on the proximal end of the handle 20 releases the locked closure trigger 152.

Articulation System

The depicted embodiment includes an articulation assembly 62 that is configured to facilitate articulation of the end effector 200 about the elongate axis A-A of the device 10. Various embodiments, however, may also be effectively employed in connection with non-articulatable surgical stapling devices. As can be seen in FIG. 2, for example, the elongate shaft assembly 30 includes a proximal closure tube segment 151 that is operably supported by a nozzle 60 that is supported on the handle 20. The handle 20 may be formed from two handle cases 21, 23 that operably contain firing and closure systems 100, 150. A proximal end portion 153 of the proximal closure tube segment 151 is rotatably supported by the handle 20 to facilitate its selective rotation about the elongate axis A-A. See FIG. 1. As can also be seen in FIGS. 1 and 2, in at least one embodiment, a distal end portion 157 of the proximal closure tube segment 151 is coupled to a flexible neck assembly 70. The flexible neck assembly 70 has first and second flexible neck portions, 72 and 74, which receive first and second elongate flexible transmission band assemblies 83, 85. The first and second transmission band assemblies 83, 85 have exterior reinforcement band portions 86, 87, respectively, extending distally from the structural portions of the bands. Each exterior reinforcement band portion 86, 87 has a plurality of attachment lugs 88 for securing first and second interior articulation bands 89, 90. See FIG. 2. The transmission band assemblies 83, 85 may be, for example, composed of a plastic, especially a glass fiber-reinforced amorphous polyamide, sold commercially under the trade name Grivory GV-6H by EMS-American Grilon. In contrast, it may be desired that the interior articulation bands 89, 90 of the transmission band assemblies 83, 85 be composed of a metal, advantageously full hard 301 stainless steel or its equivalent. The attachment lugs 88 on the exterior reinforcement band portions 86, 87 of the transmission bands 83, 85 are received into and secured within a plurality of lug holes 91 on the corresponding interior articulation band 89, 90. At the distal end of the first and second interior articulation band assemblies 89, 90 there are first and second connectors 92, 93. The articulation assembly further comprises distal articulation bands 96 and 97 that are configured to hookingly engage the first and second connectors 92, 93, respectively. The articulation bands 96 and 97 have receptacles 98, 99 to couple the bands 96, 97 to the end effector 200 as will be discussed in further detail below.

Figure 3:
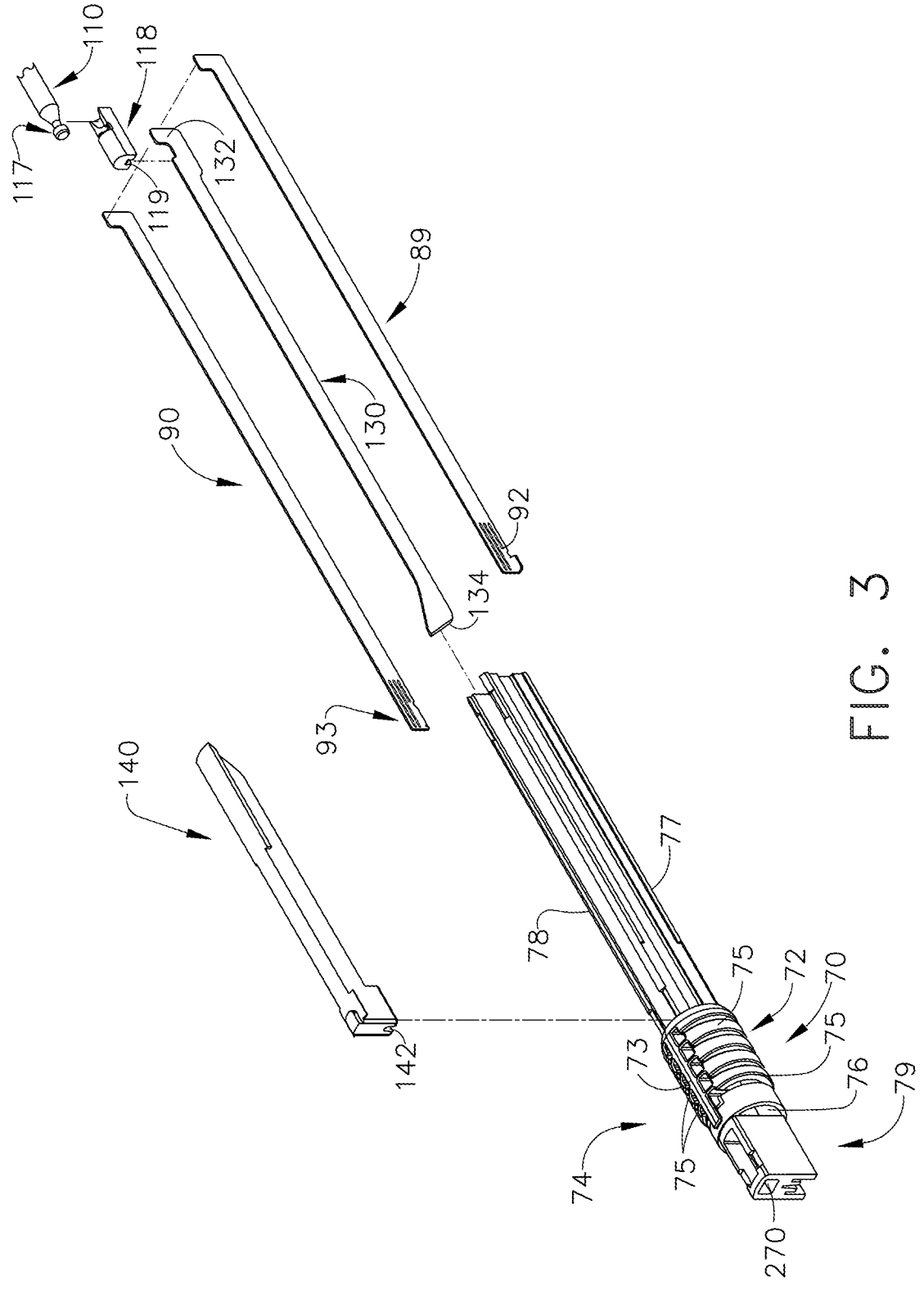
FIG. 3 is an exploded assembly view of a portion of an articulation assembly embodiment.

In at least one form, the flexible neck assembly 70 is preferably composed of a rigid thermoplastic polyurethane sold commercially as ISOPLAST grade 2510 by the Dow Chemical Company. As can be seen in FIG. 3, the flexible neck assembly 70 has first and second flexible neck portions 72, 74. These neck portions 72, 74 are separated by a central longitudinal rib 73. See FIG. 6. The neck portions 72, 74 each have a plurality of neck ribs 75 configured essentially as semi-circular disks. The flexible neck portions 72, 74 together generally form a cylindrical configuration. A side slot 76 extends through each of the neck ribs 75 to provide a passage through the first and second flexible neck portions 72, 74 for receiving the interior articulation bands 89, 90 and exterior reinforcement band portions 86, 87 of the flexible band assemblies 83, 85. In a similar fashion, the central longitudinal rib 73 separating the first and second flexible neck portions 72, 74 has a central longitudinal slot for providing a passage to receive the stapler actuating members. Extending proximally from the first and second flexible neck portions 72, 74 are first and second support guide surfaces 77, 78 for supporting the reciprocating movement of the interior articulation bands 89, 90 and the exterior reinforcement portions 86, 87 of the flexible transmission band assemblies 83, 85. Extending from the distal end of the flexible neck portions 72, 74 is a channel guide 79 for guiding the movement of the stapler actuating members into a staple cartridge 300 of the end effector 200 as will be further discussed below.

In at least one form, when the first and second transmission band assemblies 83, 85 are brought into contact with each other during assembly of the instrument 10, they form an elongate cylinder which has a longitudinal cavity through it that is concentrically positioned between the band assemblies 83, 85 for the passage of a firing rod 110. The proximal ends of the first and second bands have first and second gear racks 94, 95 which, as will be discussed below, meshingly engage an articulation assembly 62.

Figure 5:
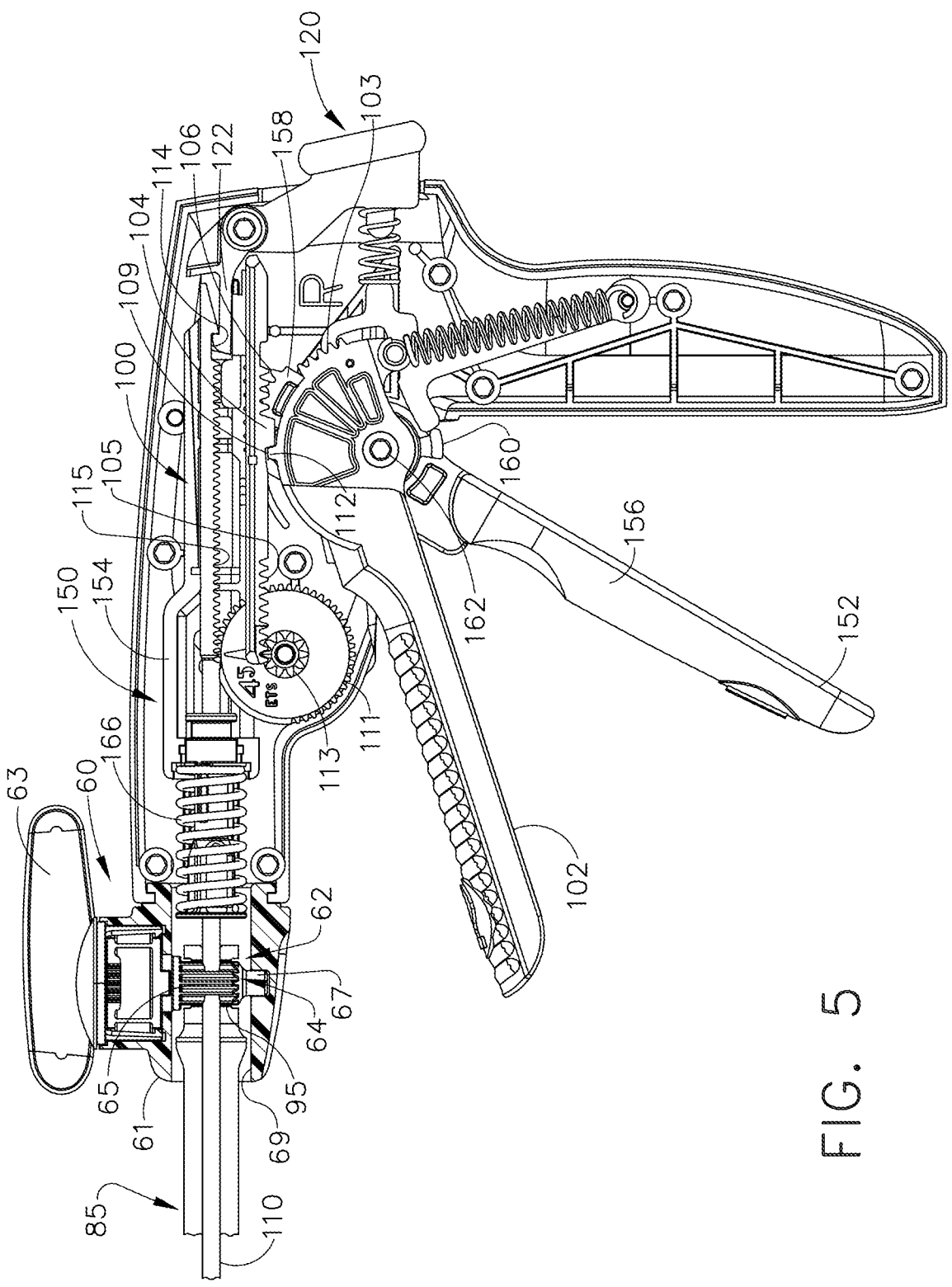
FIG. 5 is a side view of the handle with a handle case removed.

Upon rotation of the articulation assembly 62, one of the first and second flexible transmission band assemblies is moved forwardly and the other band assembly is moved rearwardly. In response to the reciprocating movement of the band assemblies 83, 85 within the first and second flexible neck portions 72, 74 of the flexible neck assembly 70, the flexible neck assembly 70 bends to provide articulation. As can be seen in FIG. 5, an articulation assembly 62 includes an actuator 63, an articulation body 64 and the nozzle 60.

Figure 4:
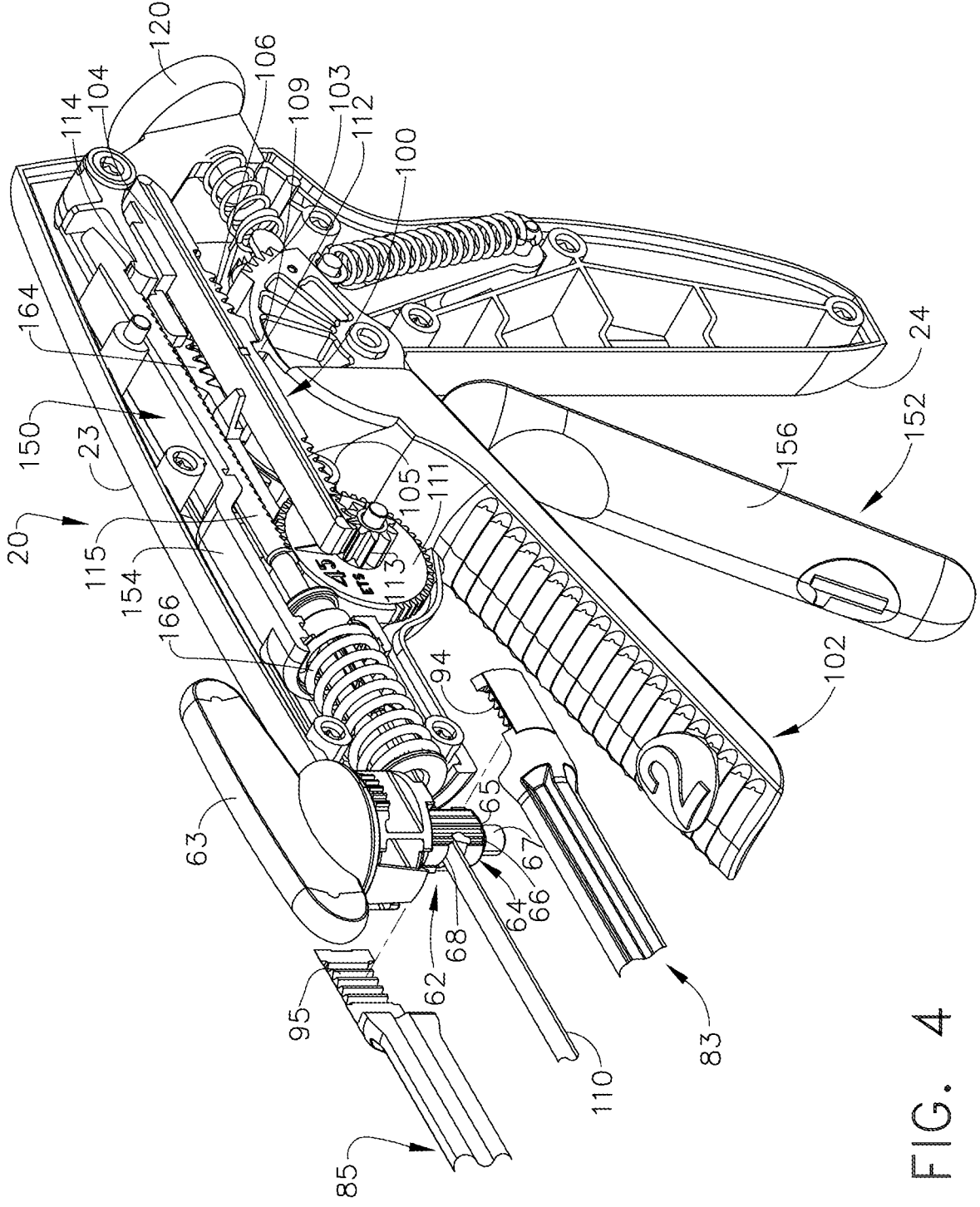
FIG. 4 is a partial exploded perspective view of a portion of the handle.

Rotational movement of the actuator 63 causes corresponding rotation of the articulation body 64 within the nozzle 60. The first and second elongate transmission band assemblies 83, 85, consequently reciprocate axially in opposite directions parallel to the longitudinal axis A-A of the endoscopic shaft 30 of the stapling device 10 to cause the remote articulation of the end effector 200 through the flexible neck assembly 70. The articulation body 64 further includes a drive gear 65 thereon. As can be seen in FIG. 4, the drive gear 65 has a flared opening 66 through it, and a lower pivot 67. Within the flared opening 66 of the drive gear 65, there is a firing rod orifice 68 for receiving the firing rod 110 enabling the firing of staples into the clamped tissue in response to pivotal rotation of the firing trigger 102. The drive gear 65 is supported for meshing engagement with the first and second drive racks 94, 95 on the flexible elongate transmission band assemblies 83, 85 to effect the desired reciprocating movement of the band assemblies 83, 85.

As can be seen in FIG. 5, the nozzle 60 of the articulation assembly 62 has a nozzle body 61. The nozzle body 61 has an axial bore 69 extending through it for receiving the drive gear 65 of the articulation body 64. The bore 69 provides a continuous opening axially from the frame into the elongate endoscopic shaft 30 and therefore the firing rod 110 and other operative components of the stapling device 10 can communicate with the end effector 200. Further details relating to the articulation assembly 62 may be found in U.S. Pat. No. 5,704,534, which has been previously herein incorporated by reference.

Closure System

Figures 24, 25:
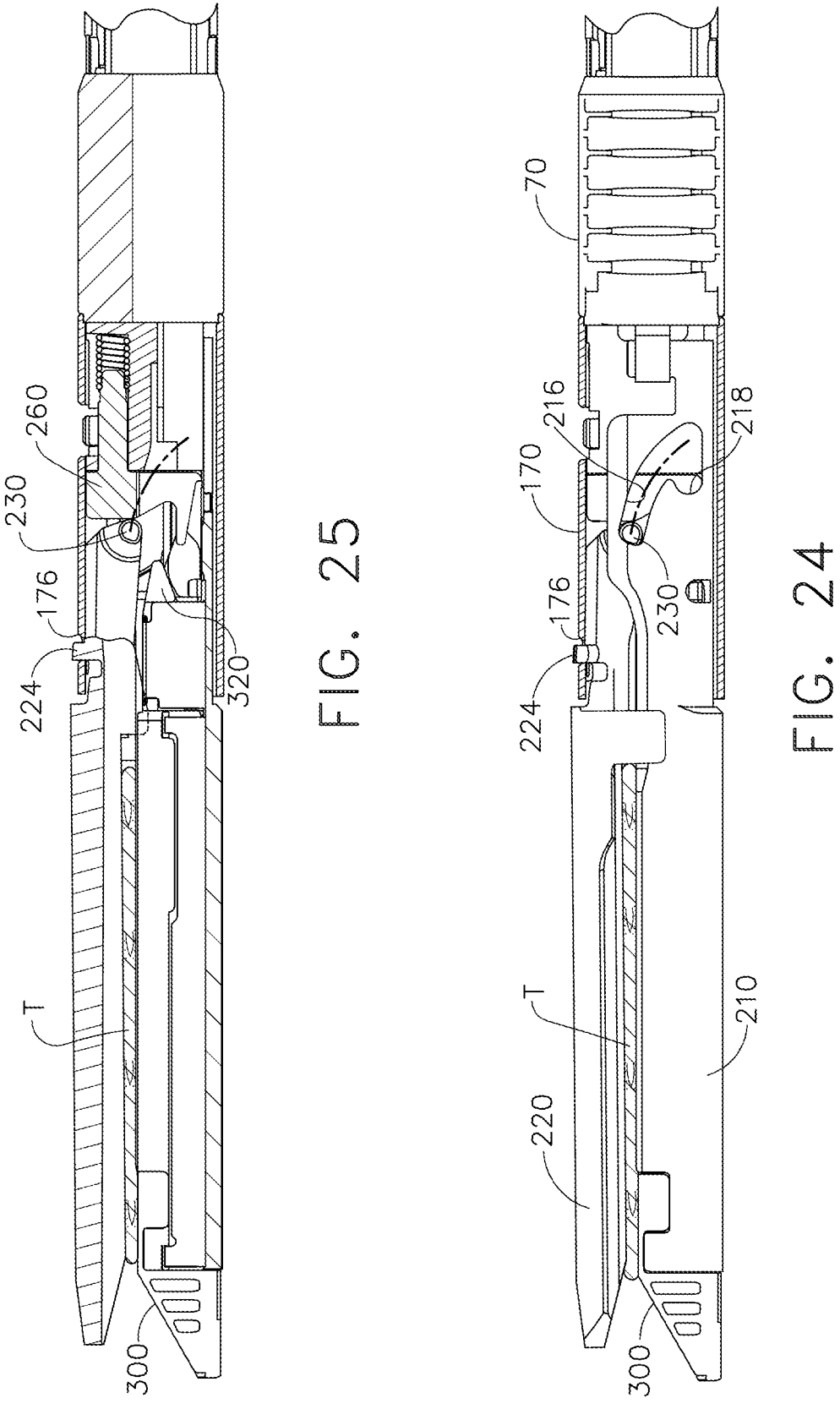
FIG. 24 is a side elevational view of the end effector of FIGS. 16-23 in a fully clamped position ready to fire.
FIG. 25 is a cross-sectional view of the end effector of FIG. 24.

As will be discussed in further detail below, the end effector 200 comprises an elongate channel 210 that is configured to operably receive a surgical staple cartridge 300. An anvil 220 is movably supported relative to the elongate channel 210 and is moved from an open position (FIGS. 16 and 17) to closed positions wherein tissue may be cut and stapled (FIGS. 24 and 25). The movement of the anvil 220 between open and closed positions is at least partially controlled by a closure system, generally designated as 150, which, as indicated above, is controlled by the closure trigger 152. The closure system 150 includes the proximal closure tube segment 151 that operably houses the articulation band assemblies 83, 85 in the manner discussed above and which is non-movably coupled to the flexible neck assembly 70.

In various forms, the proximal closure tube segment 151 includes a proximal end portion 153 that axially extends through the bore 69 in the nozzle 60. The proximal closure tube segment 151 has elongate axial slots 155 therethrough to permit the articulation body 64 to extend therethrough. See FIG. 2. The slots 155 enable the articulation body 64 to rotate about articulation axis B-B relative to the proximal closure tube segment 151 while facilitating the axial movement of the proximal closure tube segment 151 along axis A-A relative to articulation body 64. The transmission bands 83, 85 function as a frame upon which the proximal closure tube segment 151 can axially move. The proximal end 153 of the proximal closure tube segment 151 is rotatably coupled to a closure yoke 154 that is supported within the handle 20 for reciprocating motion therein. See FIGS. 4 and 5.

The closure trigger 152 has a handle section 156, a gear segment section 158 and an intermediate section 160. See FIG. 5. A bore extends through the intermediate section 160. A cylindrical support member 162 extending from the second handle housing 23 passes through the bore for pivotably mounting the closure trigger 152 on the handle portion 20. A proximal end 98 of the closure yoke 154 has a gear rack 164 that is engaged by the gear segment section 158 of the closure trigger 152. When the closure trigger 152 is moved toward the pistol grip 24 of the handle portion 20, the closure yoke 154 and, hence, the proximal closure tube segment 151 move distally, compressing a spring 166 that biases the closure yoke 152 proximally.

Figures 8, 9, 10:
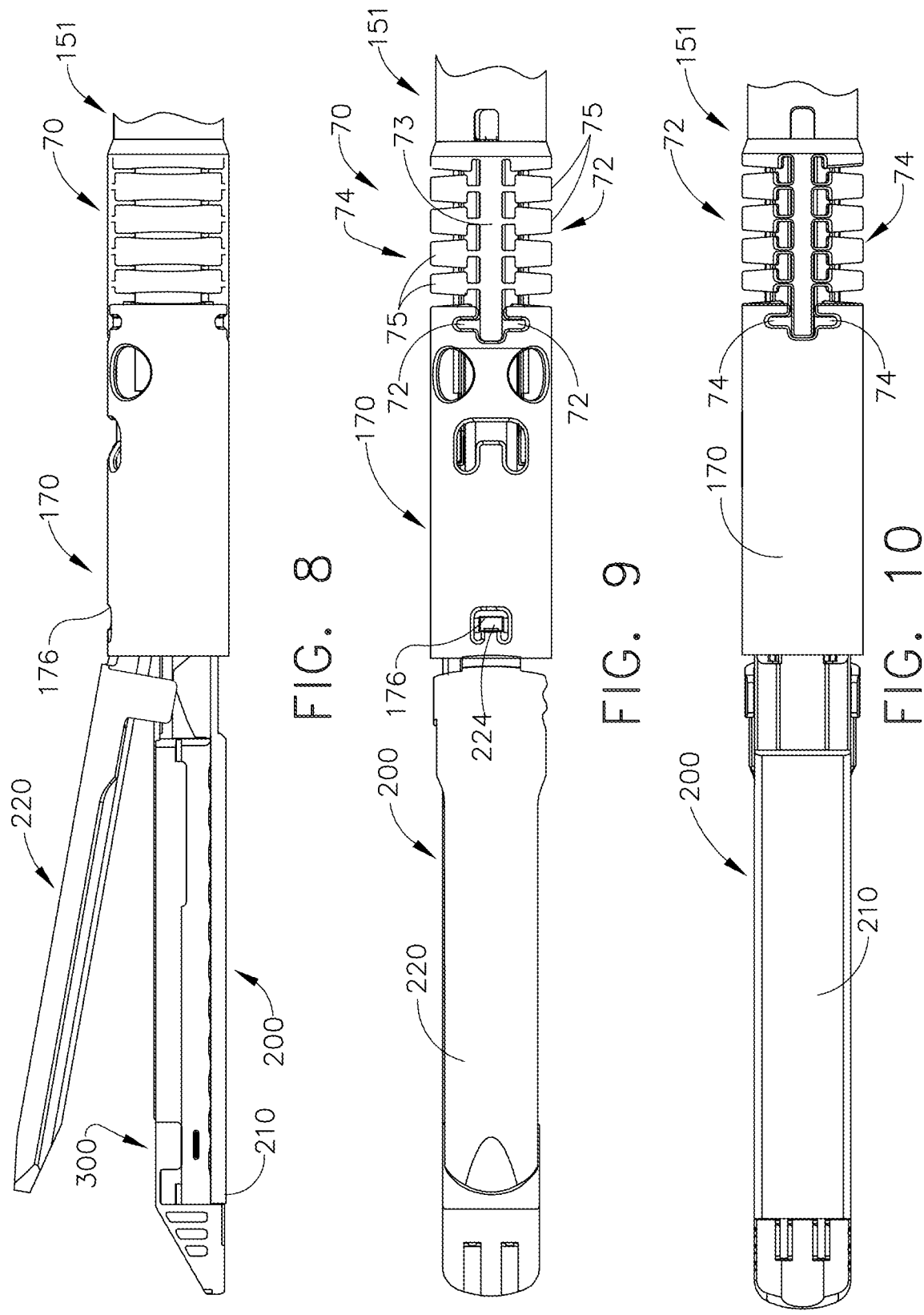
FIG. 8 is a side elevational view of an end effector embodiment in an open position.
FIG. 9 is a top view of the end effector of FIG. 8.
FIG. 10 is a bottom view of the end effector depicted in FIGS. 8 and 9.

In at least one form, the closure system 150 further includes a distal closure tube segment 170 that is non-movably coupled to the channel guide portion 79 of the flex neck assembly 70 by attachment tabs 72, 74. See FIGS. 9 and 10. The distal closure tube segment 170 has an opening 176 therein that is adapted to interface with an upstanding tab 224 formed on the anvil 220 as will be discussed in further detail below. Thus, axial movement of the proximal closure tube segment 151 results in axial movement of the flex neck assembly 70, as well as the distal closure tube segment 170. For example, distal movement of the proximal closure tube segment 151 effects pivotal translation movement of the anvil 220 distally and toward the elongate channel 210 of the end effector 200 and proximal movement effects opening of the anvil 220 as will be discussed in further detail below.

Firing System

In at least one form, the surgical instrument 10 further includes a firing system, generally designated as 100, for applying firing motions to the firing rod 110 in response to actuation of the firing trigger 102. In at least one form, the firing system 100 further includes a drive member 104 that has first and second gear racks 105, 106 thereon. A first notch 109 is provided on the drive member 105 intermediate the first and second gear racks 105, 106. During return movement of the firing trigger 102, a tooth 112 on the firing trigger 102 engages with the first notch 109 for returning the drive member 104 to its initial position after staple firing. A second notch 114 is located at a proximal end of the firing rod 110 for locking the firing rod 110 to an upper latch arm 122 of the release button 120 in its unfired position. The firing system 150 further includes first and second integral pinion gears 111, 113. The first integral pinion gear 111 is engaged with a drive rack 115 provided on the firing rod 110. The second integral pinion gear 113 is engaged with the first gear rack 105 on the drive member 104. The first integral pinion gear 111 has a first diameter and the second integral pinion gear 113 has a second diameter which is smaller than the first diameter.

In various embodiments, the firing trigger 102 is provided with a gear segment section 103. The gear segment section 103 engages the second gear rack 106 on the drive member 104 such that motion of the firing trigger 102 causes the drive member 104 to move back and forth between first and second drive positions. In order to prevent staple firing before tissue clamping has occurred, the upper latch arm 122 on the release button 120 is engaged with the second notch 114 on the drive rack 115 such that the firing rod 110 is locked in its proximal-most position. When the upper latch arm 122 falls into a recess in the closure yoke, the upper latch arm 122 disengages with the second notch 114 to permit distal movement of the firing rod 110. Because the first gear rack 105 on the drive member 104 and the drive rack 115 on the firing rod 110 are engaged, movement of the firing trigger 102 causes the firing rod 110 to reciprocate between a first reciprocating position and a second reciprocating position. Further details concerning various aspects of the firing system 150 may be gleaned from reference to U.S. Pat. No. 7,000,818 which has been herein incorporated by reference in its entirety.

As can be seen in FIG. 3, various embodiments, the distal end 117 of the firing rod 110 is rotatably received within a firing bar mounting yoke 118. The firing bar mounting yoke 118 has a slot 119 for hookingly receiving a hook 132 formed on a proximal end of a knife bar 130. In addition, as shown in FIG. 3, a support bar 140 is supported for axial movement between the first and second support guide surfaces 77, 78 of the flex neck assembly 70. The support bar 140 has a slot 142 that is configured to permit the knife bar 130 to slidably pass therethrough. The metal knife bar 130 has a tissue cutting edge 134 formed on its distal end and is configured to operably interface with a wedge sled operably supported within a surgical staple cartridge 300.

End Effector

Figures 6, 7:
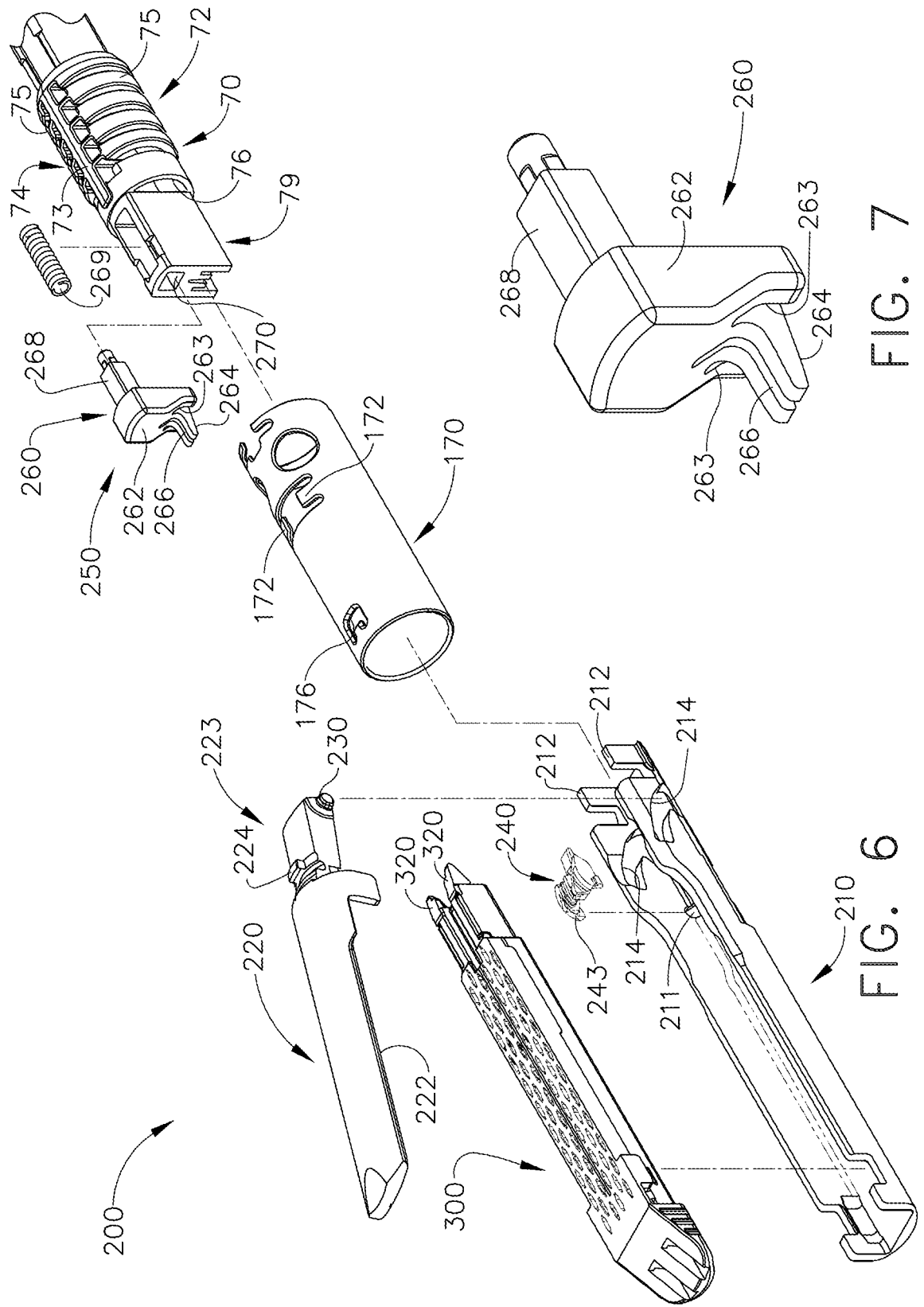
FIG. 6 is a partial exploded perspective view of an end effector and anvil lock embodiment.
FIG. 7 is a perspective view of an anvil lock member embodiment.
Figure 11:
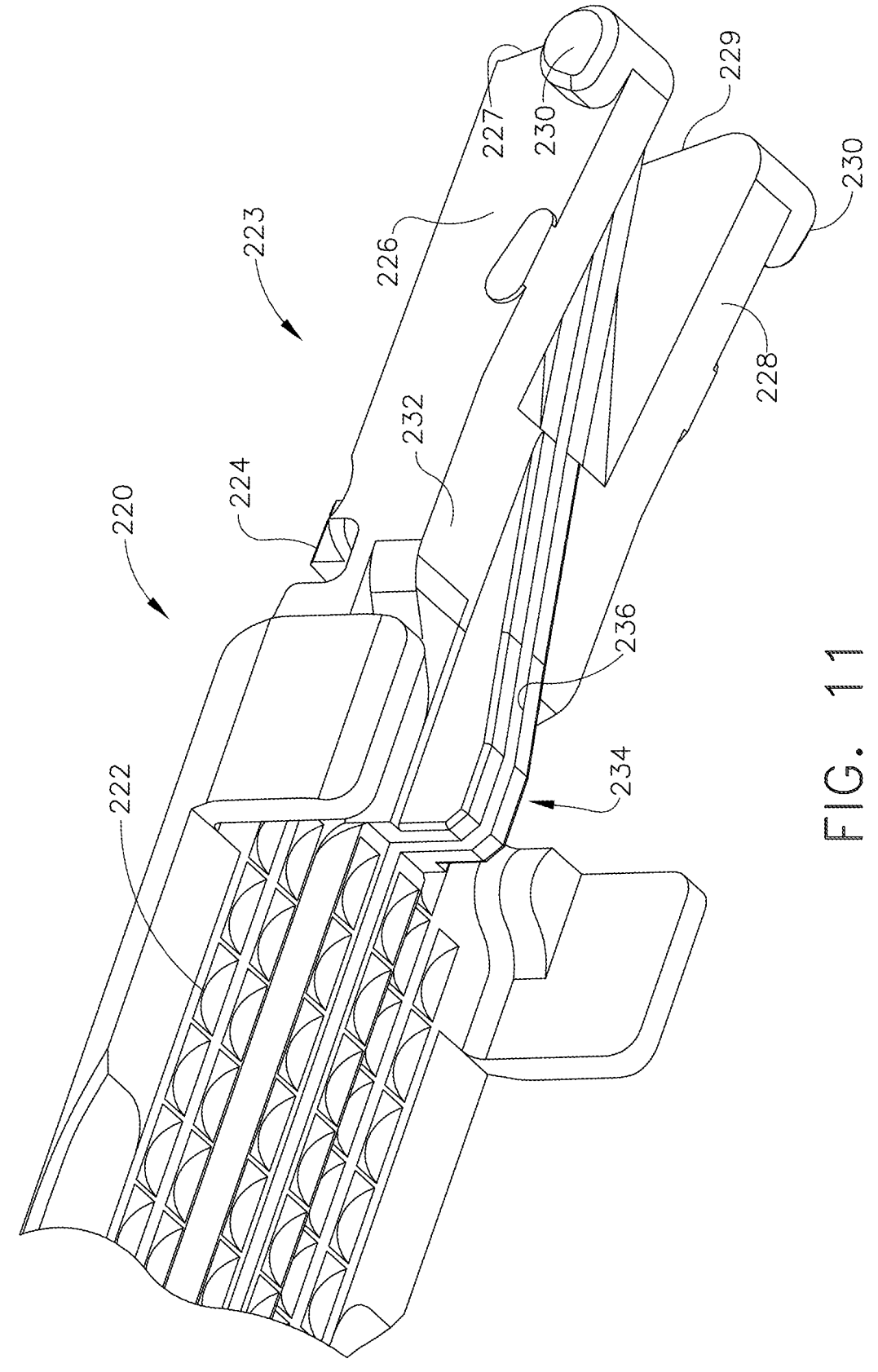
FIG. 11 is a partial bottom perspective view of an anvil embodiment.

As discussed above, in at least one form, an end effector 200 includes an elongate channel 210 that is configured to operably support a surgical staple cartridge 300 therein. As shown in FIGS. 2 and 6, the elongate channel 210 has a proximal end portion that includes two spaced mounting tabs 212 that are configured to be engaged by the hooks 998, 99 on the distal ends of the articulation bands 96, 97. Thus, the reciprocating motions of the articulation bands 96, 97 cause the elongate channel 210 to articulate relative to the flex neck assembly 70. As further indicated above, the end effector 200 also includes an anvil 220. In at least one form, the anvil 220 is fabricated from, for example, 416 Stainless Steel Hardened and Tempered RC35 (or similar material) and has a staple-forming undersurface 222 thereon that is configured for confronting engagement with the staple cartridge 300 when mounted in the elongate channel 210. The anvil 220 is formed with a proximally extending mounting portion 223 that includes two trunnion walls 226, 228 that each has a trunnion 30 protruding therefrom. See FIG. 11. In addition, formed on the underside 232 of the mounting portion 223 is a downwardly protruding pivot tab 234 that has a slot 236 extending therethrough that is configured to receive and support the knife bar 130 as it is axially advanced through the end effector 200 during cutting and stapling. In addition, the anvil opening tab 224 is formed on the mounting portion 223 such that it can operably interface with the opening 176 in the distal closure tube segment 170 as will be further discussed below. As can be seen in FIGS. 16-25, the anvil trunnions 230 are configured to be movably received in corresponding trunnion slots 214 formed in the proximal end of the elongate channel 210. Each trunnion slot 214 has an arcuate segment 216 that communicates with a locking notch 218.

Figures 12, 13:
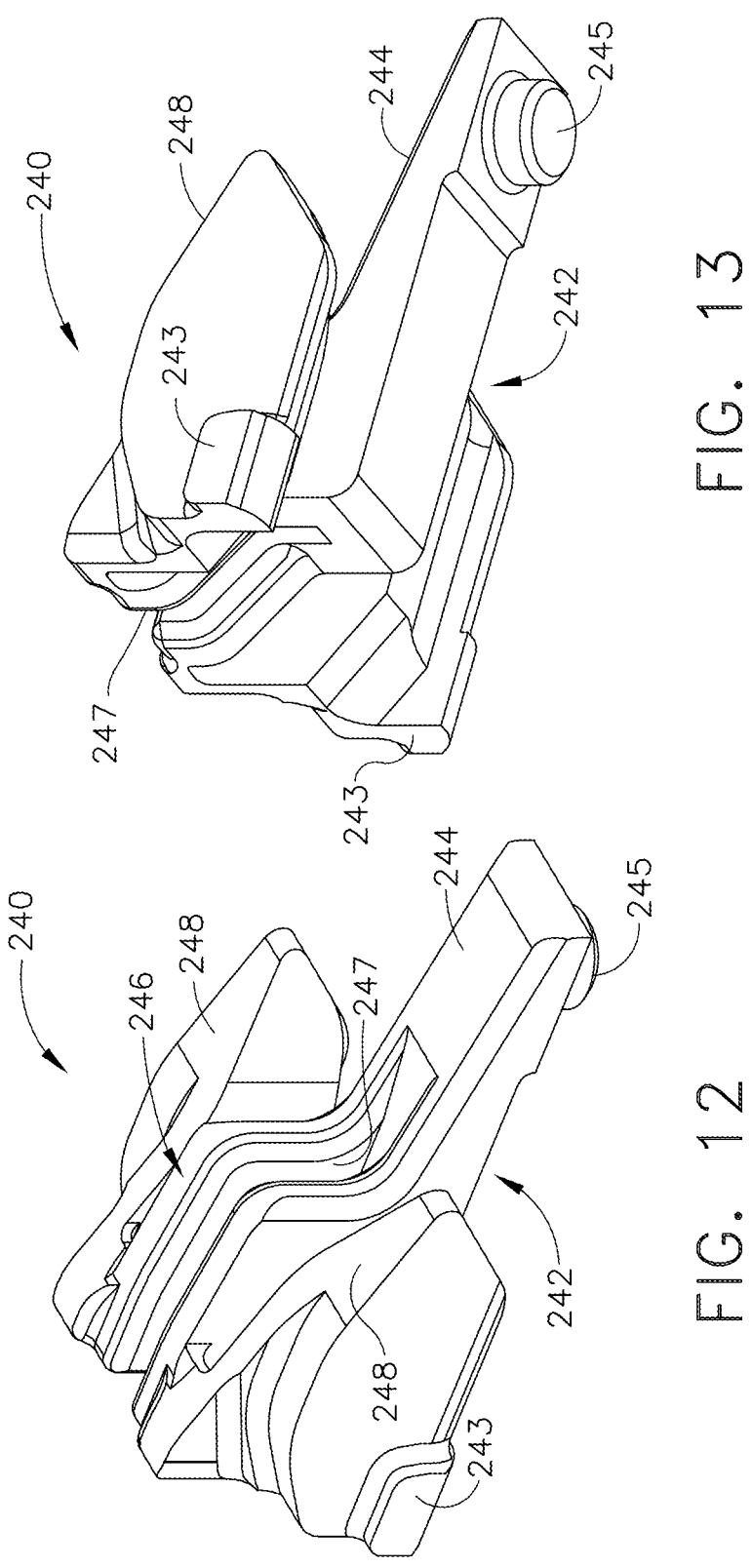
FIG. 12 is a perspective view of a pivot mount embodiment.
FIG. 13 is a bottom perspective view of the pivot mount embodiment of FIG. 12.

To facilitate pivotal travel of the anvil mounting portion 223 relative to the elongate channel 210, various embodiments include a pivot mount 240. As can be in FIGS. 12 and 13, one form of a pivot mount 240 has a body portion 242 that is configured to be attached to the elongate channel 210. For example, the body portion 242 may be formed with two opposed attachment tabs 243 that are configured to retainingly engage tab openings 211 (FIG. 6) formed in the elongate channel 210. In addition, the pivot mount 240 has a proximally extending foot portion 244 that has a retainer lug 245 protruding therefrom that is configured to be received in a corresponding opening 211 in the elongate channel 210. See FIG. 17. The pivot mount 240 may be fabricated from, for example, Vectra A435 Liquid Crystal Polymer—natural or similar materials. As can be further seen in FIGS. 12 and 13, the body portion 242 has an upstanding central portion 246 that has a slot 247 extending therethrough for axially receiving the knife bar 130. The central portion 246 provides lateral support to the knife bar 130 as it is driven through tissue clamped within the end effector 200. Various embodiments of the pivot mount 240 further include rocker surfaces 248 formed on each side of the central portion 246 for pivotally receiving the trunnion walls 226, 228 of the anvil 220 thereon.

Anvil Lockout System

Various embodiments include a unique and novel anvil lockout system 250 that prevents closure of the anvil 220 when a staple cartridge 300 has not been properly installed in the elongate channel 210. Referring to FIGS. 6 and 7, for example, an embodiment of an anvil lockout system 250 includes a movable anvil lock member 260 that is movable in response to contact by a portion or portions of a staple cartridge 300 as will be discussed in further detail below. In at least one form, the anvil lock member 260 comprises a body portion 262 that has a distally protruding central support tab 264 formed thereon. A slot 266 extends through body portion 262 and the central support tab 264 to enable the knife bar 130 to pass therethrough. The body portion 262 further includes proximally extending mounting bar 268 that is configured to be slidably received within a corresponding mounting opening 270 in the channel guide 79 of the flex neck assembly 70. In addition, a biasing member in the form of, for example, a coil spring 269 is supported within the opening 270 to bias the anvil lock member 260 in the distal direction "DD". See FIG. 16. When the anvil 220 is mounted to the elongate channel 210, the trunnions 230 are received within their corresponding trunnion slots 214 in the elongate channel 210, the central support tab 264 of the anvil lock member 260 is received between the trunnion walls 226, 228 to further provide support to the anvil 220. The body portion 262 of the anvil lock member 260 is further formed with two cam surfaces 263 configured to engage the proximal end surfaces 227, 229 of the trunnion walls 226, 228. See FIGS. 6 and 7. Various embodiments of the anvil lock member may be fabricated from, for example, Vectra A435 Liquid Crystal Polymer—natural or similar materials.

Figures 6A, 7A:
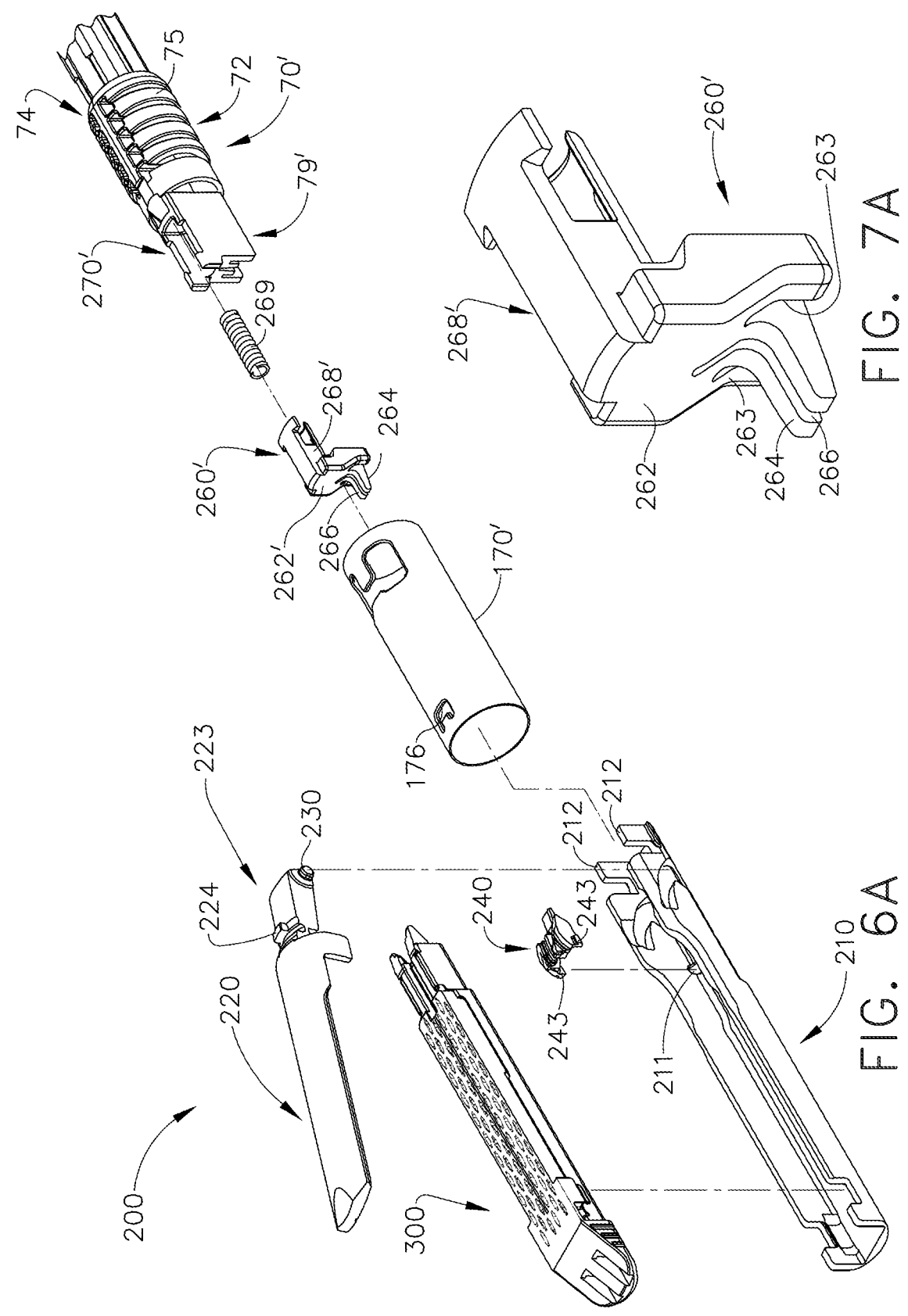
FIG. 6A is a partial exploded perspective view of another end effector and anvil lock member embodiment.
FIG. 7A is a perspective view of an anvil lock member embodiment of FIG. 6A.

FIGS. 6A and 7A illustrate an alternative anvil lock member 260' that is movable in response to contact by a portion or portions of a staple cartridge 300. In at least one form, the anvil lock member 260' comprises a body portion 262 that has a distally protruding central support tab 264 formed thereon. A slot 266 extends through body portion 262 and the central support tab 264 to enable the knife bar 130 to pass therethrough. The body portion 262 further includes proximally extending mounting bar 268' that is configured to be slidably and retainably received within a corresponding mounting opening 270' in the channel guide 79' of the flex neck assembly 70'. In addition, a biasing member in the form of, for example, a coil spring 269 is supported within the opening 270' to bias the anvil lock member 260' in the distal direction "DD". The anvil lock member 260' otherwise operates in the same manner as anvil lock member 260. When the anvil 220 is mounted to the elongate channel 210, the trunnions 230 are received within their corresponding trunnion slots 214 in the elongate channel 210, the central support tab 264 of the anvil lock member 260' is received between the trunnion walls 226, 228 to further provide support to the anvil 220. The body portion 262 of the anvil lock member 260 is further formed with two cam surfaces 263 configured to engage the proximal end surfaces 227, 229 of the trunnion walls 226, 228. The distal closure tube segment 170' operates in the same manner as the distal closure tube segment 170 described above.

Surgical Staple Cartridge

Figures 14, 15:
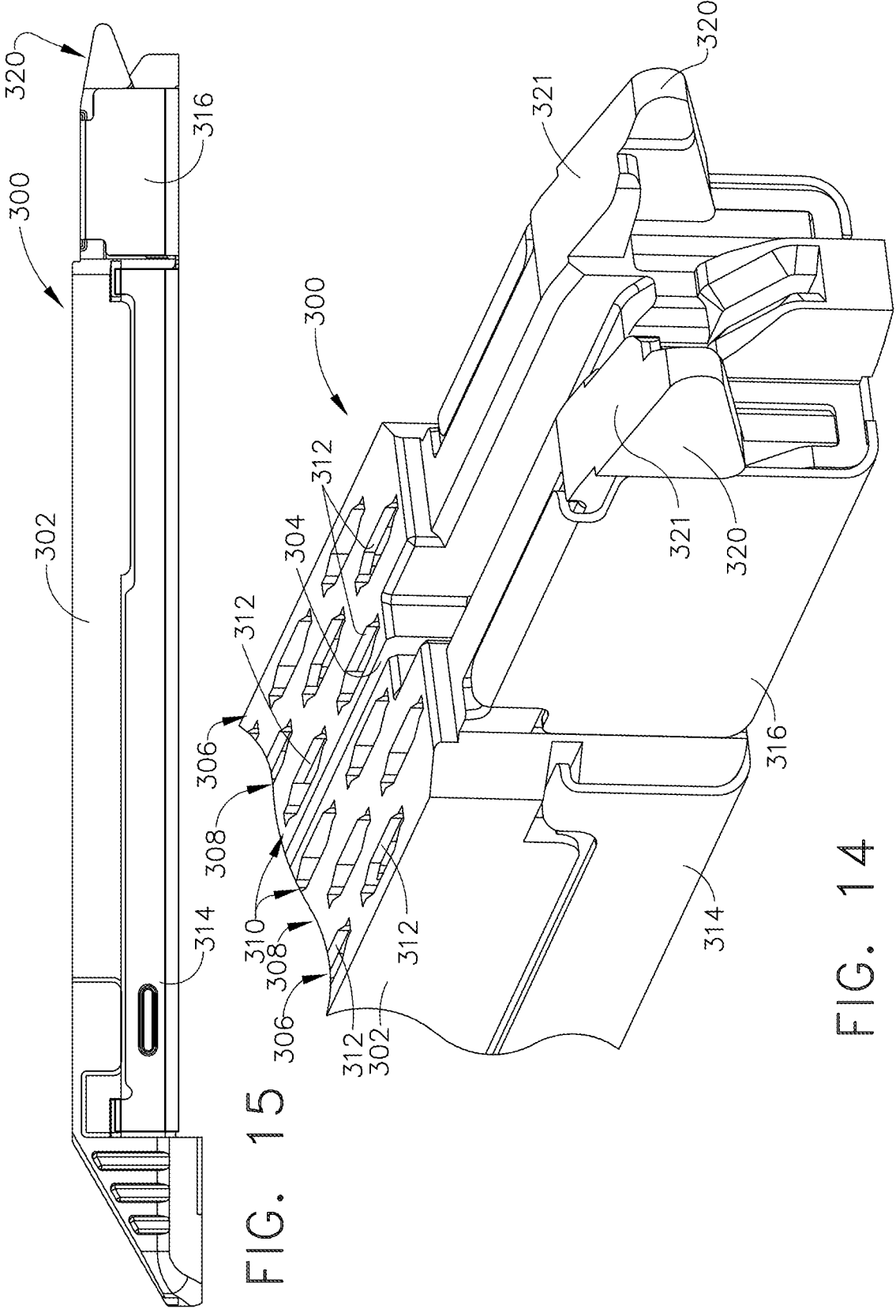
FIG. 14 is a perspective view of a proximal end portion of a surgical staple cartridge embodiment.
FIG. 15 is a side elevational view of the surgical staple cartridge embodiment depicted in FIG. 14.

Various embodiments include a unique and novel surgical staple cartridge 300 that is configured to interact with the anvil lockout system 250 when installed in the elongate channel 210. As can be seen in FIGS. 14 and 15, in at least one form, the surgical staple cartridge 300 includes a cartridge body 302 that may be fabricated from, for example, Vectra A435, 20% PTFE/15% GF-natural. The cartridge body 302 is sized and shaped to be received within the elongate channel 210. In at least one form, the cartridge body 302 is configured to be seated in the elongate channel 210 such that is removably retained therein. The cartridge body 302 may be formed with a centrally disposed slot 304 therein for receiving the knife bar 130. On each side of the slot 304, there is provided rows 306, 308, 310 of staple openings 312 that are configured to support a surgical staple therein. In the depicted embodiment, three rows 306, 308, 310 are provided on each side of the slot 304. The surgical staples may be supported on staple drivers that are movably supported within the staple openings 312. Also supported within the staple cartridge body 302 is a wedge sled that is configured for axial movement through the cartridge body 302 when contacted by the cutting bar. The wedge sled is configured with wedge-shaped driving members that contact the staple drivers and drive the drivers and their corresponding staples toward the closed anvil as the wedge sled is driven distally through the cartridge body 302. Examples of staple driver arrangements and wedge sled arrangements that may be employed are described in further detail in U.S. Pat. No. 7,669,746, the entire disclosure which is herein incorporated by reference. In various embodiments, to facilitate installation of the wedge sled and drivers in the cartridge body 302, metal cartridge pans 314, 316 may be attached to the cartridge body 302 as shown in FIGS. 14 and 15. The cartridge pans 314 and 316 serve to retain the wedge sled and drivers within the cartridge body 302.

In various embodiments, the cartridge body 302 additionally has at least one release member formed thereon that protrudes in the proximal direction. In the embodiment depicted in FIG. 14, two release members 320 are formed on the proximal end 319 of the cartridge 300. The release members 320 each have a wedge shape that defines a sloped pivot surface 321 that are configured to pivotally support a portion of the anvil mounting portion 223 thereon.

Installation of a Staple Cartridge

Figures 16, 17:
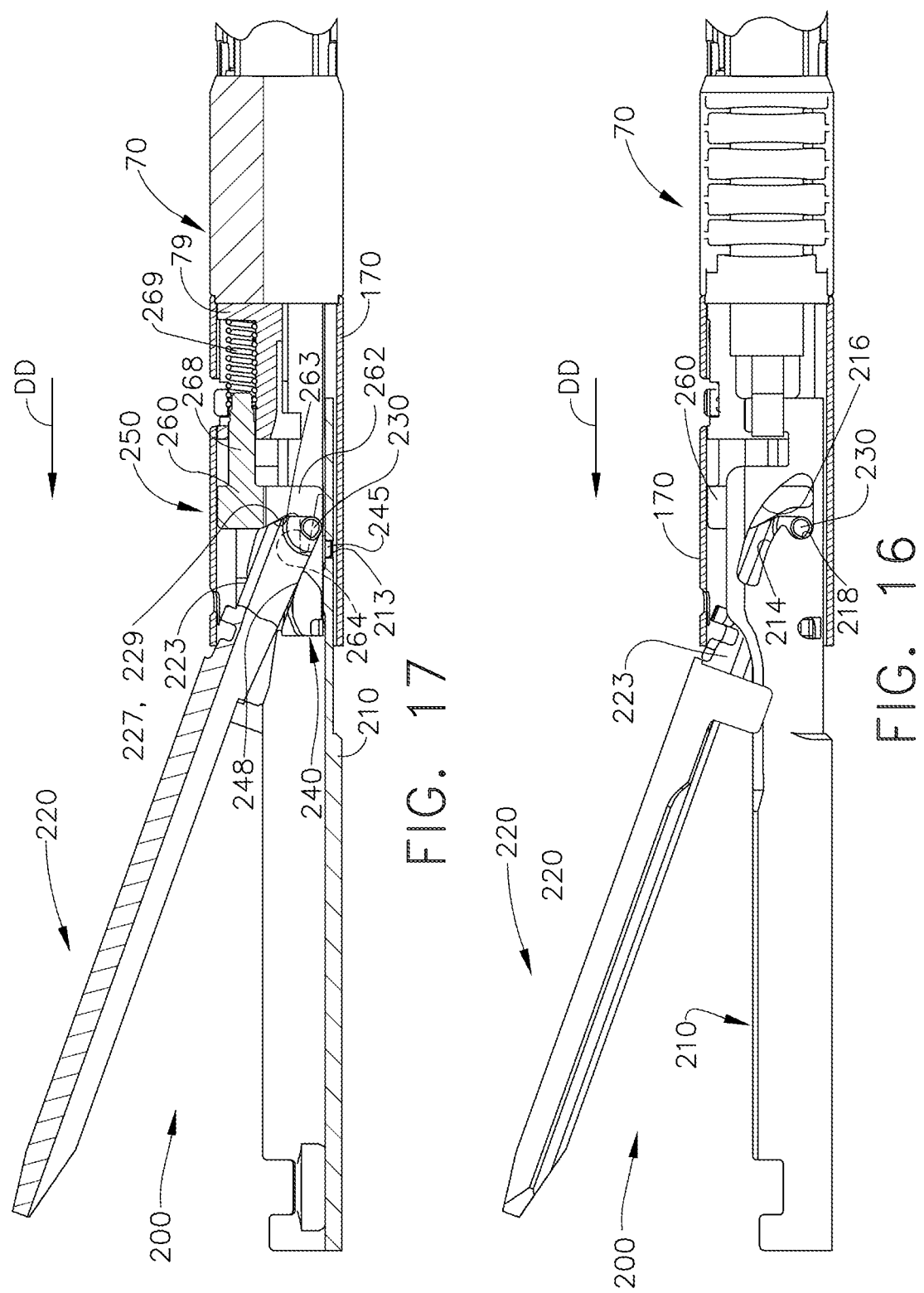
FIG. 16 is a side view of an end effector embodiment prior to seating a staple cartridge in the elongate channel.
FIG. 17 is a cross-sectional view of the end effector depicted in FIG. 16.

An understanding of the operation of a anvil lockout system may be gleaned from reference to FIGS. 16-25. FIGS. 16 and 17 illustrate the position of the anvil 220 relative to the elongate channel 210 prior to installing a staple cartridge 300. When in that "unloaded" and open position, the anvil lock member 260 is biased in the distal direction by spring 269 such that the cam surfaces 263 on the anvil lock member 260 are in contact with the end surfaces 227, 229 of the trunnion walls 226, 228. The anvil lock member 260 pushes the anvil mounting portion 223 in the distal direction "DD" such that the trunnions 230 are seated in their respective locking notch 218. The cam surfaces 263 on the anvil lock member 260, in cooperation with the end wall surfaces 227, 229, also serve to pivot and retain the anvil in the open position as shown in FIGS. 16 and 17. As can be seen in FIG. 16, when in that position, the trunnion walls 226, 228 are supported on the rocker surfaces 248 on the pivot mount 240. When in that position, the surgeon cannot close the anvil 220 by actuating the closure trigger 152 to advance the distal closure tube 170. Because the closure tube segments cannot be advanced distally to close the anvil 220, the closure trigger 152 cannot be actuated to its fully closed position whereby the firing trigger 102 may be actuated. Thus, when no cartridge 300 is present, the end effector 200 may not be actuated.

Figures 20, 21:
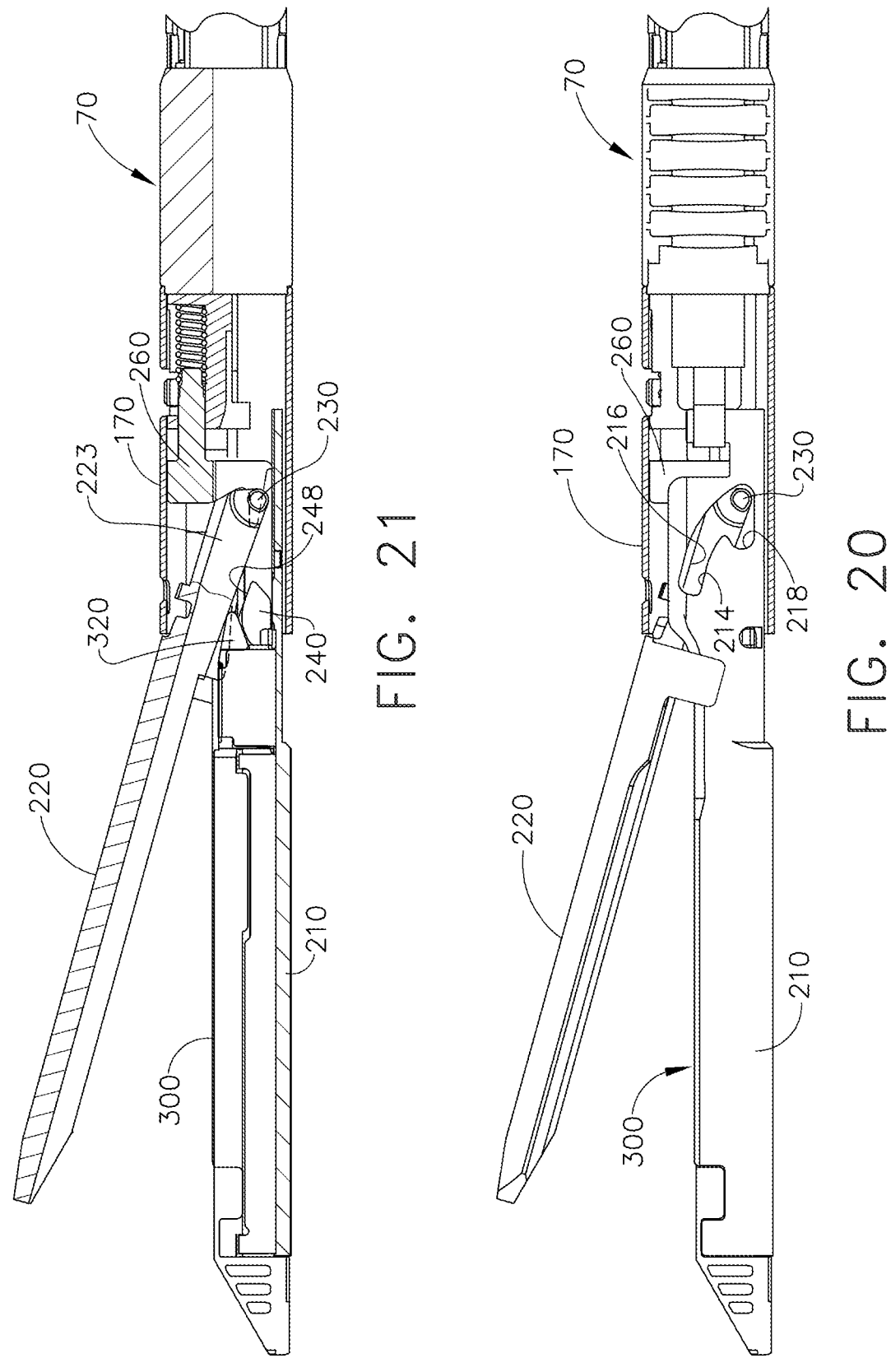
FIG. 20 is a side view of the end effector of FIGS. 16-19 with the staple cartridge embodiment seated within the elongate channel.
FIG. 21 is a cross-sectional view of the end effector of FIG. 20.

FIGS. 18 and 19 illustrate the initial insertion of the staple cartridge 300 into the elongate channel 210. FIGS. 20 and 21 illustrate the end effector 200 after the staple cartridge 300 has been fully seated in the elongate channel 210. As can be seen in FIG. 20 for example, when the cartridge 300 has been fully seated, the release members 320 on the cartridge 300 engage the trunnion walls 226, 228 and serve to move the anvil mounting portion 223 in a proximal direction "PD" such that the trunnion walls 226, 228 now pivotally rest on the release members 320. As can be seen in FIG. 21, when in that position, the anvil mounting portion 223 has moved proximally such that the trunnions 230 are moved out of their respective locking notches 218 and into the bottom of the arcuate slot segment 216 into an "actuatable" position whereby the anvil 220 may be pivoted closed by actuating the closure trigger 152.

Figures 22, 23:
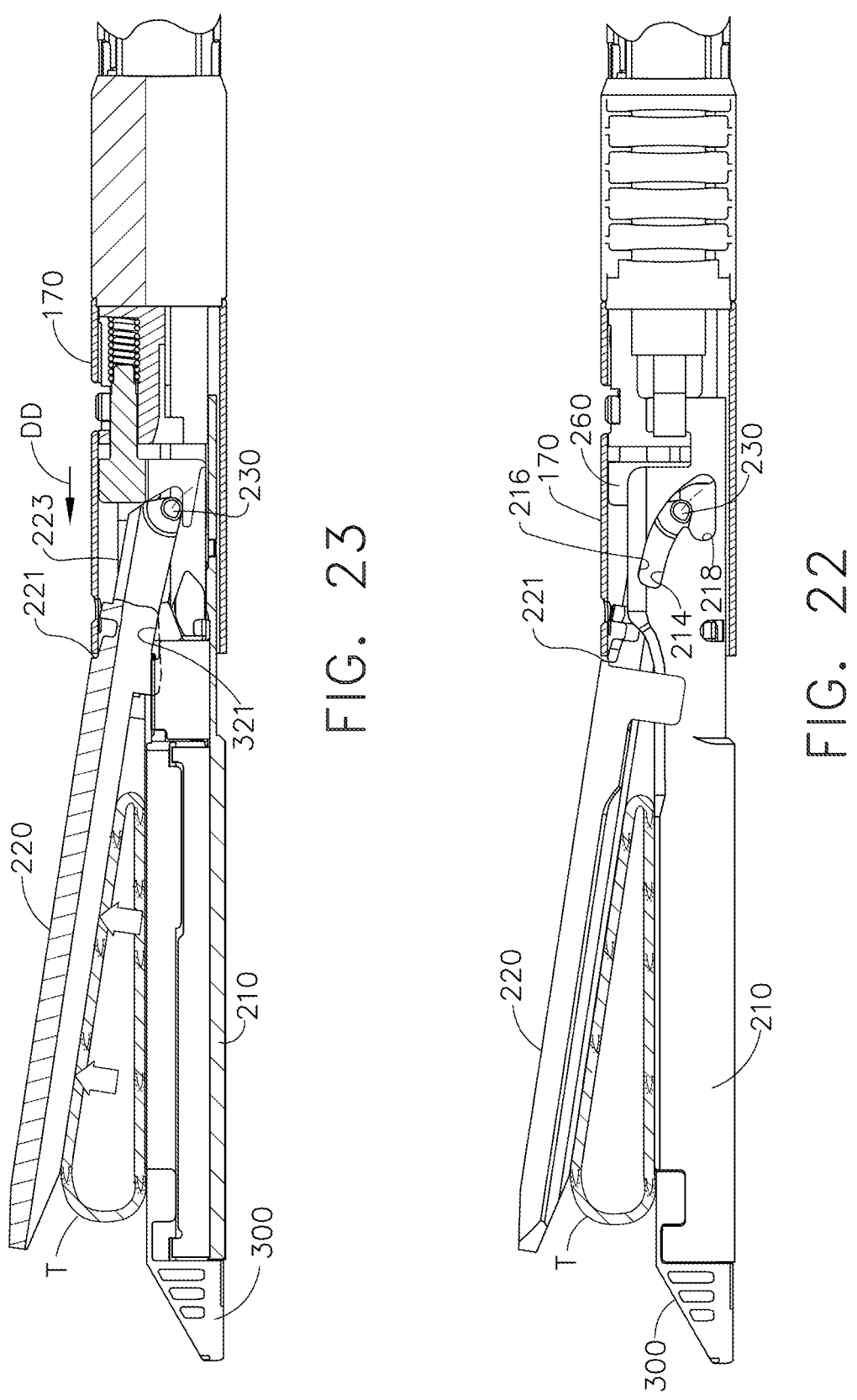
FIG. 22 is a side elevational view of the end effector of FIGS. 16-22 clamping tissue.
FIG. 23 is a cross-sectional view of the end effector of FIG. 22.

When the device 10 is in the starting position and the staple cartridge 300 has been loaded into the elongate channel as described above, both of the triggers 152, 102 are forward and the anvil 220 has been moved to the actuatable position, such as would be typical after inserting the loaded end effector 200 through a trocar or other opening into a body cavity. The instrument 10 is then manipulated by the clinician such that tissue "T" to be stapled and severed is positioned between the staple cartridge 300 and the anvil 200, as depicted in FIGS. 22 and 23. As discussed above, movement of the closure trigger 152 toward the pistol grip 24 causes the proximal closure tube segment 151, the flex neck assembly 70 and the distal closure tube segment 170 to move distally. As the distal closure tube segment 170 moves distally, it contacts a closure ledge 221 on the anvil 220. Pressure from the tissue captured between the anvil 220 and the staple cartridge 300 serves to move the anvil 220 such that the trunnions 230 are positioned to move within the arcuate trunnion slot segments 216. The surgeon may pivot the anvil 220 relative to the staple cartridge 300 to manipulate and capture the desired tissue "T" in the end effector 200. As the distal closure tube segment 170 contacts the closure ledge 221, the anvil 220 is pivoted towards a clamped position. The retracted knife bar 130 does not impede the selective opening and closing of the anvil 220.

Once the desired tissue "T" has been positioned between the anvil 220 and the cartridge 300, the clinician moves the closure trigger 152 proximally until positioned directly adjacent to the pistol grip 24, locking the handle 20 into the closed and clamped position. As can be seen in FIG. 25, when in the fully clamped position, the anvil trunnions 230 are located in the upper end of the arcuate slot portion 216 and the anvil tab 224 is received within the opening 176 in the distal closure tube segment 170. After tissue clamping has occurred, the clinician moves the firing trigger 102 proximally causing the knife bar 130 to move distally into the end effector 200. In particular, the knife bar 130 moves through the slot 236 in the pivot tab portion 234 of the anvil 220 and into the slot 304 in the cartridge body 302 to contact the wedge sled operably positioned within the staple cartridge 300. As the knife bar 130 is driven distally, it cuts the tissue T and drives the wedge sled distally which causes the staples to be sequentially fired into forming contact with the staple-forming undersurface 222 of the anvil 220. The clinician continues moving the firing trigger 102 until brought proximal to the closure trigger 152 and pistol grip 24. Thereby, all of the ends of the staples are bent over as a result of their engagement with the anvil 220. The cutting edge 132 has traversed completely through the tissue T. The process is complete by releasing the firing trigger 102 and by then depressing the release button 120 while simultaneously squeezing the closure trigger 152. Such action results in the movement of the distal closure tube segment 170 in the proximal direction "D". As the anvil tab 224 is engaged by the opening 176 in the distal closure tube segment 170 it causes the anvil to pivot open. The end surfaces 227, 229 again contact the pusher surfaces 263 on the anvil lock member 260 to pivot the anvil to the open position shown in FIGS. 20 and 21 to enable the spent cartridge 300 to be removed from the elongate channel 210.

Figure 26:
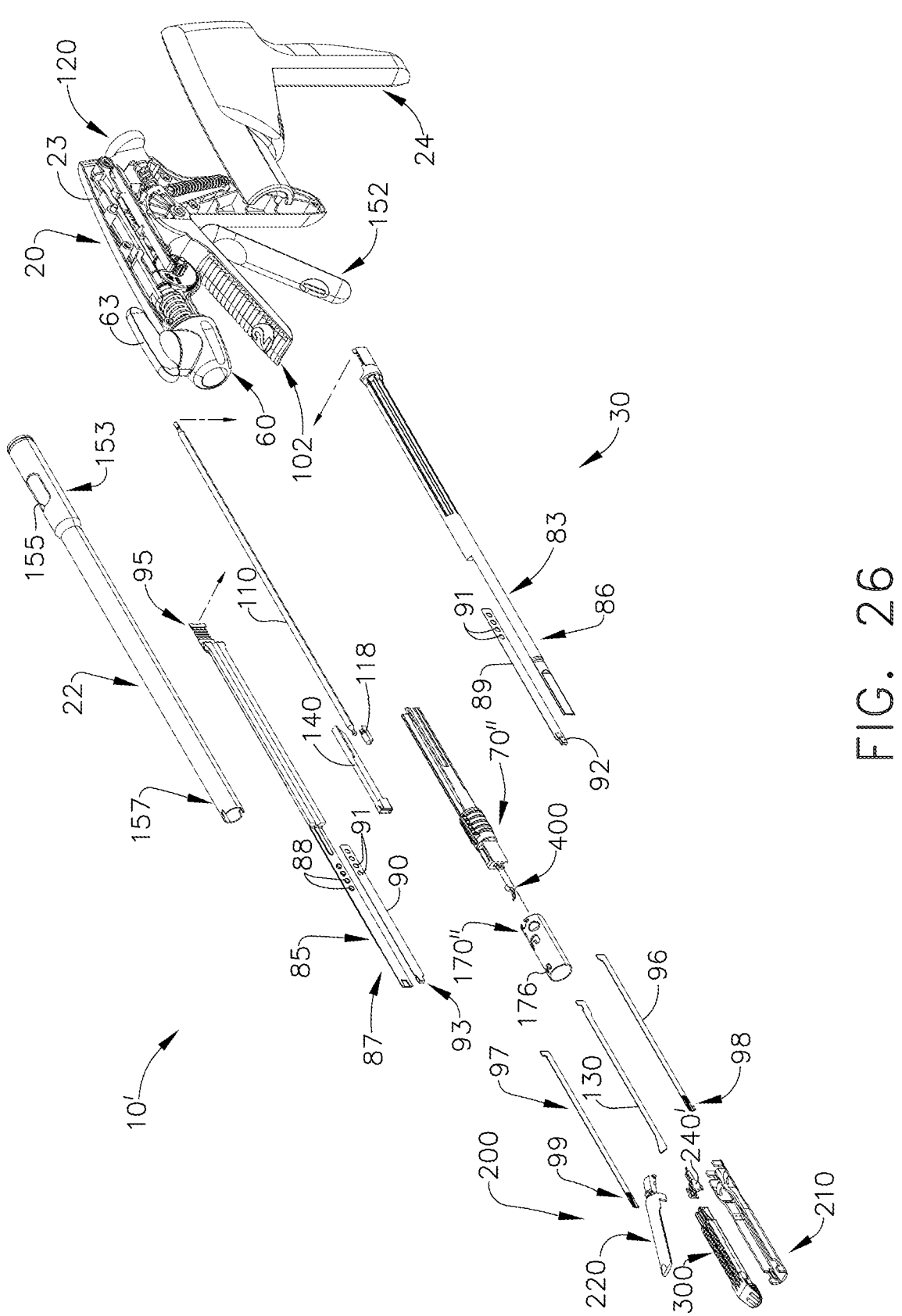
FIG. 26 is an exploded assembly view of another surgical stapling instrument embodiment.
Figures 27, 28:
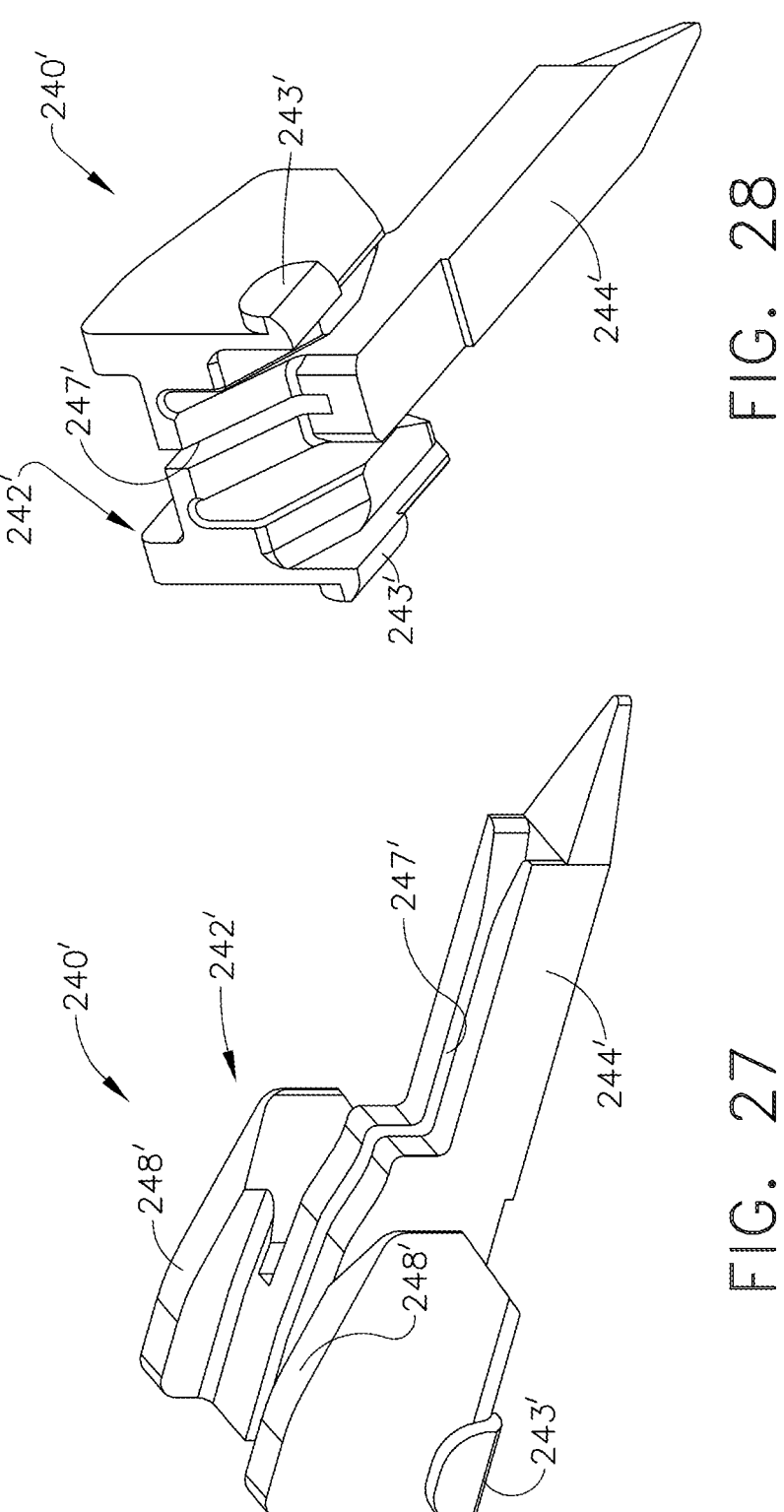
FIG. 27 is a perspective view of another pivot mount embodiment.
FIG. 28 is a bottom perspective view of the pivot mount embodiment of FIG. 27.

FIGS. 26-42 illustrate an alternative surgical stapling instrument 10' that is similar in construction and operation to surgical stapling instrument 10 except for the differences discussed below. This embodiment, for example, employs the pivot mount 240' illustrated in FIGS. 29 and 30. As can be seen in FIGS. 27 and 28 one form of a pivot mount 240' has a body portion 242' that is configured to be attached to the elongate channel 210. For example, the body portion 242' may be formed with two opposed attachment tabs 243' that are configured to retainingly engage tab openings 211 (FIG. 26) formed in the elongate channel 210. In addition, the pivot mount 240' has a proximally extending foot portion 244' that has a slot 247' extending therethrough for axially receiving the knife bar 130. Various embodiments of the pivot mount 240' further include rocker surfaces 248' formed on the body portion 242' for pivotally receiving the trunnion walls 226, 228 of the anvil 220 thereon.

Figures 29, 30:
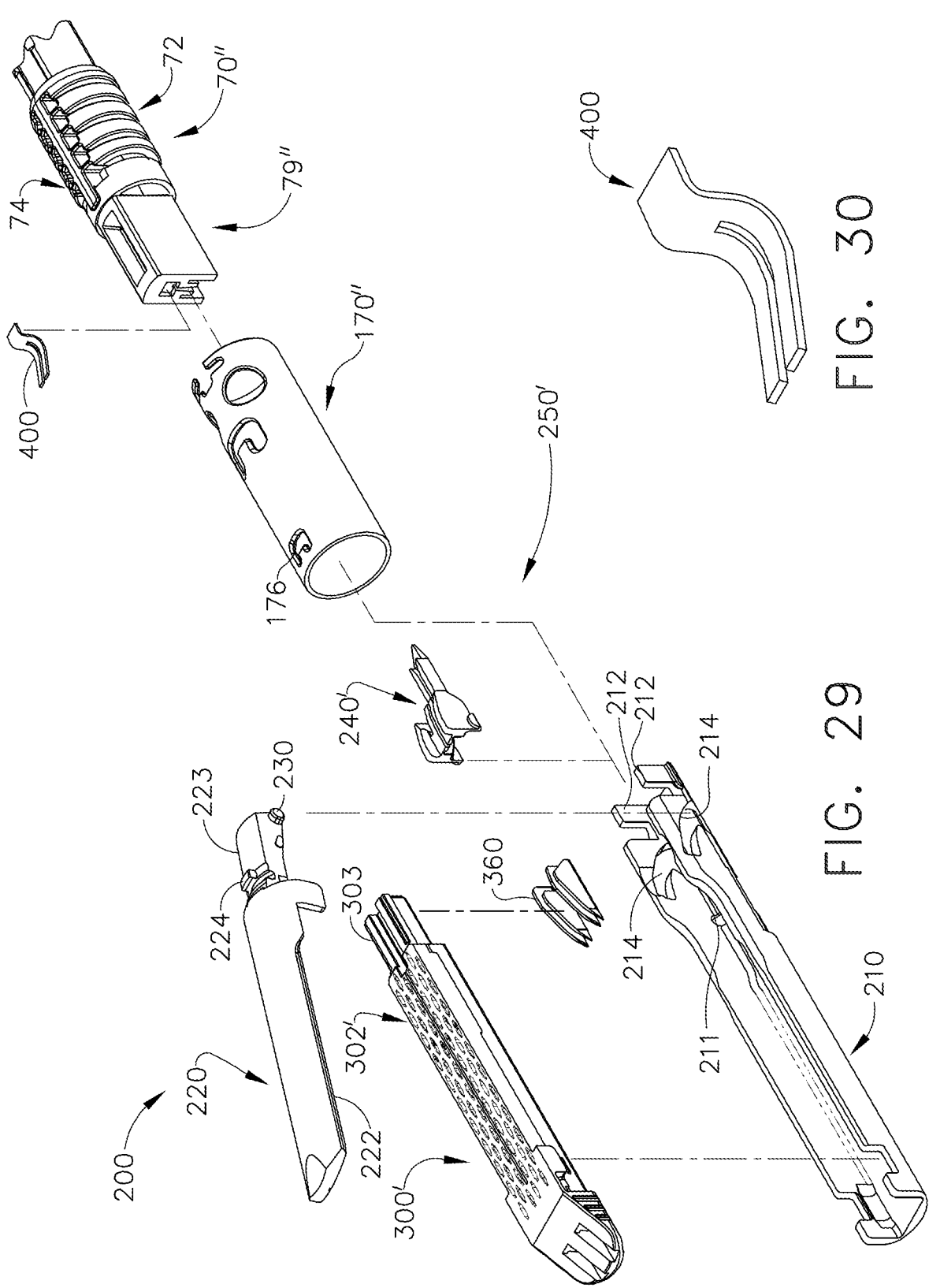
FIG. 29 is a partial exploded perspective view of an end effector and another anvil lock member embodiment.
FIG. 30 is a perspective view of another anvil lock member embodiment.

This embodiment also includes an anvil lockout system 250' that prevents closure of the anvil 220 when a staple cartridge 300' has not been properly installed in the elongate channel 210. Referring to FIGS. 29 and 30, for example, an embodiment of an anvil lockout system 250' includes an anvil lock member 400 that is configured to contact the anvil mounting portion 223 as will be discussed in further detail below. In at least one form, the anvil lock member 400 comprises a leaf spring 402 that has a slot 404 therein for accommodating the knife bar 130. The leaf spring 402 is configured for attachment to the channel guide 79" of the flex neck assembly 70".

Figures 31, 32:
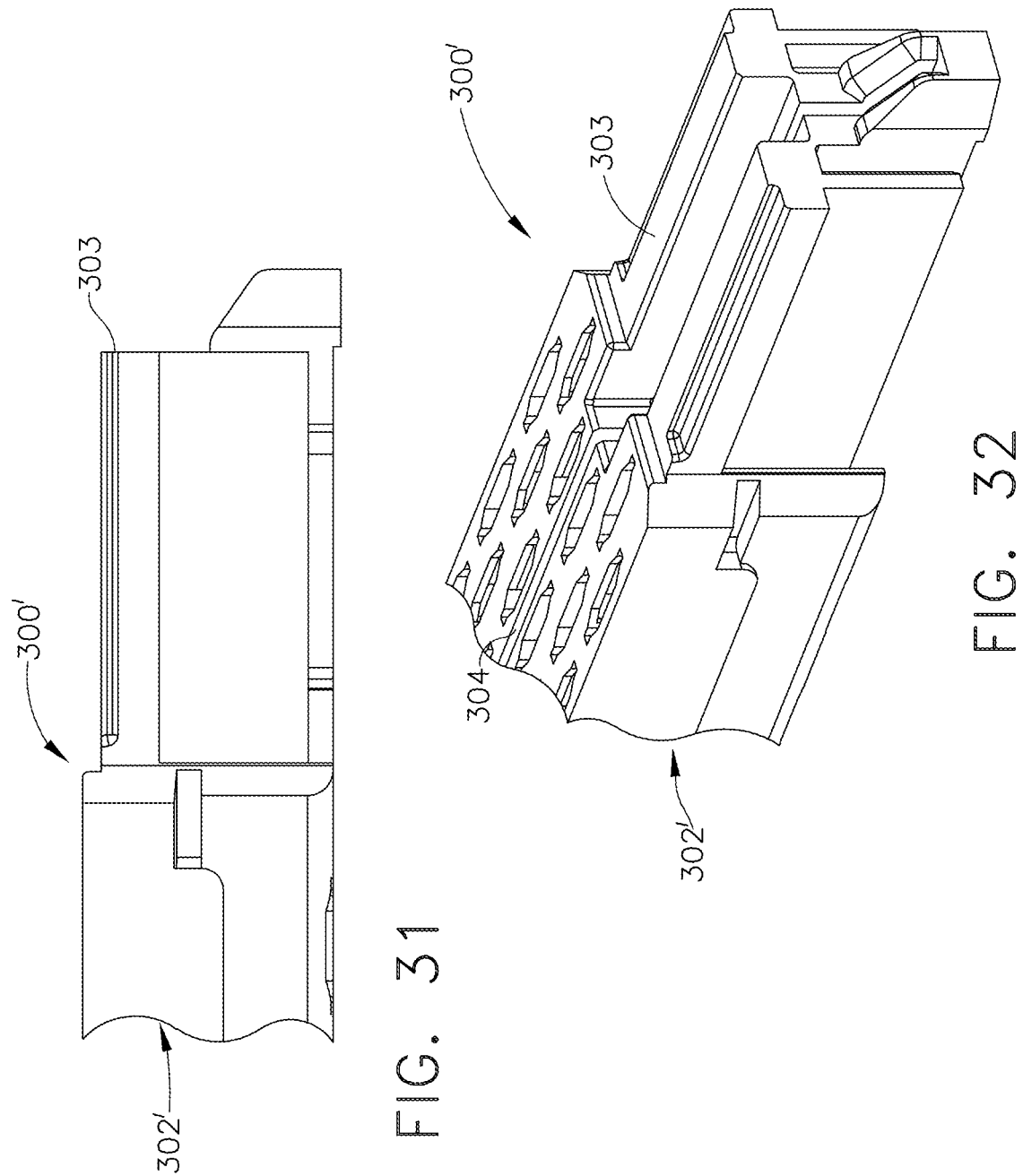
FIG. 31 is a partial side elevational view of a proximal end portion of another surgical staple cartridge embodiment.
FIG. 32 is a perspective view of a proximal end portion of the surgical staple cartridge embodiment of FIG. 31.

As can be seen in FIGS. 31 and 32, in at least one form, the surgical staple cartridge 300' includes a cartridge body 302' that is similar to the surgical staple cartridge 300 described above, except for the differences discussed below. FIG. 29 depicts a wedge sled 360 that is supported within the cartridge body 302' in the manner described above. In this embodiment, the proximal end portion 303 of the cartridge body 302' is configured to contact a portion of the anvil mounting portion 223 and urge the anvil 220 proximally when the cartridge body 302' is seated within the elongate channel 210.

Figures 33, 34:
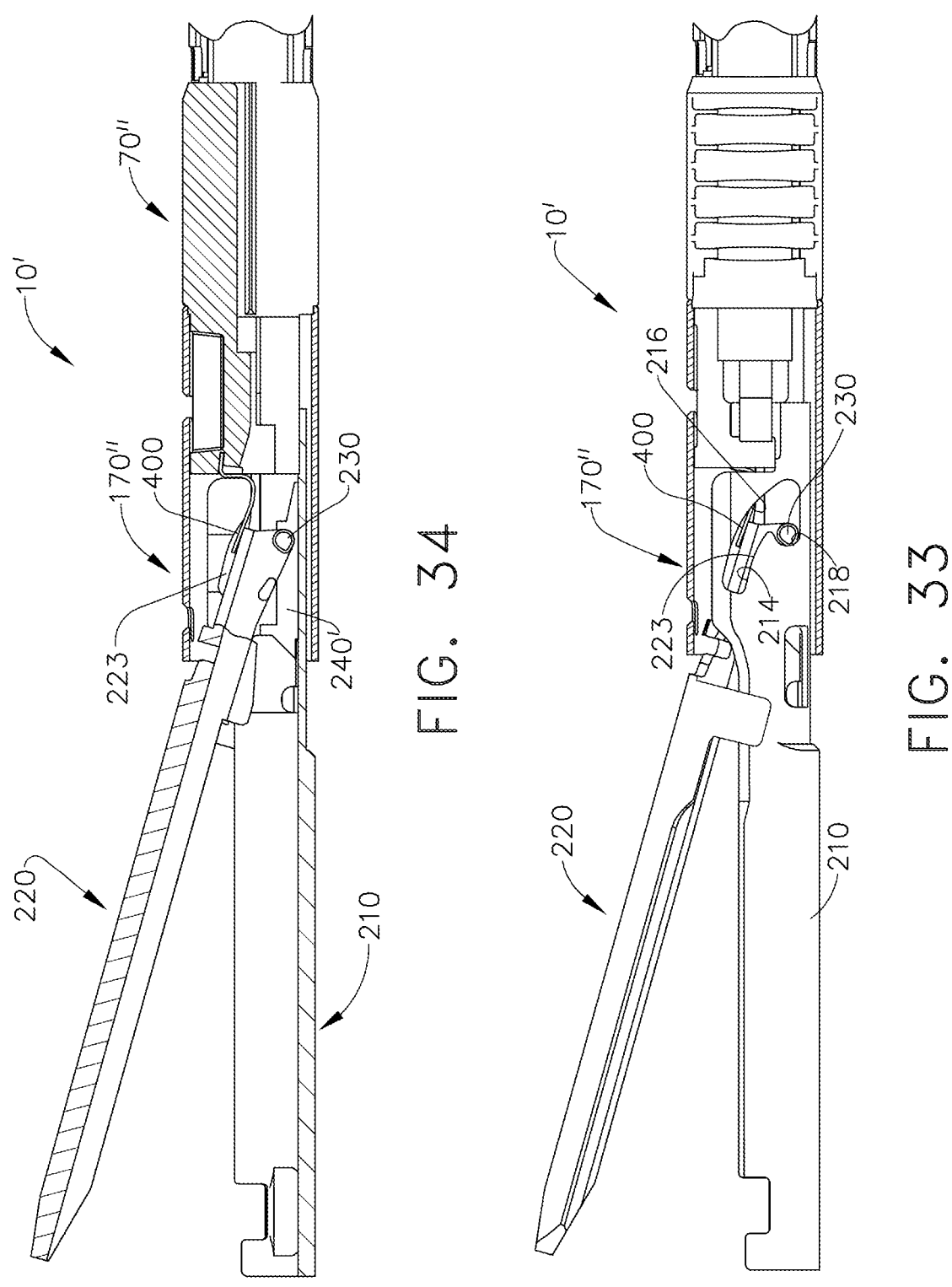
FIG. 33 is a side view of another end effector embodiment prior to seating a staple cartridge in the elongate channel.
FIG. 34 is a cross-sectional view of the end effector depicted in FIG. 33.

An understanding of the operation of a anvil lockout system 250' may be gleaned from reference to FIGS. 33-43. FIGS. 33 and 34 illustrate the position of the anvil 220 relative to the elongate channel 210 prior to installing a staple cartridge 300'. When in that "unloaded" position, the anvil lock member 400 has engaged the upper surface of the anvil support portion 223 such that the anvil 220 is pivoted to the open position on the rocker surfaces 248' on the pivot mount 140'. When in that position, the trunnions 230 are seated in their respective locking notch 218. When in that position, the surgeon cannot close the anvil 220 by actuating the closure trigger 152 to advance the distal closure tube 170'. Because the closure tube segments cannot be advanced distally to close the anvil 220, the closure trigger 152 cannot be actuated to its fully closed position whereby the firing trigger 102 may be actuated. Thus, when no cartridge 300' is present, the end effector 200 may not be actuated.

FIGS. 35 and 36 illustrate the initial insertion of the staple cartridge 300' into the elongate channel 210. FIGS. 37 and 38 illustrate the end effector 200 after the staple cartridge 300' has been fully seated in the elongate channel 210. As can be seen in FIG. 37 for example, when the cartridge 300' has been fully seated, the proximal end portion 303 on the cartridge 300' engages the trunnion walls 226, 228 and serves to move the anvil mounting portion 223 in a proximal direction "PD" such that the trunnions are moved out of their respective locking notch 218 and into an actuatable position the bottom of the arcuate slot segment 216. The anvil 220 is now in position to be pivoted closed by actuating the closure trigger 152.

Figures 39, 40:
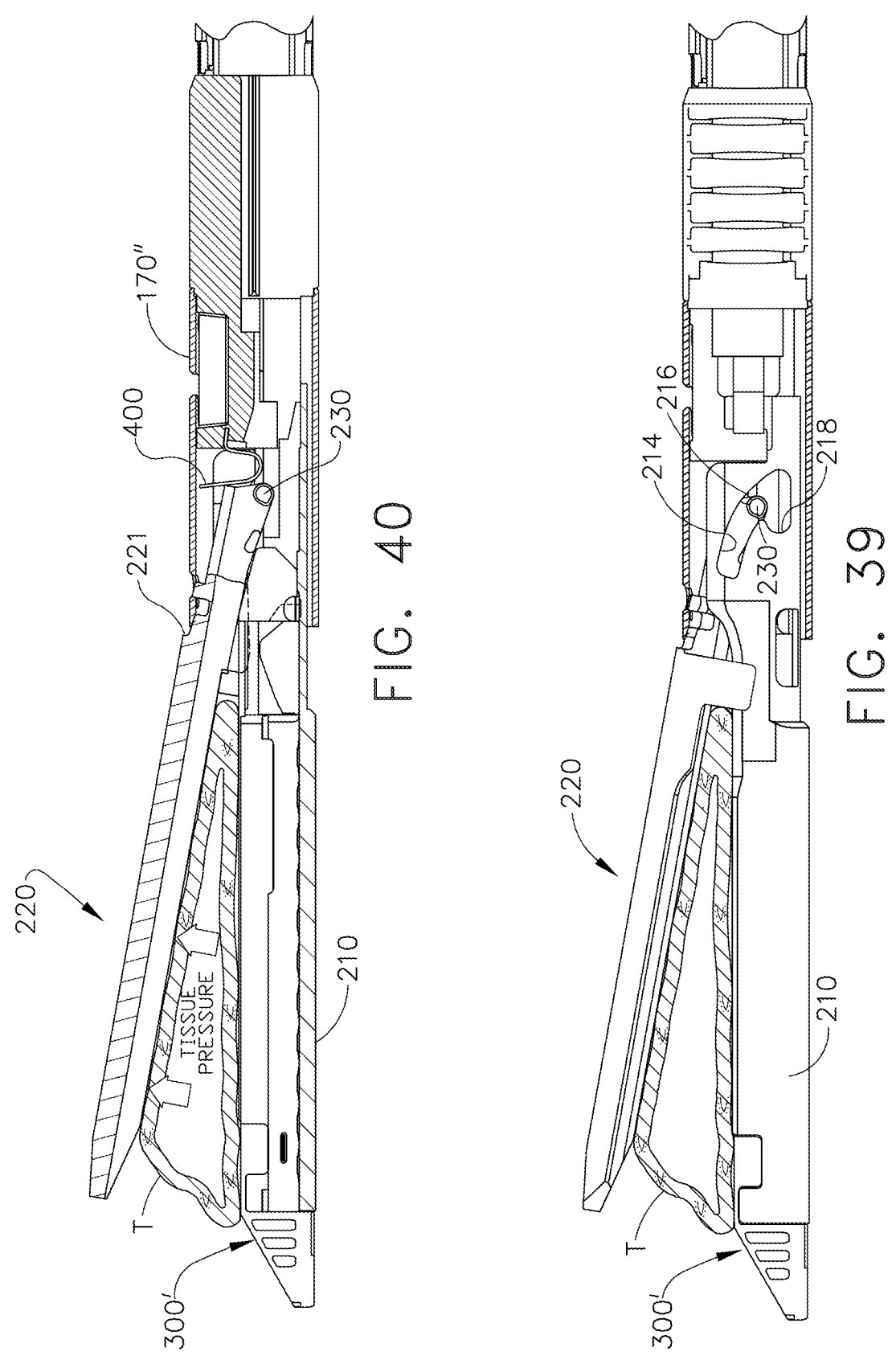
FIG. 39 is a side elevational view of the end effector of FIGS. 33-38 clamping tissue.
FIG. 40 is a cross-sectional view of the end effector of FIG. 39.

When the device 10' is in the starting position and the staple cartridge 300' has been loaded into the elongate channel 210 as described above, both of the triggers 152, 102 are forward and the anvil 220 is open and in the actuatable position, such as would be typical after inserting the loaded end effector 200 through a trocar or other opening into a body cavity. The instrument 10' is then manipulated by the clinician such that tissue "T" to be stapled and severed is positioned between the staple cartridge 300' and the anvil 220, as depicted in FIGS. 39 and 40. As discussed above, movement of the closure trigger 152 toward the pistol grip 24 causes the proximal closure tube segment 151, the flex neck assembly 70" and the distal closure tube segment 170" to move distally. As the distal closure tube segment 170' moves distally, it contacts a closure ledge 221 on the anvil 220. Pressure from the tissue captured between the anvil 220 and the staple cartridge 300' serves to move the anvil 220 such that the trunnions 230 are positioned to move within the arcuate trunnion slot segments 216. The surgeon may pivot the anvil 220 relative to the staple cartridge to manipulate and capture the desired tissue "T" in the end effector 200. As the distal closure tube segment 170" contacts the closure ledge 221, the anvil 220 is pivoted towards a clamped position. The retracted knife bar 130 does not impede the selective opening and closing of the anvil 220.

Figure 42:
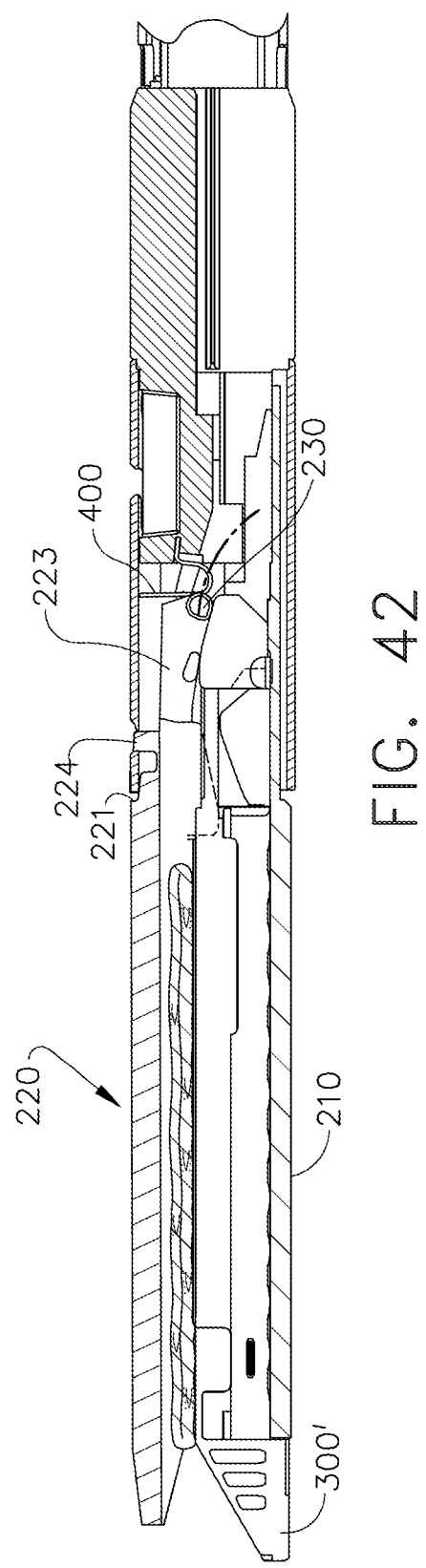
FIG. 42 is a cross-sectional view of the end effector of FIG. 41.
Figure 41:
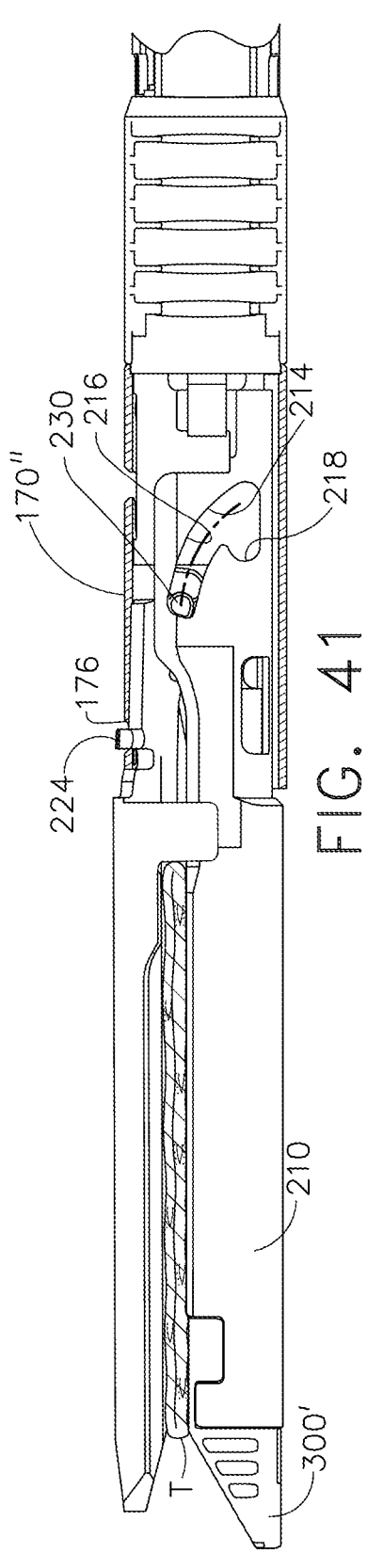
FIG. 41 is a side elevational view of the end effector of FIGS. 33-40 in a fully clamped position ready to fire.

Once the desired tissue "T" has been positioned between the anvil 220 and the cartridge 300', the clinician moves the closure trigger 152 proximally until positioned directly adjacent to the pistol grip 24, locking the handle 20 into the closed and clamped position. As can be seen in FIG. 42, when in the fully clamped position, the anvil trunnions 230 are located in the upper end of the arcuate slot portion 216 and the anvil tab 224 is received within the opening 176 in the distal closure tube segment 170". After tissue clamping has occurred, the clinician moves the firing trigger 102 proximally causing the knife bar 130 to move distally into the end effector 200. In particular, the knife bar 130 moves through the slot 236 in the pivot tab portion 234 of the anvil 220 and into the slot 304 in the cartridge body 302' to contact the wedge sled 360 operably positioned in therein. As the knife bar 130 is driven distally, it cuts the tissue T and drives the wedge sled 360 distally which causes the staples to be sequentially fired into forming contact with the staple-forming undersurface 222 of the anvil 220. The clinician continues moving the firing trigger 102 until brought proximal to the closure trigger 152 and pistol grip 24. Thereby, all of the ends of the staples are bent over as a result of their engagement with the anvil 220. The cutting edge 132 has traversed completely through the tissue T. The process is complete by releasing the firing trigger 102 and by then depressing the release button 120 while simultaneously squeezing the closure trigger 152. Such action results in the movement of the distal closure tube segment 170″ in the proximal direction "D". As the anvil tab 224 is engaged by the opening 176 in the distal closure tube segment 170″, it causes the anvil 220 to pivot open. The anvil lock member 400 applies a biasing force to the upper surface of the trunnion walls of the anvil mounting portion 223 and serves to pivot the anvil to the open position shown in FIGS. 33 and 34 to enable the spent cartridge 300′ to be removed from the elongate channel 210. The entire disclosure of U.S. patent application Ser. No. 13/429,647, entitled SURGICAL STAPLING DEVICE WITH LOCKOUT SYSTEM FOR PREVENTING ACTUATION IN THE ABSENCE OF AN INSTALLED STAPLE CARTRIDGE, which was filed on Mar. 26, 2012, now U.S. Pat. No. 9,078,653, is incorporated herein by reference.

Referring now to FIGS. 43-60, an implement portion 1022 can be coupled to the handle of a surgical instrument, such as to the handle 20 of the surgical stapling device 10 (see, e.g., FIGS. 1 and 2), for example. Similar to the implement portion 22 (see, e.g., FIG. 6), the implement portion 1022 can include an elongate shaft assembly 1030, which can be operably coupled to an end effector 1200. In certain instances, the end effector 1200, which can be similar to the end effector 200, for example, can include an elongate channel 1210 and an anvil 1220. Moreover, when the closure trigger 152 (see, e.g., FIGS. 1 and 2) of the handle 20 is pivotally drawn toward the pistol grip 24 (see, e.g., FIGS. 1 and 2), the anvil 1220 can clamp and/or close relative to the elongate channel 1210 of the end effector 1200. Additionally, when the firing trigger 102 (see, e.g., FIGS. 1 and 2) of the handle 20 is pivotally drawn toward the pistol grip 24, for example, the end effector 1200 can staple and/or sever the tissue clamped therein. In various instances, similar to the end effector 200, the end effector 1200 can be configured to articulate about an elongate axis of the device 10 and, in other instances, the end effector may be non-articulatable.

Figure 43:
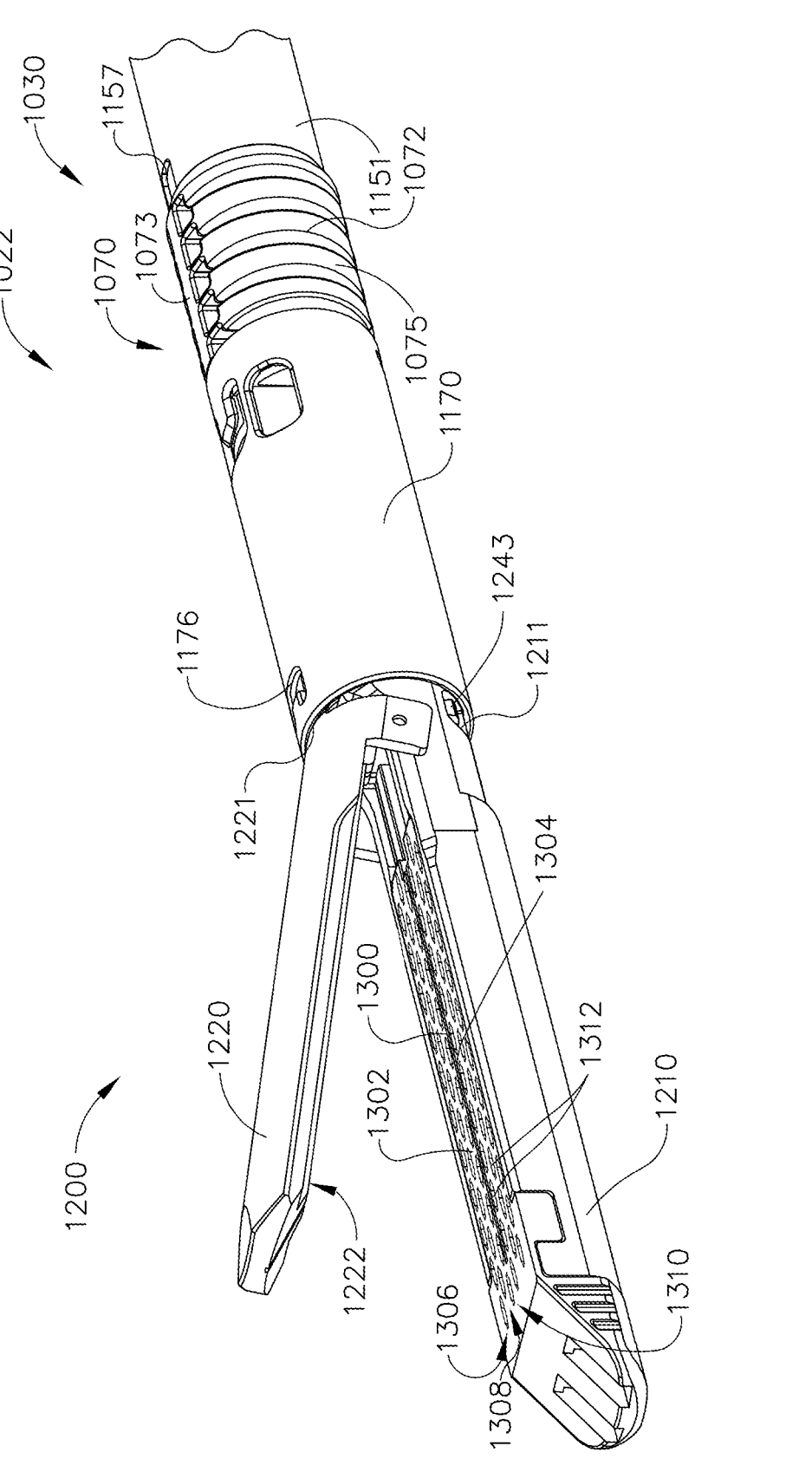
FIG. 43 is a perspective view of an end effector including an anvil, a closure tube engageable with the anvil, an elongate channel, and a staple cartridge positioned in the elongate channel according to various embodiments of the present disclosure.
Figure 44:
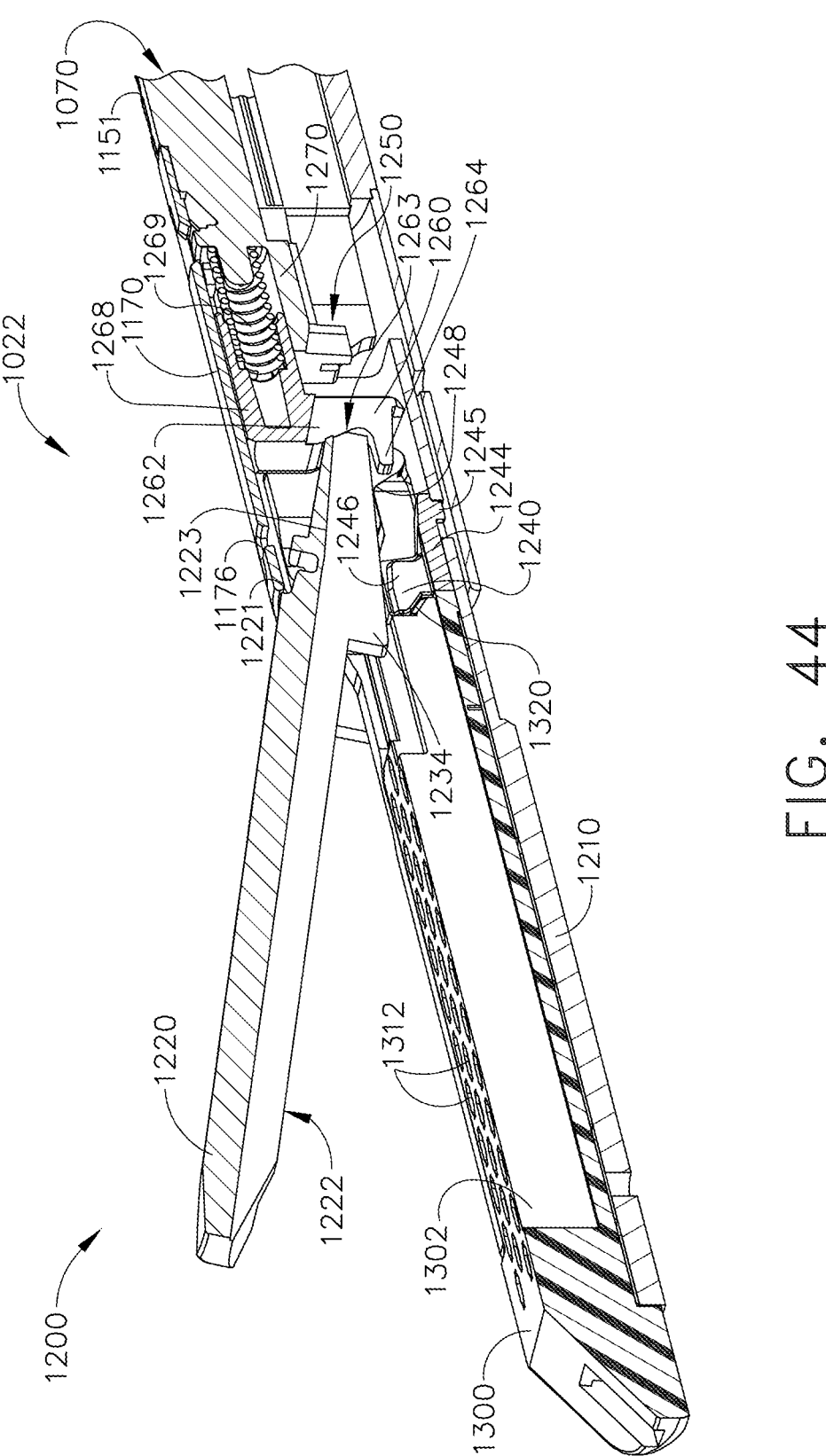
FIG. 44 is a cross-sectional, perspective view of the end effector of FIG. 43, illustrated with a cutting element and a wedge sled removed therefrom for the purposes of illustration.
Figure 45:
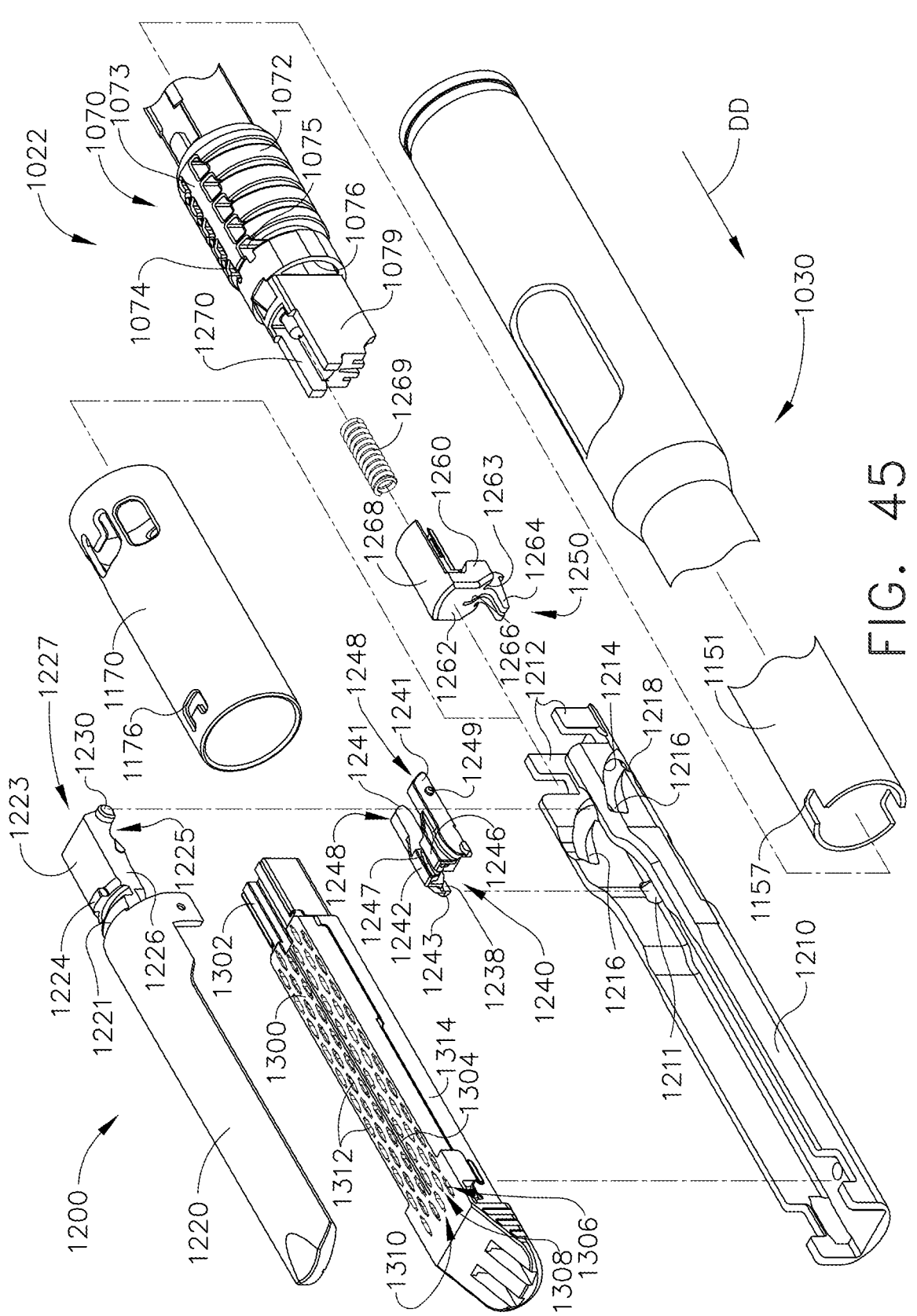
FIG. 45 is an exploded perspective view of the end effector of FIG. 43.

Referring primarily to FIGS. 43-45, the elongate shaft assembly 1030 can be similar to the elongate shaft assembly 30, for example, and can include a proximal closure tube segment 1151, which can extend from the handle 20 (see, e.g., FIGS. 1 and 2). In various instances, the proximal closure tube segment 1151 can include a distal end portion 1157, which can be coupled to a flexible neck assembly 1070. The flexible neck assembly 1070 can be similar to flexible neck assembly 70 (see, e.g., FIGS. 2 and 3) and, in such instances, the flexible neck assembly 1070 can permit articulation of the end effector 1200 relative to the proximal closure tube segment 1151, for example. In certain instances, the flexible neck assembly 1070 can have first and second flexible neck portions 1072, 1074, which can be separated by a central longitudinal rib 1073 (FIGS. 43 and 45). The neck portions 1072, 1074 can each have a plurality of neck ribs 1075, which can be configured essentially as semi-circular disks, for example. Moreover, a side slot 1076 (FIG. 45) can extend through each of the neck ribs 1075 to provide a passage through the first and second flexible neck portions 1072, 1074 for articulation members, such as the articulation members 89, 90 (see, e.g., FIG. 2) and exterior reinforcement band portions 86, 87 (see, e.g., FIG. 2) of the flexible band assemblies 83, 85 (see, e.g., FIG. 2), for example. In a similar fashion, the central longitudinal rib 1073 of the flexible neck assembly 1070 can separate the first and second flexible neck portions 1072, 1074, for example, and can have a central longitudinal slot for providing a passage to receive stapler actuating members, for example. In various instances, a channel guide 1079 (FIG. 45) can extend from the distal end of the flexible neck portions 1072, 1074, for example, and can guide the movement of the stapler actuating member(s) into a surgical staple cartridge 1300 of the end effector 1200.

As discussed above, the end effector 1200 can comprise the elongate channel 1210, which can be configured to operably receive a surgical staple cartridge 1300. Moreover, the anvil 1220 can be movably supported relative to the elongate channel 1210 and can be moved from an open position (see, e.g., FIGS. 52 and 53) to closed positions (see, e.g., FIGS. 59 and 60), in which tissue between the anvil 1220 and the elongate channel 1210 can be cut and/or stapled, for example. The movement of the anvil 1220 between open and closed positions is at least partially controlled by a closure system, which, as indicated above, is controlled by the closure trigger 152 (see, e.g., FIGS. 1 and 2).

Figure 46:
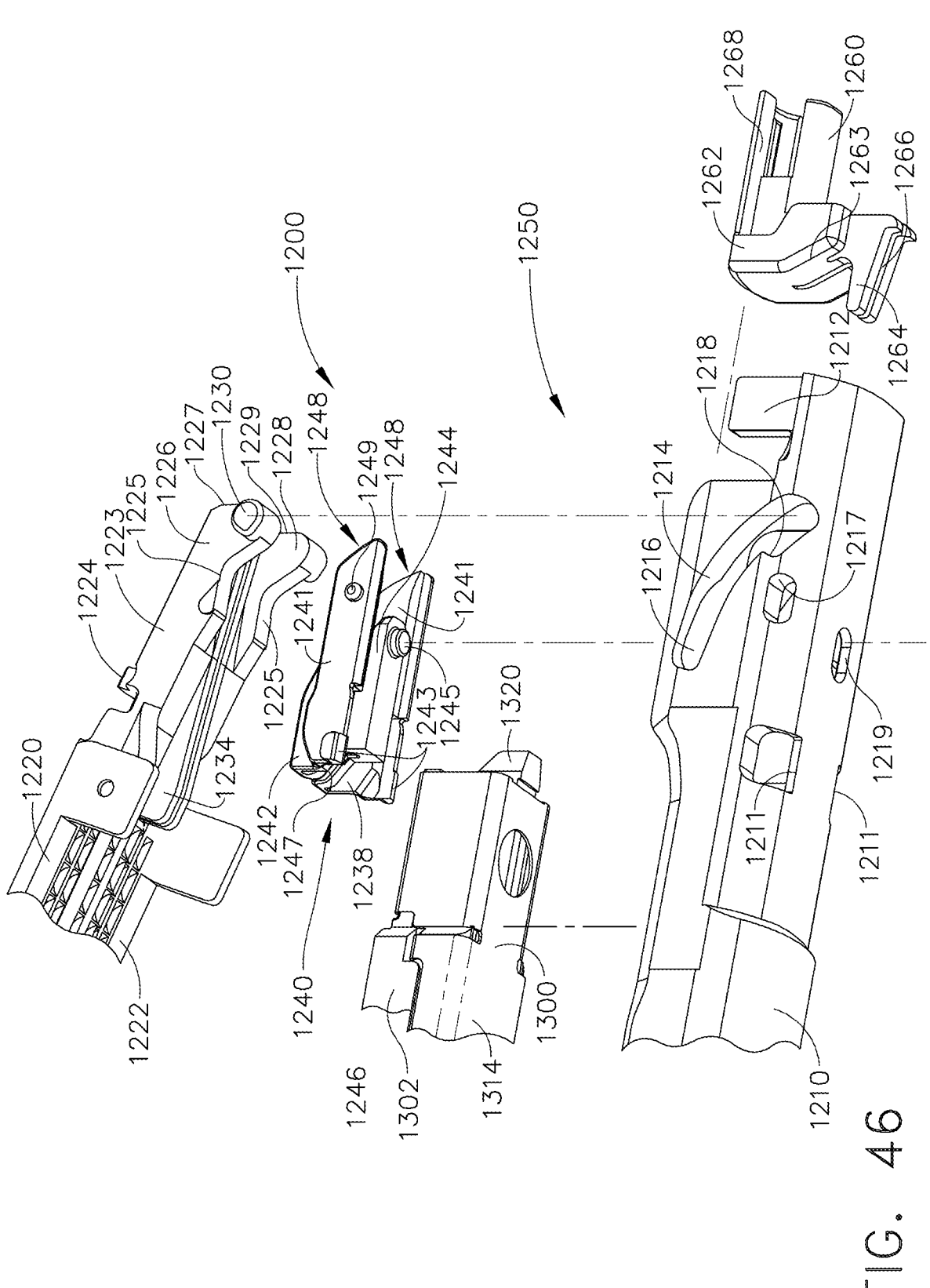
FIG. 46 is a partial exploded perspective view of the end effector of FIG. 43.
Figure 47:
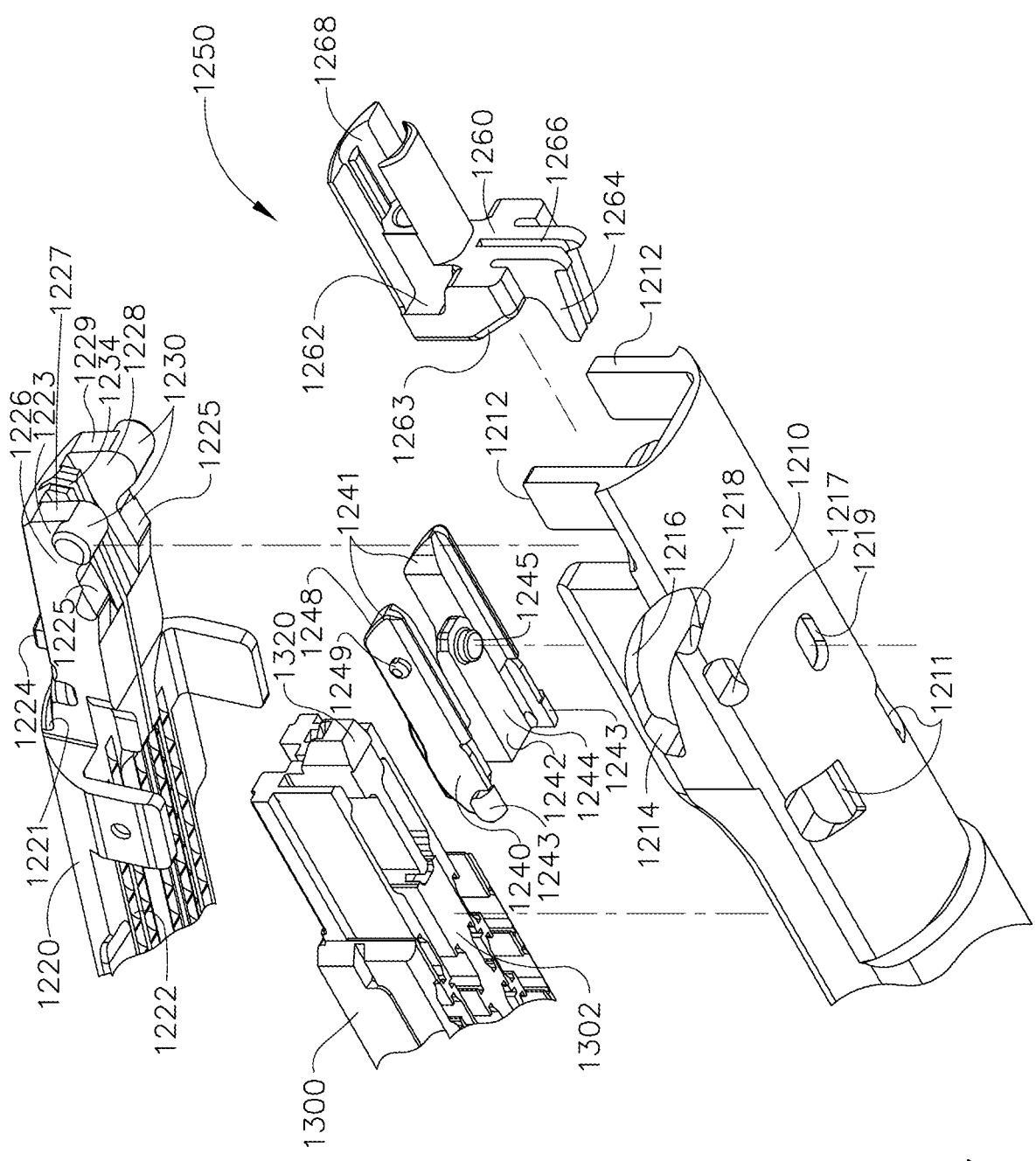
FIG. 47 is another partial exploded perspective view of the end effector of FIG. 43.

In at least one form, the closure system can include a distal closure tube segment 1170, which can be similar to distal closure tube segment 170 (see, e.g., FIGS. 1 and 2), for example. The distal closure tube segment 1170 can be non-movably coupled to the channel guide 1079 (FIG. 45) of the flexible neck assembly 1070. In various instances, the distal closure tube segment 1170 can comprise an opening 1176 therein, which can be adapted to interface with an upstanding tab 1224 formed on the anvil 1220. In various instances, axial movement of the proximal closure tube segment 1151 can result in axial movement of the flexible neck assembly 1070, as well as axial movement of the distal closure tube segment 1170. In such instances, distal movement of the proximal closure tube segment 1151 can generate translational movement of the anvil 1220 distally and rotational movement toward the elongate channel 1210 of the end effector 1200, for example. Correspondingly, proximal movement of the proximal closure tube segment 1151 can generate translational movement of the anvil 1220 proximally and rotational movement away from the elongate channel 1210 of the end effector 1200, for example Further to the above, as shown in FIGS. 45-47, the elongate channel 1210 can have a proximal end portion that includes spaced mounting tabs 1212. For example, a mounting tab 1212 can be positioned on each lateral side of the elongate channel 1210. In various instances, the mounting tabs 1212 can be configured to be engaged by hooks on the distal ends of articulation bands, such as the articulation bands 96 and 97 (see, e.g., FIG. 2), for example. Thus, in certain instances, reciprocating motions of the articulation bands can affect articulation of the elongate channel 1210 relative to the flexible neck assembly 1070, for example. A staple cartridge 1300 positioned within the elongate channel 1210 can move with the elongate channel 1210 such that the staple cartridge 1300 can be positioned within a surgical site.

Also further to the above, the anvil 1220 can have a staple-forming undersurface 1222 thereon which can be configured for confronting engagement with the staple cartridge 1300 when the staple cartridge 1300 has been mounted in the elongate channel 1210. In various instances, the anvil 1220 can further include a closure ledge 1221, which can be placed in abutting contact with the distal edge of the distal closure tube 1170, for example. The anvil 1220 can be formed with a proximally extending mounting portion 1223, for example, which can includes trunnion walls 1226, 1228 that each have a trunnion 1230 protruding outwardly therefrom. In various instances, each trunnion wall 1226 and 1228 can have a proximal end surface 1227 and 1229, respectively, for example, which can operably interface with an anvil lock member 1260 of the anvil lockout system 1250, as described in further detail herein. Moreover, in certain instances, each trunnion wall 1226, 1228 can further include a contoured surface 1225, for example, which can operably interface with an abutment surface 1248 of a shiftable guide 1240, as described in further detail herein.

In various instances, a downwardly protruding pivot tab 1234 can be formed on the underside 1222 of the proximally extending mounting portion 1223. In various instances, a longitudinal slot 1236 can be defined through the pivot tab 1234 and, in certain instances, the slot 1236 can be configured to receive and support a knife bar, such as the knife bar 130 (see, e.g. FIGS. 2 and 3), for example, as the knife bar 130 is axially advanced through the end effector 1200 to perform the cutting and stapling functions of the end effector 1200. In addition, the anvil opening tab 1224 can be formed on the mounting portion 1223, such that the tab 1224 can operably interface with the opening 1176 in the distal closure tube segment 1170, as further discussed herein.

Referring now to FIGS. 48, 50, 52, 55, 57 and 59, the anvil trunnions 1230 can be configured to be movably received in corresponding trunnion slots 1214 formed in the proximal end of the elongate channel 1210. In various instances, each trunnion slot 1214 can have an arcuate slot segment 1216 and a locking notch 1218. The arcuate slot segment 1216 can form a pivot path for the trunnion 1230, for example, as the anvil 1220 pivots relative to the elongate channel 1210, for example. Moreover, in certain instances, when the trunnion 1230 is received in the locking notch 1218, the geometry of the locking notch 1218 can prevent travel of the trunnion 1230 along the arcuate slot segment 1216, for example.

In various embodiments, the end effector 1200 can include a shiftable guide 1240, which can be slidably retained in the elongate channel 1210, for example. Referring primarily to FIGS. 45-47, the shiftable guide 1240 can comprises a body portion 1242 that can be configured to move or slide within the elongate channel 1210. In at least one instance, the body portion 1242 may be formed with two opposed attachment tabs 1243 that are configured to retainingly engage tab openings 1211 formed in the elongate channel 1210. Additionally or alternatively, the shiftable guide 1240 can have a proximally extending foot portion 1244, which can have a downwardly protruding retainer lug 1245. In various instances, the retainer lug 1245 can be dimensioned and positioned such that it can be received in a corresponding lug opening 1219 (see, e.g. FIGS. 46 and 47) in the bottom of the elongate channel 1210. Additionally or alternatively, the shiftable guide 1240 can include proximal nubs 1249 which can protrude from opposite lateral sides of the shiftable guide 1240, for example. In various instances, each nub 1249 can be slidably positioned in a nub slot 1217 (see, e.g., FIGS. 46 and 47) in the lateral sides of the elongate channel 1210.

In various instances, the shiftable guide 1240 can shift and/or move within the elongate channel 1210. For example, as described in further detail herein, various components of the end effector 1200 can bias the shiftable guide 1240 into and/or toward different positions within the elongate channel 1210. Moreover, when the shiftable guide 1240 moves within the elongate channel 1210, the opposed attachment tabs 1243 can slide within the tab openings 1211, the retainer lug 1245 can slide within the lug opening 1219, and/or the opposing proximal nubs 1249 can slide within the nub slots 1217, for example. In such instances, the tab openings 1211, the lug opening 1219, and/or the nub slots 1217 can constrain, guide and/or limit the shifting and/or displacement of the shiftable guide 1240 relative to the elongate channel 1210 along a longitudinal path, for example. This longitudinal path can comprise a range of positions for the shiftable guide 1240. In various instances, the longitudinal lengths of the tab openings 1211, the lug opening 1219 and/or the nub slots 1217 can limit the longitudinal range of motion of the shiftable guide 1240. As described in further detail herein, the shiftable guide 1240 can cooperate with an anvil lockout system 1250, for example, and can facilitate the locking and unlocking of the anvil 1220 relative to the elongate channel 1210, for example.

Referring still to FIGS. 45-47, the body portion 1242 of the shiftable guide 1240 can have an upstanding central portion 1246, for example, which can have a slot 1247 extending therethrough for axially receiving a knife bar, such as the knife bar 130 (see, e.g., FIGS. 2 and 3), for example. The central portion 1246 can provide lateral support to the knife bar 130 as it is driven through tissue clamped within the end effector 1200, for example. In various instances, the slidable guide 1240 can also include a barrier portion 1241, which can extend proximally from the body portion 1242. The barrier portion 1241 can form a wall and, in various instances, the proximal nub 1249 can extend outwardly from the wall of the barrier portion 1241, for example. In various instances, the shiftable guide 1240 can include a pair of lateral barrier walls 1241 which can be positioned on opposite sides of the proximally extending foot portion 1244. In at least one form, the lateral barrier walls 1241 can extend proximally beyond the foot portion 1244 and on either side thereof, for example.

In various instances, each lateral barrier wall 1241 can include a proximal-most edge, for example, which can define a ramped or contoured surface. As described in further detail herein, the ramped proximal edge can define a slope that corresponds to a sloped portion of the trunnion slot 1214. Various embodiments of the shiftable guide 1240 can also include abutment surfaces 1248 formed on each lateral barrier wall 1241. For example, the abutment surfaces 1248 can extend along the ramped proximal edge of each lateral barrier wall 1241. As described in further detail herein, the abutment surfaces 1248 can be operably positioned in abutting contact with a portion of the proximally extending mounting portion 1223 of the anvil 1220, for example. Moreover, in certain instances, the profile of the abutment surfaces 1248 can match and/or complement a portion 1225 of the proximally extending mounting portion 1223 of the anvil 1220, for example. As described in further detail herein, engagement between the abutment surfaces 1248 of the shiftable guide 1240 and the mounting portion 1223 of the anvil 1220 can affect movement of the trunnions 1230 between the locking notches 1218 and the arcuate slot segments 1216, for example.

In various instances, as the shiftable guide 1240 is moved within the elongate channel 1210, the lateral barrier walls 1241 can move relative to the lockout notches 1218 defined in the elongate channel 1210. For example, when the shiftable guide 1240 is within a first range of positions relative to the elongate channel 1210, a portion of the lateral barrier walls 1241 can be longitudinally aligned with their respective lockout notches 1218 such that the barrier walls 1241 overlap the lockout notches 1218. When the shiftable guide 1240 is within a second range of positions relative to the elongate channel 1210, however, the lateral barrier walls 1241 can be longitudinally offset from the respective lockout notches 1218 such that the barrier walls 1241 do not overlap the lockout notches 1218, for example. In various instances, the ramped proximal edge and abutment surfaces 1248 of the barrier walls 1241 can move between a distal position which is distal to the lockout notches 1218 and a proximal position at least partially overlapping and/or extending past a least a portion of the lockout notches 1218.

As further indicated above, in various instances, the end effector 1200 can include an anvil lockout system 1250 which can prevent the anvil 1220 from being closed when a staple cartridge 1300 has not been installed and/or has not been properly installed in the elongate channel 1210. In various instances, the lockout system 1250 can operably interface with the shiftable guide 1240, for example, to prevent, or at least attempt to prevent, the closure of the anvil 1220. Referring to FIGS. 45-47, for example, the anvil lockout system 1250 can include a movable anvil lock member 1260, for example, which can be similar to anvil lock member 260, for example. In various instances, the anvil lock member 1260 can be movable in response to contact by a portion or portions of a staple cartridge 1300, as discussed in further detail below. Moreover, in at least one form, the anvil lock member 1260 can comprise a body portion 1262 which can have a distally protruding central support tab 1264 formed thereon. A slot 1266 can extend through the body portion 1262 and the central support tab 1264, for example, to enable a knife bar, such as the knife bar 130 (see, e.g., FIGS. 2 and 3), for example, to pass therethrough. Referring primarily to FIG. 45, the body portion 1262 can further include a proximally extending mounting bar 1268, for example, which can be configured to be slidably received within the corresponding mounting opening 1270 in the channel guide 1079 of the flexible neck assembly 1070. In various instances, a biasing member in the form of, for example, a coil spring 1269 can be supported within the opening 1270 to bias the anvil lock member 1260 in the distal direction "DD" (FIG. 45).

When the anvil 1220 is mounted to the elongate channel 1210, further to the above, the trunnions 1230 can be received within their corresponding trunnion slots 1214 in the elongate channel 1210, for example, and the central support tab 1264 of the anvil lock member 1260 can be received between the trunnion walls 1226, 1228, for example. In certain instances, the anvil lock member 1260 can be closely received between the trunnion walls 1226, 1228. Furthermore, the central support tab 1264 can be positioned intermediate the barrier walls 1241 of the shiftable guide 1240, for example. In certain instances, the body portion 1262 of the anvil lock member 1260 can be formed with two cam surfaces 1263, for example, which can be configured to operably engage the proximal end surfaces 1227, 1229 of the trunnion walls 1226, 1228 of the anvil 1220. In such instances, the cam surfaces 1263 of the anvil lock member 1260 can bias the mounting portion 1223 of the anvil 1220 distally and/or downwardly, similar to the cam surface 263 of anvil lock member 260, for example. In various instances, the cam surfaces 1263 of the anvil lock member 1260 can bias the trunnions 1230 of the anvil 1220 into and/or toward the locking notches 1218 in the elongate channel 1210, for example. Simply put, the spring 1269 can bias the anvil lock member 1260 distally and the anvil lock member 1260 can contact the anvil 1220 and push the trunnions 1230 distally. Similarly, the anvil 1220, when pushed distally by the anvil lock member 1260, can push the shiftable guide 1240 distally. As will be described in greater detail further below, the staple cartridge 1300, for example, can be inserted into the elongate channel 1210 to push the shiftable guide 1240, the anvil 1220, and the anvil lock member 1260 proximally to unlock the anvil 1220. Such proximal movement of the shiftable guide 1240, the anvil 1220, and the anvil lock member 1260 can resiliently compress the spring 1269. In the event that the staple cartridge 1300 were to be removed from the elongate channel 1210, the spring 1269 could resiliently expand to push the shiftable guide 1240, the anvil 1220, and the anvil lock member 1260 distally once again and lock the anvil 1220.

As discussed above, the surgical staple cartridge 1300, for example, can be structured and configured to interact with the anvil lockout system 1250 and the shiftable guide 1240, for example, when the staple cartridge 1300 is installed in the elongate channel 1210. Referring to FIGS. 45-47, the surgical staple cartridge 1300 can include a cartridge body 1302, which can be similar to cartridge body 302, for example. The cartridge body 1302 can be sized and structured to be received within the elongate channel 1210. In at least one form, the cartridge body 1302 can be configured to be seated in the elongate channel 1210 such that the cartridge body 1302 is removably retained therein. The cartridge body 1302 may be formed with a centrally disposed slot 1304 therein for receiving a knife bar, such as the knife bar 130 (see, e.g., FIGS. 2 and 3), for example. In various instances, rows 1306, 1308, 1310 of staple openings 1312 can be positioned on each side of the slot 1304, and can be configured to support a surgical staple (not shown) therein. Referring primarily to FIGS. 43 and 45, in various instances, three rows 1306, 1308, 1310 of staple openings 1312 can be defined on each side of the slot 1304. In other instances, the cartridge body 1302 can include fewer than six rows of staple openings 1312 or more than six rows of staple openings 1312, for example. In some instances, the openings 1312 may not be arranged in longitudinal rows. In various instances, the surgical staples may be supported on staple drivers (not shown), for example, which can be movably supported within the staple openings 1312.

As described above with respect to the cartridge body 302, in various instances, a wedge sled, such as wedge sled 360 (FIG. 29), for example, can be slidably positioned within the cartridge body 1302. The wedge sled can be configured for axial movement through the cartridge body 1302 when contacted by the knife bar. In various instances, the wedge sled can be configured with wedge-shaped driving members, for example, which can contact the staple drivers and drive the drivers and their corresponding staples toward the closed anvil, for example, as the wedge sled is driven distally through the cartridge body 1302. Examples of staple driver arrangements and wedge sled arrangements that may be employed are described in further detail in U.S. Pat. No. 7,669,746, entitled STAPLE CARTRIDGES FOR FORMING STAPLES HAVING DIFFERENT FORMED STAPLE HEIGHTS, which issued on Mar. 2, 2010, the entire disclosure of which is herein incorporated by reference. To facilitate installation of the wedge sled and drivers in the cartridge body 1302, in various embodiments, metal cartridge pan(s) 1314 may be attached to the cartridge body 1302, as shown in FIG. 45. The cartridge pan(s) 1314 can serve to retain the wedge sled and drivers within the cartridge body 1302.

Referring primarily to FIGS. 46 and 47, the cartridge body 1302 can further include a proximal nose portion 1320, for example, which can protrude from the cartridge body 1302 in the proximal direction. When the cartridge 1300 is
seated in the elongate channel 1210, for example, the
proximal nose portion 1320 can be configured to engage
and/or contact the shiftable guide 1240. In various instances,
the nose portion 1320 can have a tapered perimeter, for
example, which can facilitate engagement between the car-
tridge body 1302 and the shiftable guide 1240. In at least one
instance, a tapered recess 1238 in the distal end of the
shiftable guide 1240 can be configured to receive the proxi-
mal nose portion 1320 of the staple cartridge 1300. In such
instances, the shiftable guide 1240 can guide the staple
cartridge 1300 into a fully seated position and/or into proper
alignment within the elongate channel 1210. Moreover,
engagement between the proximal nose portion 1320 and the
tapered recess 1238 can facilitate proper alignment of the
slot 1304 in the cartridge body 1302 and the slot 1247 in the
shiftable guide 1240, for example, which can further facili-
tate proper alignment of the cartridge body 1302 with the
slot 1266 in the locking member 1260, the slot in the channel
guide 1079, and/or various elements of the firing assembly,
such as the knife bar 130 (see, e.g., FIGS. 2 and 3), for
example. As described in further detail herein, placement of
the staple cartridge 1300 in the elongate channel 1210 can
bias the shiftable guide 1240 proximally via engagement of
the proximal nose portion 1320 with the tapered recess 1238,
for example. The proximal movement of the shiftable guide
1240 can shift the proximal mounting portion 1223 of the
anvil 1220 proximally via engagement between the abut-
ment surfaces 1248 of the shiftable guide 1240 and the
contoured portions 1225 of the trunnion walls 1226, 1228,
for example. When the anvil 1220 is shifted proximally, the
trunnions 1230 of the anvil 1220 can move out of the locking
notches 1218 and into the arcuate slot segments 1216 of the
trunnion slots 1214 defined in the elongate channel 1210, for
example.

The operation of the anvil lockout system 1250 is
depicted in FIGS. 48-60. Referring to FIGS. 48-51, the anvil
1220 can be oriented in an open position relative to the
elongate channel 1210 prior to a staple cartridge being
inserted into the elongate channel 1210. The anvil 1220 can
also be oriented in the open position depicted in FIGS. 48-51
after a staple cartridge has been removed from the elongate
channel 1210. Such a configuration of the end effector 1200
can be referred to as an "unloaded" configuration. In such an
unloaded configuration, the anvil lock member 1260 can be
biased in the distal direction "DD" by the spring 1269, such
that the cam surfaces 1263 (FIG. 51) on the anvil lock
member 1260 are in contact with the end surfaces 1227,
1229 (FIGS. 50 and 51) of the trunnion walls 1226, 1228.
The anvil lock member 1260 can push the anvil mounting
portion 1223 in the distal direction "DD" and/or downward,
for example, such that the trunnions 1230 are seated in their
respective locking notches 1218. The cam surfaces 1263 on
the anvil lock member 1260, in cooperation with the end
wall surfaces 1227, 1229 defined on the anvil 1220, can also
serve to pivot and retain the anvil 1220 in the open position
shown in FIGS. 48-51. In the event that an operator of a
surgical instrument comprising the end effector 1200
attempts to close the anvil 1220 when the end effector 1200
is in its unloaded configuration, the anvil lock member 1260
can resist or prevent the closure of the anvil 1220. Stated
another way, the anvil lock member 1260 can prevent the
rotation of the anvil 1220 toward the elongate channel 1210
which can, in turn, prevent the distal displacement of the
closure tube segment 1170. In such circumstances, the
closure trigger 152 cannot be actuated to its fully closed
position by the operator of the surgical instrument and, as a result, the firing trigger 102 (see, e.g., FIGS. 1 and 2) cannot
be actuated to fire the staples contained within the staple
cartridge and/or incise the tissue captured between the staple
cartridge and the anvil 1220. Thus, when no staple cartridge
is present in the elongate channel 1020 and/or when a staple
cartridge, such as the staple cartridge 1300, is not fully
seated in the elongate channel 1020, the end effector 1200
may not be actuated. Moreover, in various instances, when
the wrong staple cartridge has been loaded into the elongate
channel, such as a staple cartridge that is shorter than the
intended staple cartridge 1300, the anvil lock system 1250
can prevent the operator from closing and actuating the end
effector. Such a system can be referred to as a "no-cartridge
lockout" and/or a "short cartridge lockout", for example.

When the anvil mounting portion 1223 is biased in the
distal direction "DD", referring again to FIGS. 48-51, the
contoured portion 1225 (FIGS. 49 and 51) of the trunnion
walls 1226, 1228 can be placed and/or pushed into abutting
engagement with the proximally extending barrier portions
1241 of the shiftable guide 1240 such that the shiftable guide
1240 is also shifted into and/or biased toward the distal
direction "DD". In such instances, the attachment tabs 1243,
the retainer lug 1245, and/or the nubs 1249 can be shifted
distally in their respective slots and/or openings 1211, 1217,
1219 in the elongate channel 1210, for example. Moreover,
the trunnion walls 1226, 1228 can push the proximally
extending barrier portions 1241 distally past the locking
notches 1218. Stated another way, the proximally extending
barrier portions 1241 can be positioned distally such that the
proximal ends of the barrier portions 1241 and the abutment
surfaces 1248 (FIG. 51) of the barrier portions 1241 are
longitudinally offset from, and not overlapping with, the
locking notches 1218. In such a position, the barrier portions
1241 of the shiftable guide 1240 do not block the trunnions
1230 from entering into the locking notches 1218. In fact,
the biasing force which pushes the shiftable guide 1240
distally also pushes the trunnions 1230 into the locking
notches 1218. The trunnions 1230 can be configured such
that they do not rotate, or at least substantially rotate, when
they are positioned within the locking notches 1218 which,
as a result, prevents the anvil 1220 from rotating relative to
the elongate channel 1210. In various instances, the trun-
nions 1230 may comprise a non-circular cross-section, for
example. In certain instances, each trunnion 1230 can com-
prise a circular portion and a lock portion extending from the
circular portion, for example. The circular portion can define
an axis about which the anvil 1220 can rotate and the lock
portion can be configured to engage a lock notch 1218. In at
least one instance, the lock portion of a trunnion 1230 can
comprise a wedge configured to abut a sidewall of a lock
notch 1218 and, owing to this abutting relationship, the anvil
1220 may not rotate, or at least substantially rotate, relative
to the elongate channel 1210. In order for the anvil 1220 to
be rotated relative to the elongate channel 1210, the anvil
1220 can be pushed proximally such that the lock portions
of the trunnions 1230 are disengaged from the lock notches
1218 and the trunnions 1230 can enter into the arcuate
portions 1216 of the trunnion slots 1214 as described herein.

FIGS. 52-60 depict the staple cartridge 1300 fully seated
within the elongate channel 1210. When the staple cartridge
1300 has been fully seated, referring primarily to FIGS.
52-54, the proximal nose portion 1320 of the cartridge 1300
can be nested within the recess 1238 (FIG. 54) in the
shiftable guide 1240. In various instances, the tapered nose
portion 1320 can slide into the recess 1238 in the shiftable
guide 1240 until the cartridge body 1302 is in abutting
engagement with the shiftable guide 1240. As the staple cartridge 1300 is moved into the fully seated positioned with the elongate channel 1210, the tapered nose portion 1320 can push the shiftable guide 1240 in the proximal direction "PD", for example.

Figures 52, 53:
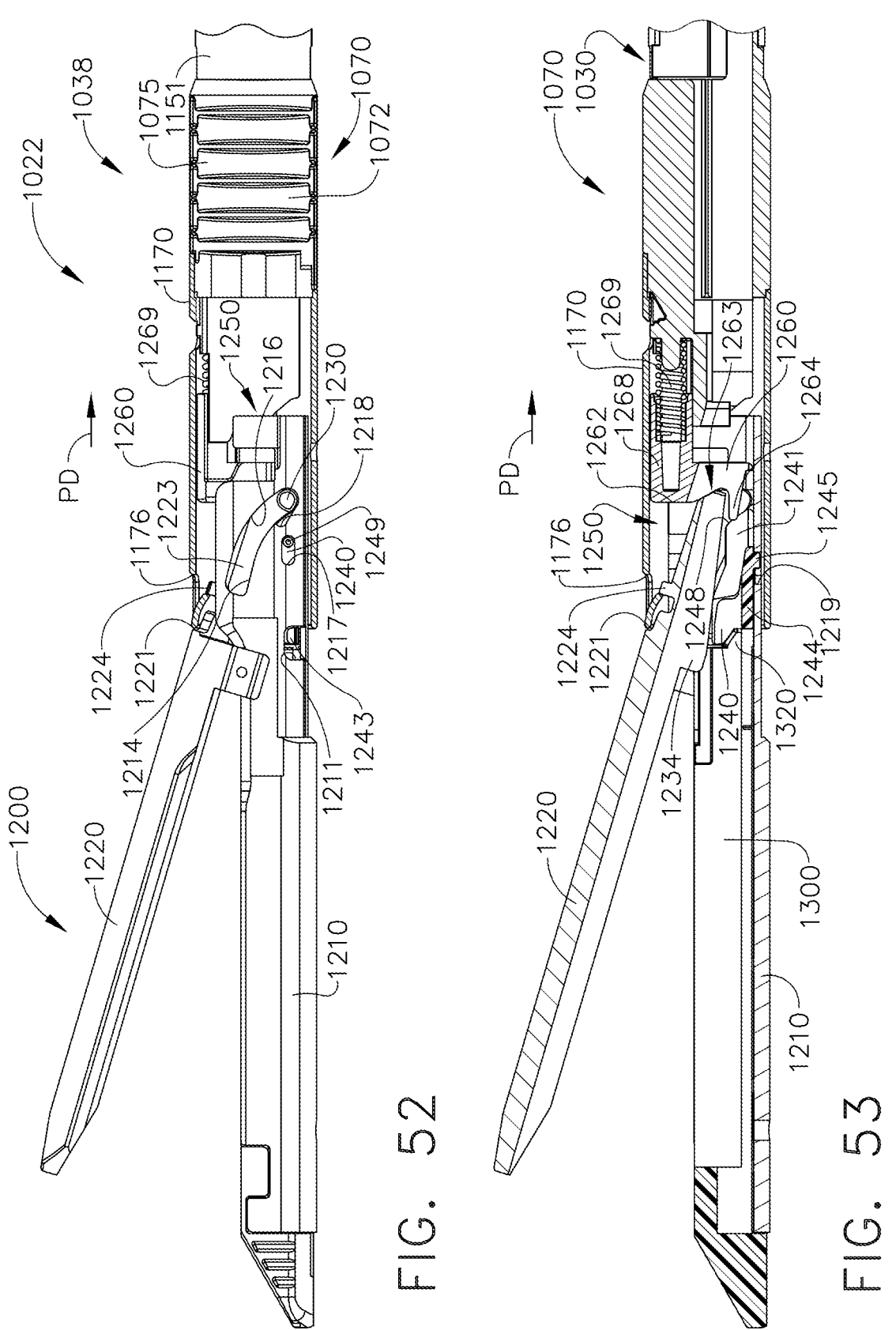
FIG. 52 is an elevation view of the end effector of FIG. 43 depicting the anvil in an open orientation, the anvil lockout system, and the staple cartridge positioned in the elongate channel, wherein the closure tube of the end effector has been illustrated in cross-section to illustrate other various aspects of the end effector.
FIG. 53 is a cross-sectional elevation view of the end effector of FIG. 43 in the configuration illustrated in FIG. 52.
Figure 54:
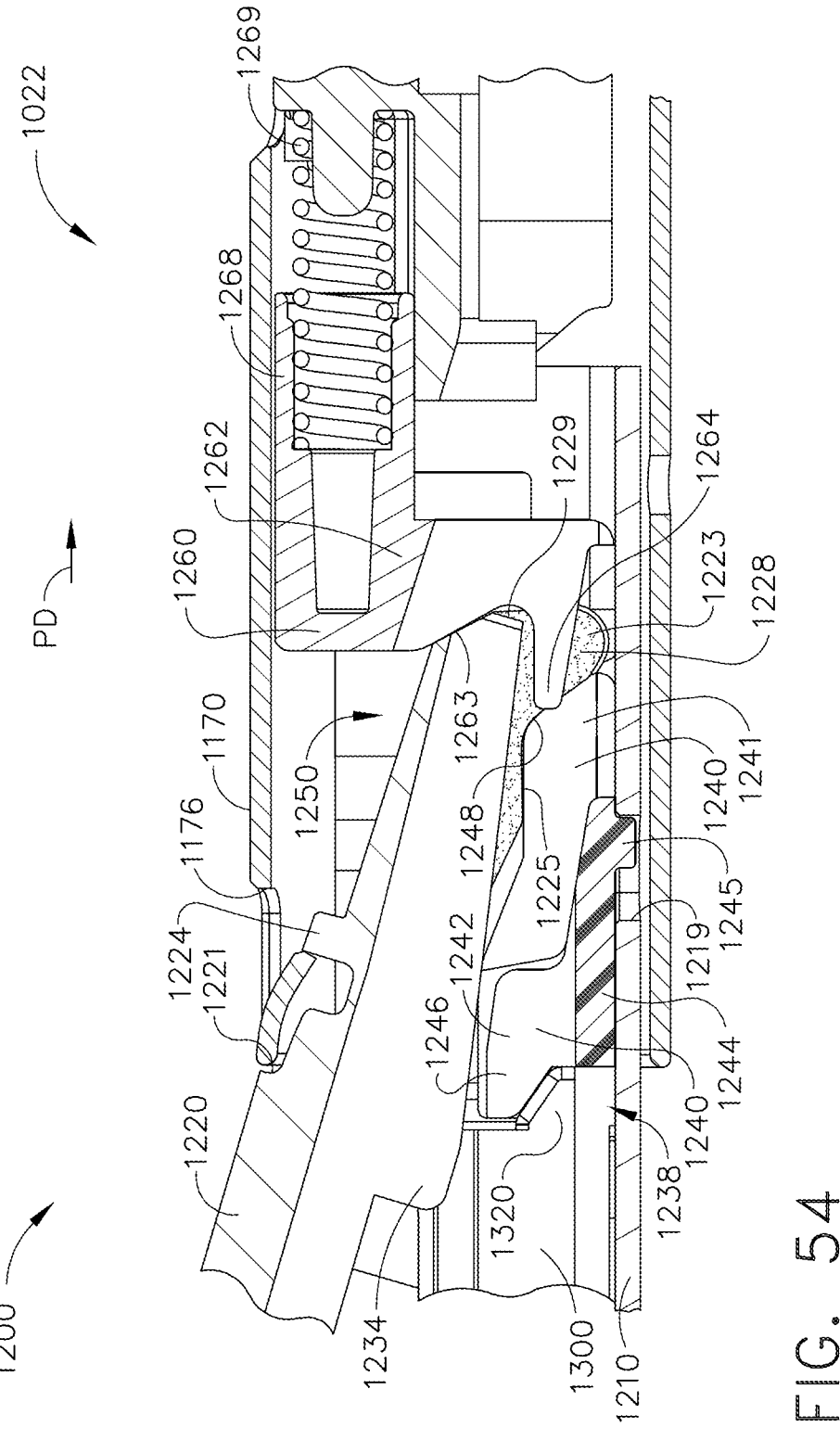
FIG. 54 is a detail view of the anvil lockout system depicted in FIG. 53, wherein a mounting portion of the anvil is shaded for the purposes of illustration.
Figures 55, 56:
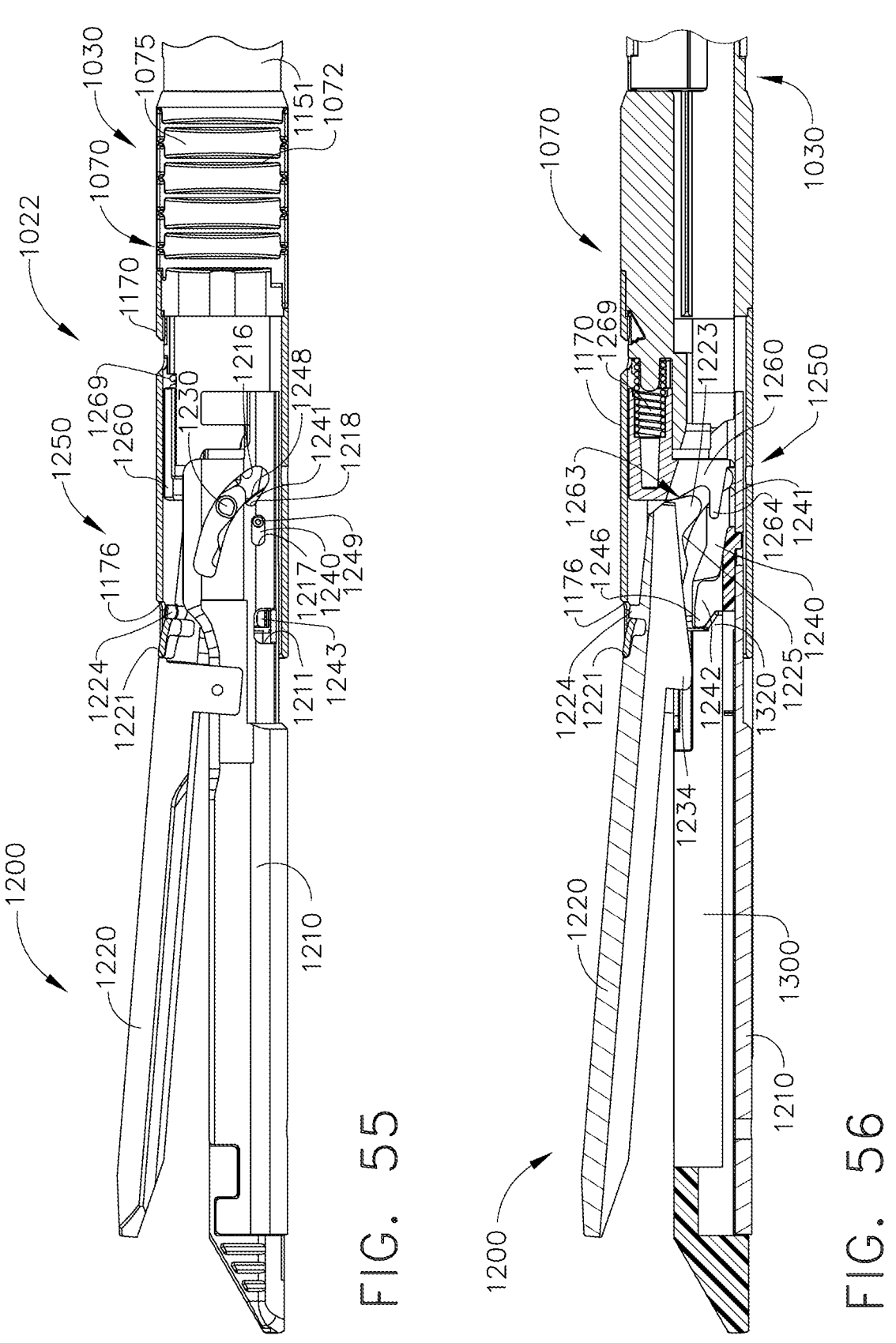
FIG. 55 is an elevation view of the end effector of FIG. 43 illustrating the staple cartridge positioned in the elongate channel and the anvil in a partially closed orientation, wherein the closure tube, depicted in cross-section, has been advanced distally to move the anvil into its partially closed orientation.
FIG. 56 is a cross-sectional elevation view of the end effector of FIG. 43 in the configuration illustrated in FIG. 55.
Figures 57, 58:
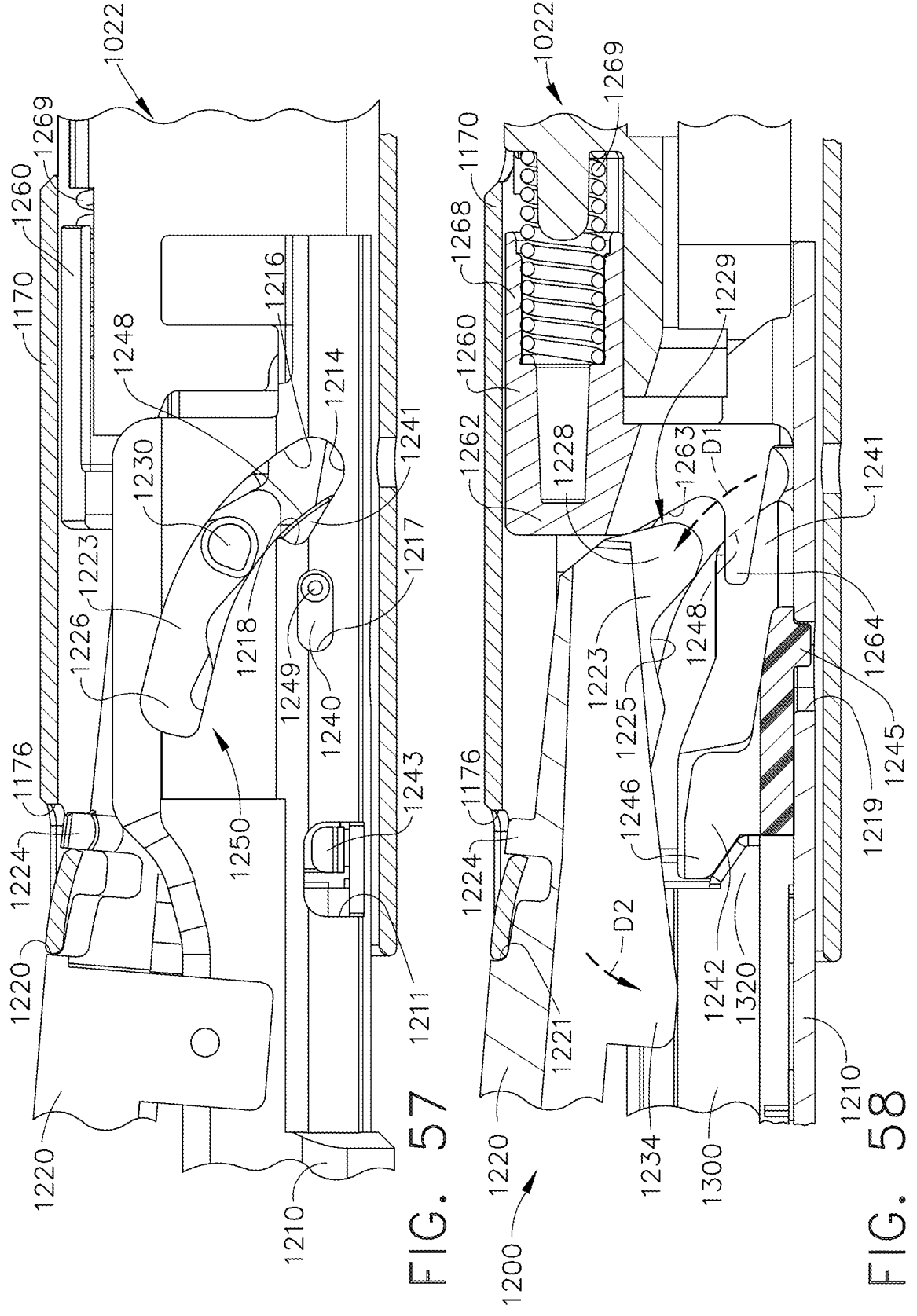
FIG. 57 is a detail view of the anvil lockout system as depicted in FIG. 55.
FIG. 58 is a detail view of the anvil lockout system as depicted in FIG. 56.
Figures 59, 60:
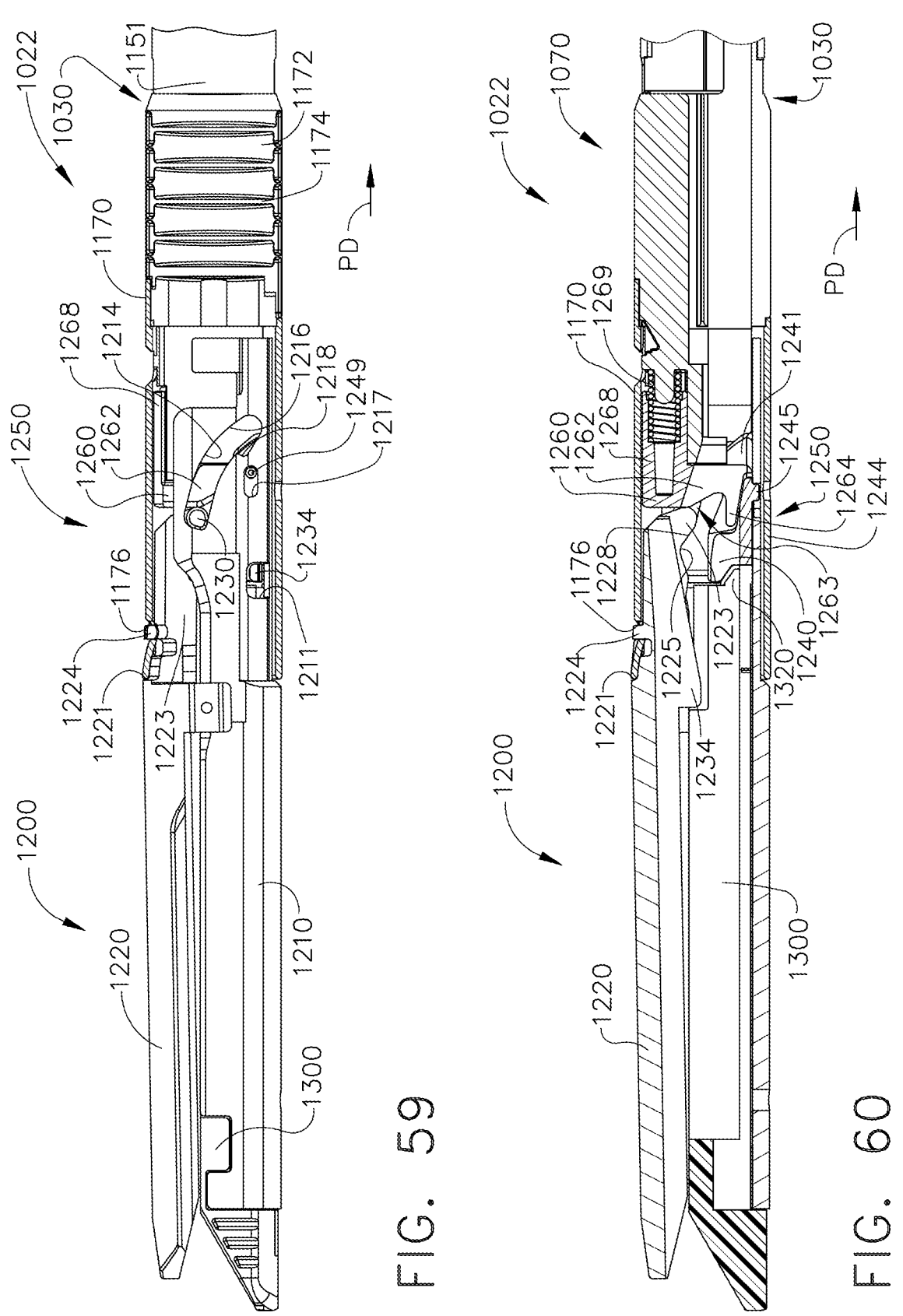
FIG. 59 is an elevation view of the end effector of FIG. 43 illustrating the staple cartridge positioned in the elongate channel and the anvil in a fully clamped orientation, wherein the closure tube, depicted in cross-section, has been advanced distally to move the anvil into its fully clamped orientation.
FIG. 60 is a cross-sectional elevation view of the end effector of FIG. 43 in the configuration illustrated in FIG. 59.

Referring still to FIGS. 52-54, a portion of the shiftable guide 1240 can be in abutting engagement with a portion of the proximally extending mounting portion 1223 of the anvil 1220. For example, the proximal end and abutment surface 1248 of the barrier wall 1241 of the shiftable guide 1240 can be positioned against a contoured edge 1225 of the trunnion wall 1226, 1228. In such instances, proximal shifting of the shiftable guide 1240 can also affect proximal shifting of the trunnion walls 1226, 1228 of the mounting portion 1223. For example, the barrier walls 1241 can push the contoured edges 1225 of the trunnion walls 1226, 1228 in the proximal direction "PD". In various instances, the shiftable guide 1240 can overcome the spring force generated by the spring 1269 engaged with the lock member 1260 of the anvil lock system 1250, for example, to shift the mounting portion 1223 proximally. When the cartridge 1300 is fully loaded into the elongate channel 1210, referring primarily to FIG. 52, the anvil mounting portion 1223 can be moved proximally such that the trunnions 1230 are pushed out of their respective locking notches 1218. For example, the trunnions 1230 can be moved into the bottom of the arcuate slot segment 1216 such that the trunnions 1230 and the anvil 1220 are in an "unlocked" or "actuatable" position, for example, whereby the anvil 1220 may be pivoted closed by actuating the closure trigger 152 (see, e.g., FIGS. 1 and 2).

When the staple cartridge 1300 is fully seated within the elongate channel 1210 and the shiftable guide 1240 is biased proximally, as described herein, at least a portion of the shiftable guide 1240 can overlap the locking slots 1218 in the elongate channel 1210. For example, the shiftable guide 1240 can be shifted proximally such that the barrier portions 1241 are longitudinally aligned with the locking notches 1218. In certain instances, the barrier portions 1241 can longitudinally overlap the locking notches 1218, for example, and can be longitudinally offset from the arcuate slot segments 1216, for example. Referring to FIG. 52, the barrier portions 1241 can be shifted such that they at least partially cover and/or block the locking notches 1218 in the elongate channel 1210; however, in such a position, the barrier portions 1241 may not cover and/or block the arcuate slot segment 1216, for example. Moreover, when the barrier portions 1241 longitudinally overlap the locking notches 1218, the barrier portions 1241 can block the trunnions 1230 from entering into or accessing the locking notches 1218. In such instances, the trunnions 1230 can be guided away from the locking notches 1218 and along the arcuate slot segments 1216, for example.

When the surgical stapling instrument 10 is in its open, unfired configuration, as illustrated in FIG. 1, both of the triggers 152, 102 can be in an unactuated or, shifted-forward, position and, when the proper staple cartridge has been properly loaded into the end effector 1200, the anvil 1220 can be in an actuatable position, such as would be typical after inserting the loaded end effector 1200 through a trocar or other opening into a body cavity. The instrument 10 can then be manipulated by the clinician such that the tissue to be stapled and severed by the end effector 1200 is positioned between the staple cartridge 1300 and the anvil 1220. As discussed above, movement of the closure trigger 152 toward the pistol grip 24 (FIGS. 1 and 2) can affect distal movement of the proximal closure tube segment 1151, the flexible neck assembly 1070 and the distal closure tube segment 1170. Moreover, referring now to FIGS. 55-58, as the distal closure tube segment 1170 moves distally, it can contact the closure ledge 1221 on the anvil 1220. The anvil 1220 can contact the tissue and push the tissue against the staple cartridge 1300 to create clamping pressure within the tissue. As the reader will appreciate, different types of tissue can react differently to the clamping pressure applied thereto; nonetheless, the tissue can apply a reactive force to the anvil 1220 which can cause the anvil 1220 to move along a path which is at least partially defined by the arcuate trunnion slot segments 1216. In any event, the surgeon can pivot the anvil 1220 relative to the staple cartridge 1300 to manipulate and capture the desired tissue in the end effector 1200.

When the cartridge 1300 is fully seated in the elongate channel 1210, as discussed above and referring primarily to FIG. 57, the proximal edge and abutment surfaces 1248 of the barrier walls 1241 can extend proximally past the locking notches 1218. As also discussed above, a portion of the barrier walls 1241 can longitudinally overlap the locking notches 1218 and the proximal edges of the barrier walls 1241 can be at and/or near the boundary between the locking notches 1218 and the arcuate slot segments 1216. In various instances, the proximal edges and abutment surfaces 1248 of the barrier walls 1241 can be longitudinally aligned with a portion of the edge of the arcuate slot segments 1216, for example, such that the proximal edges of the barrier walls 1241 guide the trunnions 1230 along the arcuate slot segments 1216 when the anvil 1220 is being closed relative to the cartridge 1300, for example.

Once the tissue has been positioned between the anvil 1220 and the cartridge 1300, in various instances, the clinician can move the closure trigger 152 (see, e.g., FIGS. 1 and 2) proximally until positioned directly adjacent to the pistol grip 24 (see, e.g., FIGS. 1 and 2), for example, locking the handle 20 (see, e.g., FIGS. 1 and 2) into the closed and clamped position. When the anvil 1220 is in its fully clamped position, referring now to FIGS. 59 and 60, the anvil trunnions 1230 can be located in the upper end of the arcuate slot portions 1216. After the tissue has been clamped, the clinician can move the firing trigger 102 (see, e.g., FIGS. 1 and 2) proximally causing the knife bar 130 (see, e.g., FIGS. 2 and 3) to move distally into the end effector 1200. In particular, the knife bar 130 can move through the slot 1236 in the pivot tab portion 1234 of the anvil 1220 and into the slot 1304 in the cartridge body 1302 to contact the wedge sled operably positioned within the staple cartridge 1300. As the knife bar 130 is driven distally, it can sever the tissue captured between the anvil 1220 and the staple cartridge 1300 and drive the wedge sled distally which can cause the staples to be sequentially fired into forming contact with the staple-forming undersurface 1222 of the anvil 1220.

In various instances, the clinician can continue to move the firing trigger 102 until it is adjacent the closure trigger 152 and the pistol grip 24. In certain instances, a single actuation of the firing trigger 102 can be sufficient to deform all of the staples removably stored in the staple cartridge 1300 while, in other instances, more than one actuation of the firing trigger 102 may be required to deform all of the staples removably stored in the staple cartridge 1300. Concurrent with the staple deformation, the cutting edge 132 (FIGS. 2 and 3) of the knife bar 130 can traverse through the tissue T. Once the tissue has been sufficiently stapled and incised, the firing trigger 102 can be released and the anvil 1220 can be opened to release the tissue captured within the end effector 1200. In certain instances, the anvil 1220 can be opened by depressing the release button 120 (FIGS. 1 and 2)

while simultaneously squeezing the closure trigger 152. Such action can result in the movement of the distal closure tube segment 1170 in the proximal direction "PD". In such instances, the anvil tab 1224, which can be engaged by the opening 1176 in the distal closure tube segment 1170, can cause the anvil 1220 to pivot open. Additionally, in various instances, the downwardly protruding pivot tab 1234 (FIG. 6) extending from the anvil 1220 can push against the spent cartridge 1300 to pivot the anvil 1210 back to the open position shown in FIGS. 51-54. In various instances, the spent staple cartridge 1300 can then be removed from the elongate channel 1210 and an unspent staple cartridge can be positioned in the elongate channel 1210 in order to reuse the surgical instrument and end effector 1200 once again.

In various instances, when the spent cartridge 1300 has been removed from the elongate channel 1210, the end effector 1200 can return to the "unloaded" and open position depicted in FIGS. 48-51, for example. In such instances, the spring-loaded anvil lock system 1250, e.g., the spring 1269 and the camming surface(s) 1263 of the anvil lock member 1260 can bias the end surfaces 1227 and 1229 of the trunnion walls 1226 and 1228 distally, which can shift the trunnions 1230 into the locking notches 1218 of the trunnion slots 1214, for example. Moreover, the contoured surfaces 1225 of the anvil mounting portion 1223 can bias the biasing surfaces 1248 of the shiftable guide 1240 distally, which can shift the shiftable guide 1240 distally, such that the shiftable guide 1240 is longitudinally offset from the locking notches 1218, and thus, can unblock access to the locking notches 1218, for example.

The various unique and novel features of the above-described embodiments serve to prevent the end effector from being closed when a surgical staple cartridge is not present or has not been properly seated within the elongate channel. When the anvil is in the locked position wherein the anvil trunnions are retained in their respective locking notches, the anvil is retained in the open position. When in the open position, the end effector cannot be inadvertently inserted through a trocar. Because a full closure stroke is prevented, the firing system cannot be actuated. Thus, even if the clinician attempts to actuate the firing trigger, the device will not fire. Various embodiments also provide the clinician with feedback indicating that a cartridge is either not present or has not been properly installed in the elongate channel.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
   (a) a first jaw comprising a pivot slot, wherein the pivot slot comprises a closure path portion and a lock portion;
   (b) a second jaw, wherein one of the first jaw or the second jaw is configured to receive a staple cartridge and the other of the first jaw or the second jaw is configured to form staples ejected by the staple cartridge, and wherein the second jaw comprises a trunnion movably positioned in the pivot slot; and
   (c) a spring configured to bias the trunnion into the lock portion to prevent the second jaw from moving from an open position to a closed position when a staple cartridge is absent from the one of the first jaw or the second jaw,
   wherein in response to insertion of the staple cartridge into the one of the first jaw or the second jaw, the second jaw is configured to be actuated by the staple cartridge such that the trunnion advances out of the lock portion into the closure path portion of the pivot slot, wherein the trunnion is movable within the closure path portion to thereby permit the second jaw to move from the open position to the closed position.

2. The surgical instrument of claim 1, wherein the spring includes a leaf spring.

3. The surgical instrument of claim 1, wherein the spring is configured to directly contact the second jaw and is fixed relative to the first jaw.

4. The surgical instrument of claim 1, wherein the spring is positioned proximal to the second jaw.

5. The surgical instrument of claim 1, wherein the second jaw is positioned above the first jaw, wherein the spring is positioned above the second jaw.

6. The surgical instrument of claim 1, wherein the spring is configured to apply a downward force onto the second jaw.

7. The surgical instrument of claim 1, wherein the surgical instrument includes the staple cartridge.

8. The surgical instrument of claim 1, wherein the second jaw includes a second jaw mounting portion positioned distally to the trunnion, wherein the second jaw mounting portion is configured to engage the staple cartridge.

9. The surgical instrument of claim 1, wherein the second jaw is configured to be urged in a proximal direction upon engagement with the staple cartridge.

10. A surgical instrument, comprising:

(a) a first jaw comprising a pivot slot, wherein the pivot slot comprises a closure path portion and a lock portion;

(b) a staple cartridge insertable into the first jaw, wherein the staple cartridge comprises a plurality of staples removably stored therein;

(c) a second jaw movably mounted to the first jaw, wherein the second jaw comprises a staple forming portion configured to deform staples, wherein the second jaw is movable between an open position and a closed position, and wherein the second jaw comprises a protrusion movably positioned in the pivot slot; and (d) a spring configured to contact the second jaw to thus bias the protrusion distally and into the lock portion to prevent the second jaw from moving from the open position to the closed position when a staple cartridge is absent from the first jaw.

11. The surgical instrument of claim 10, wherein the spring includes a leaf spring.

12. The surgical instrument of claim 10, wherein the spring is configured to directly contact the second jaw and is fixed relative to the first jaw.

13. The surgical instrument of claim 10, wherein the spring is positioned proximal to the second jaw.

14. The surgical instrument of claim 10, wherein the spring is positioned above the second jaw, wherein the first jaw is positioned below the second jaw.

15. The surgical instrument of claim 10, wherein the spring is configured to apply a distal force onto the second jaw.

16. The surgical instrument of claim 10, wherein the second jaw includes a second jaw mounting portion positioned distally to the protrusion, wherein the second jaw mounting portion is configured to engage the staple cartridge.

17. The surgical instrument of claim 10, wherein the second jaw is configured to be urged in a proximal direction upon engagement with the staple cartridge.

18. A surgical instrument, comprising:

(a) a first jaw comprising a pivot slot, wherein the pivot slot comprises a closure path portion and a lock portion;

(b) a staple cartridge insertable into the first jaw, wherein the staple cartridge comprises a plurality of staples removably stored therein;

(c) a second jaw movably mounted to the first jaw, wherein the second jaw comprises a staple forming portion configured to deform staples, wherein the second jaw comprises a trunnion movably positioned in the pivot slot, and wherein said second jaw is movable between an open position and a closed position with the trunnion along the closure path portion; and (d) a spring configured to apply a force onto the second jaw in a downward and distal direction to thereby bias the trunnion into the lock portion to thereby lock the second jaw into the open position such that the second jaw is inhibited from transitioning into the closed position until the staple cartridge has been inserted into the first jaw.

19. The surgical instrument of claim 18, wherein the second jaw includes a second jaw mounting portion positioned distally to the trunnion, wherein the second jaw mounting portion is configured to engage the staple cartridge.

20. The surgical instrument of claim 18, wherein the second jaw is configured to be urged in a proximal direction upon engagement with the staple cartridge.

* * * * *